United States Patent
Mikati et al.

(10) Patent No.: US 11,717,560 B2
(45) Date of Patent: Aug. 8, 2023

(54) COMPOSITIONS COMPRISING NUCLEIC ACID MOLECULES AND METHODS OF TREATING ATPASE-MEDIATED DISEASES

(71) Applicant: DUKE UNIVERSITY, Durham, NC (US)

(72) Inventors: Mohamad Mikati, Durham, NC (US); Arsen Hunanyan, Durham, NC (US); Boris Kantor, Durham, NC (US); Aravind Asokan, Durham, NC (US); Ram Puranam, Durham, NC (US); Dwight Koeberl, Durham, NC (US)

(73) Assignee: DUKE UNIVERSITY, Durham, NC (US)

( * ) Notice: Subject to any disclaimer, the term of this patent is extended or adjusted under 35 U.S.C. 154(b) by 0 days.

(21) Appl. No.: 17/524,466

(22) Filed: Nov. 11, 2021

(65) Prior Publication Data

US 2022/0088152 A1    Mar. 24, 2022

Related U.S. Application Data

(63) Continuation of application No. PCT/US2020/032978, filed on May 14, 2020.

(60) Provisional application No. 62/847,416, filed on May 14, 2019.

(51) Int. Cl.
*A61K 38/48* (2006.01)
*A61P 25/28* (2006.01)
*A61K 48/00* (2006.01)

(52) U.S. Cl.
CPC .......... *A61K 38/48* (2013.01); *A61K 48/0058* (2013.01); *A61P 25/28* (2018.01)

(58) Field of Classification Search
None
See application file for complete search history.

(56) References Cited

U.S. PATENT DOCUMENTS

| | | | |
|---|---|---|---|
| 7,473,531 B1 * | 1/2009 | Domon | C07K 16/4266 435/7.1 |
| 9,061,059 B2 * | 6/2015 | Chakraborty | C12P 13/04 |
| 10,668,094 B2 * | 6/2020 | Karlish | A61P 27/06 |
| 11,077,128 B2 * | 8/2021 | Karlish | A61P 27/06 |
| 11,112,407 B2 * | 9/2021 | Komorowski | G01N 33/564 |
| 2003/0225017 A1 | 12/2003 | Murdin et al. | |
| 2010/0095387 A1 | 4/2010 | Smith et al. | |
| 2014/0057969 A1 | 2/2014 | Frost et al. | |
| 2017/0348435 A1 | 12/2017 | Murillo Sauca et al. | |

FOREIGN PATENT DOCUMENTS

| | | | |
|---|---|---|---|
| WO | 2012178173 A1 | | 12/2012 |
| WO | 2014007858 A1 | | 1/2014 |
| WO | WO2020/142653 | * | 1/2019 |
| WO | 2019/199841 | | 10/2019 |

OTHER PUBLICATIONS

International Search Report and Writte Opinion dated Oct. 15, 2020 for corresponding International Patent Application No. PCT/US2020/032978, 14 pages.
Clapcote SJ, et al. (2009) Mutation I810N in the alpha3 isoform of Na+,K+-ATPase causes impairments in the sodium pump and hyperexcitability in the CNS. Proc Natl Acad Sci USA. 106(33):14085-14090.
Ghusayni R, et al. (2020) Magnetic resonance imaging volumetric analysis in patients with Alternating hemiplegia of childhood: A pilot study. Eur J Paediatr Neurol. 26:15-19.
Heinzen EL, et al. (2012) De novo mutations in ATP1A3 cause alternating hemiplegia of childhood. Nat Genet. 44 (9):1030-1034.
Helseth AR, et al. (2018) Novel E815K knock-in mouse model of alternating hemiplegia of childhood. Neurobiol Dis. 119:100-112.
Holm R, et al. (2016) B. Neurological disease mutations of α3 Na+,K+-ATPase: Structural and functional perspectives and rescue of compromised function. Biochim Biophys Acta. 1857(11):1807-1828.
Hunanyan AS, et al. (2015) Knock-in mouse model of alternating hemiplegia of childhood: behavioral and electrophysiologic characterization. Epilepsia. 56(1):82-93.
Hunanyan AS, et al. (2018) Mechanisms of increased hippocampal excitability in the Mashl+/− mouse model of Na+ /K+ -ATPase dysfunction. Epilepsia. 59(7):1455-1468.
Ikeda K, et al. (2017) Knockout of sodium pump α3 subunit gene (Atp1a3−/−) results in perinatal seizure and defective respiratory rhythm generation. Brain Res. 1666:27-37.
Isaksen TJ, et al. (2017) Hypothermia-induced dystonia and abnormal cerebellar activity in a mouse model with a single disease-mutation in the sodium-potassium pump. PLoS Genet. 13(5):e1006763.
Kirshenbaum GS, et al. (2013). Alternating hemiplegia of childhood-related neural and behavioural phenotypes in Na+,K+-ATPase α3 missense mutant mice. PLoS One. 8(3):e60141.
Masoud M, et al. (2017) Diagnosis and Treatment of Alternating Hemiplegia of Childhood. Curr Treat Options Neurol. 19(2):8.
Mikati MA, et al. (2000) Alternating hemiplegia of childhood: clinical manifestations and long-term outcome. Pediatr Neurol. 23(2):134-141.
Severino M, et al. (2020) White matter and cerebellar involvement in alternating hemiplegia of childhood. J Neurol. 267 (5):1300-1311.
Ye Q, et al. (2017) The AAA+ ATPase TRIP13 remodels HORMA domains through N-terminal engagement and unfolding. Embo J. 36(16):2419-2434.
Extended European Search Report dated Dec. 22, 2022 for EP Application No. 20805008.8.

* cited by examiner

*Primary Examiner* — Hope A Robinson
(74) *Attorney, Agent, or Firm* — Polsinelli PC

(57) ABSTRACT

The present disclosure provides nucleic acid expression cassettes, vectors, compositions and methods for the treatment of ATPase-mediated diseases in a subject.

17 Claims, 22 Drawing Sheets
(8 of 22 Drawing Sheet(s) Filed in Color)
Specification includes a Sequence Listing.

SEQUENCE LISTING

<160> NUMBER OF SEQ ID NOS: 22

<210> SEQ ID NO 1
<211> LENGTH: 32116
<212> TYPE: DNA
<213> ORGANISM: Homo sapiens

<400> SEQUENCE: 1

```
gatggagaga tgcagggatc tggagacgcg gagacaccgg aagcggagac acagaaagac        60
agaaaacaga tggggctggg ggaggggagg gccagtgagc tgttgagtgt ggccgtgcct       120
ggggtggcga gtgtgtgcct gggccggggt gattcagtga cgttgtgatc gtgtgtgcac       180
gcatctgcga ggccatcttc aactgtctgt ggctgtgatc ccgtgtttct gttgaaaatg       240
tacctcccca accccaaga gaggaagtga ggaatcccag tagactgggg ggtgggtggg        300
cgggcagggg tgggagaggc tgaagggctg atggcgcagg agaaaggtgg gtccgccttc       360
tgtccccgcc ctccctgccc cgccggaggt ttctgtggaa actgcagctg aggaaggacg       420
agtgaaggtc acacagcaag agccaaaacg aggccgagca gaaagggaga gatggaggga       480
tggcgagaga cagagatggg gagagacaac gaaggggggca gagtgggcgg gaggggatg       540 gggagagaga gctagaggac acagagccgg cgagacaggg agagaggctg ggtgaggtga       600
gagaagactg gagaaagaat agagggctga gaccagaggt gaagcgggag ggtaagatac       660
acccggagtt ggggtgagag acaggaagcc ataaaaaact aaatggaacc tggagggggac      720 tggaacggaa aggaaagcct gactggaaag gtcccagaga gagcgaggct gcgcccgttc       780
ctgggcggcg gcccggggct tgggagctgt ccgttcagca cccagttggc cagcctgagc       840
ccagagcgcc cgacttccct ccagggcccg cctgcccagc gcagtcctgg caggccggcc       900
acaccctggg agacccctcc ccgcacacag cgccccccgt cgccacccgt cccttctgc       960 gtctcagacc ctggttgcgt gccccctcgga caggtgtggg ggcaggcacc agcctctctc      1020
tgttgtctcg catctctatc tccacgtctc ttacacactc caatcaatgt ctctgccctt       1080
gggtcggact ctttgtcgag gtgactagaa catgattaca gacatttctg gtttctcccc       1140
cttctctgtc ccaatgcctc gaggccaatt ccctctgggg tctcccccat ttctgagtcc       1200
ccggtcccct accaggtttc tgctcagtct cccccctggcc tttatctctg agtctccctg      1260
gtttaccaag cctgtctctg cctggctgtc tacgtctctc tgtctctgtc accttcactg      1320
aactcttccg ttgctctgtc tccgtgttct catctctgca tctgccaatc tctgtctgtc      1380
tttttcaatc tgtttgtatc cgcctctctc tggttctggg ctgctgttt ctccctctgt       1440 gtctctcctt ccgcctctca catctagctc cccctattccc ctttatccct gtgaccttcc     1500
caggtctttc cttctcaccg cccccctac ttctgcagag cctcaccagg agcacgatgc       1560
acagtcatca gtctcatcag gctcgtgcct gaggagagag tgcatgaggg gggacgtgag      1620
```

| | |
|---|---|
| cttgtgtctg aggtgggatg ggaagggctc aaggcctccc ccggcccagc tggagagcaa | 1680 |
| gagcagacag agcctagaat ctcctggaat ccaggcctcc cccacctccc caggcttccc | 1740 |
| catctcccca gtcccattct ccatggtcca ggcccatgcc tctaggccaa ggtgtcaaga | 1800 |
| gaaggaaagg aggatatgtt gataggctct ccctccccta ggaagagggc agagttgggg | 1860 |
| aggggcgtc tgggggtgag gcatctgggt taaaagatgt ggctcctccc cctttcccag | 1920 |
| tctccatggc aacagcccag tctgcaggcc aacctcctt tgctgcagaa gcagctccct | 1980 |
| gttaccatgg caacaaagga cagcgagaaa gatggggacg ggtcagagga caggattggg | 2040 |
| atggggctct gggcactggg gaaagcctcc attcactctc tggccttgtc tctgtccata | 2100 |
| tgctgtggct ctgaatctct gtgtttctgt gcctctctct ggccttcagc ctttcacaca | 2160 |
| tttccctgca ccaggtcctc gaccttcacc cacccaccct catacaccaa gctcactccc | 2220 |
| tgtcccttgc ctgcgtcccc cacatctcct atcccatagg tggagaggat acccacattc | 2280 |
| tgagaaaact acaaggtcaa atgctctctg tctctctctc tctctcttcc ccttctacca | 2340 |
| tccccaggga gagtctgggg tgttcctcat agaacaaagt ggtgttggag tgagtgggga | 2400 |
| ggcctcaact tcttgggctc cagtggggtg gctgatgggg tgttgtgtgt cggcagcagg | 2460 |
| cctggggtgt gggtgccggc tgtgcatctg tgtgtgtaca tatactgtga cgagctctgt | 2520 |
| gtgtcatgtg ggtgagggcg ttggggtgtg tttggaggtg caacaaagat gtctgcgata | 2580 |
| gtgctgcaat aacgtgatgt gtgtatgtgt gggaggtgtg tgggtgtcgc gtgacttgtg | 2640 |
| tttgaattat tgtgctatgt gtaagtgtgt gcaccttttt gtctgtcatt cacagttagc | 2700 |
| attggcaact ttgcactgtg ggccgttgct catgcccaaa cacactgggg agcagtgtgt | 2760 |
| gtgaggatgt gtgcgacatc gtgggatcat gcaacgatgt ccacaaaggc tgatgtagtg | 2820 |
| tgtctggagg cagtgtgagg cctgtgcgtg tgtgatggtc ctgagtgcag gtgtgtgttg | 2880 |
| gtttatgggt tgcacgatgt gggtttctat gtgagatggt gggaggtcag gtgtggtaga | 2940 |
| gtgtgtgatg tgtgagtctg cgattttctg agtgtcggtg ttagtccgca cagcactttg | 3000 |
| tggctgtgat tatgagtctc ttgtggtgtg atgggtgtgt aaggtgtgtg ccctatgtgt | 3060 |
| gtttcactct atgtttgaga ctctgtgtgt ggtggggtgg tgttgtgtgt gtgagggtac | 3120 |
| atgctggcct atggtggaat atgagtgcaa ccctgtggtg tgtgcgtgtc cccagcatct | 3180 |
| gggctatcag tgtgatggtc ctgtgtaact gtgacgctgg gcattttctg ggcctcctgg | 3240 |
| ggccatcctc caccgtgttg tgtctcccgt gtaccctgtg tggttgtggc tcattggata | 3300 |
| gctcaggcgt agtgggggggg cacccacagt gagggaatct cagggctcct cccgccagca | 3360 |
| ccctcctca attgcaaggc ctttcttgct ctcttgtgtt cccttccaac ttcccctcct | 3420 |
| gcagggccct ctccctgaac agcactaccc cccgccgtct ccagggtccc tggtgccaca | 3480 |
| ctgcagtgat tcaccgggct tccctcccac cccgtgtcac tacccgcccc cctcccccca | 3540 |
| gcgtacccTT ctcggtgatg gcacaccccc acaatgagag gatttccggg gtttTCTTTC | 3600 |
| cctgagcgcc ccttcttgga ggccctactc catattgagg gggtctccaa gtcccctatt | 3660 |
| gcggaggtct ctgggaatcc ccccaccccc gcagcgctcc ccttcgcgg ccgcgccgcc | 3720 |
| actttgcgga gccaagggg aggacagctg cagtaccagg ggcggggccg cgggccgtcc | 3780 |
| gtcagcacgg cggcgcccct gattggccag cgccgccccc ctcccgcgga cgcgggcata | 3840 |
| tgaggaggcg gaggcggcgg ccgccgcagc ctctgtgcgg tggaccaac ggacggacgg | 3900 |
| acggacgcgc gcacctaccg aggcgcgggc gctgcagagg ctcccagccc aagcctgagc | 3960 |

-continued

```
ctgagcccgc cccgaggtcc ccgccccgcc cgcctggctc tctcgccgcg gagccgccaa    4020
gatgggggta ggtgctgagc cggctgggcg ccgcttccgt gtgacattgt ggggccggtg    4080
acattgggtg tgcgcggggg gcgggggcac cgggaccccct gcgctccggg gccaggcctg   4140
cgagacccgg ggagccggct gacccagcca atccatgtgg tcgtggggcc gcaggggggcg   4200 gcgggggggtc tgtggcgcac gttggcatgg ctttgtgtgc ggagatccgc gaggttgtgg   4260
gccagccctc agcatctccg cctgaccttg tgcggttgca tgtgcacagt tgcatgtgcg    4320
tatgagagct gctggctctg tcaggccctg gcagcgagtg tgtgggcccc gtggtgtctg    4380
aaagtctgcg atcgcgtctg ggtgtgtctg tgagagctcg tgttagtgcg tctggggtta    4440
ttgaggcccc cctgcttccc tggcagggtg cggataggtc cacgttgtgg gatggacacc    4500
agatgacctc tctttctcct tccaggcctg gatggggggga ctccgcagtg tgtgtgtgtg    4560
tgtgtgtgtg tgtgtgtgtg tgtgtgtgtg tgtgcagg ctccgcagtg tcgcagcctg      4620
gggctgcagt gtgtgtgtgt gcagccccctc atgtagggga gcaggcatgg gaggctggga    4680
ggaggagagg aacaggagag ccacggtggg gagactgagt gcacagctga gggtgtgcgt    4740
gtgcaactgt gtagtgggga gcgtgcatgc ctggctgtgt ccttgcctct gtgtccgtgt    4800
gtccttgtct gtctgtgagt ctctccagca gatgccgcct ccctccctgg ctgaccacct    4860 gaccccttgct gcagccctgg attcctccct gtgtgtctgg ggcggggctg aagggagggg    4920
gaatcaggag aggaggggt gggtgggggt aggtgggatg aagagggcgg gagaggccag     4980
tggagggaga ataggagggc tggggagaaa gatggcggat aaaggctgat gggcccaggg    5040
atggaggtgg gggatggggc tgcagatctg tggggtgggg cagggtgggc cggggggctg    5100
ggaaggagga ttgggttggg gcaggactag gggagagaag ggagaaaggg gtagtcagtg    5160
atggctgtca ggtaagtggg atggaggggag ggaagctgtg gatggattgg gagaagactg   5220
atgctaaaag ccctagagaa ggaagttaga gggaggtggt cttaggaaac ggagtgggga    5280
cgagaggaga aatgaaggca gcttagacat gggaaggaaa gacagagaca catggaaaga    5340
cagagatgct ctgaaagaga cagagaaaga gacatggaca tagagacaaa gagacagaga   5400
caagcagaga gacatggctg agacacatgg agagacattg agagagaaaa tgagaaactg    5460
aggctcagag gaagagacac aaggacagat atttcctatc tagcggcaac cacagtcagc    5520
ctgagggaca ggaagaggag gcagagggca aaggggagg tcaagggagg gatggtcaga    5580
gatgtgggcc aggtcccctg cgaggggggaa gggaggccgg cccaggcgca gaggctgcgg    5640
gagctggcac cagatcaggg agaggcggac agcatggaaa atggcaagga gctgcagagg    5700
cggccacagc gagacaggca tggtccccac ccttggaggt gctcccaccc cgcagcgcgc    5760
ccatctgggc ctcctgcctt gactgggaaa gcctcagctg tgcactccaa cagatgggag    5820
cctgctcccc aaggggggtct ggctgtgtca agggcaagca ggagccaagg ccagggccag   5880
ggtgagccag gagtcccagg gtccggtcc ctcctccctc agaccaggag tccaggcccc     5940
agcccctcct ccctcagatc caggagtcca ggccccagcc cctcttccct cagaccagga    6000
gtccaggccc cagcccctcc tccctcagac caggagtcca ggccccagcc cctcctccct    6060
cagatccagg agtccaggcc ccagcccctc tccctcaga tccaggagtc caggcccag     6120 cccctcttcc ctcagaccag gaatccaggc cccagcccct cctcctcag acccaggggt    6180 ccaggcccag cccctcctcc ctcagaccca agggtccagc cccagccct ctccctcag     6240 acccaggagt ccaggccctg gcccctcctc cctcagaccc aggattccag gctcccagtc    6300
cttcctccct cagacccagg ggtccagacc cctgcccctc ctccctcaga cccagggatc    6360
```

```
caggacccca gcctctctca gtatctgaga gtccggccca gcccttagca tttatggggc    6420
cccgagcatc agctcccagc cttcaactaa ggtttctggg tgggcagctg attttctccc    6480
tctctctctc ctgaccccca tctcacccct ctcctggcct cctgcacagg acttgacccc    6540
aggcctttgt agctccacat ctctccatct ctccatgtct ctccatcctg ggtctacccc    6600
atcgggcaaa gctgagacca ccccggcact gtagggcagt aggaaagatg gtctccccgt    6660
cccccaagcc tctgtgcctc cgcatctgag acgcagtgct gctgcagggc tggcgtgggg    6720
ccaagcctcc ctcccacccc ctgcacccct tcttgaggct cccagatctc caggctgctg    6780
cccctccctg cacaccccca ccctccgact cagcctctgg gtctggggc agacagcagg     6840
cagctcaggc cctctacaag gtcacgagga gattagcgct gagccgcgct gagcctccga    6900
tcccagcttg gccctgggcc tgcgggacct gtcagcggcc cctgcagcac ccagcctcgc    6960
cccaccccctc ccaccagcct cggacactgc cctccccatc cgcccaggct cccaaactgg   7020
aacttcaggg actcacacca tgcgcagttc aagccaggac tagggcttct gcctctaact    7080
ctcctgctct gtcctccagg aacctggcca tgcccagcct ctgttaagga cgctccatgg    7140
gcccaacaca tggaagatcc cagagagagg cagagacaga gatagaggaa ggtaccagag    7200
ggagacagtg agagagacag agacagagag acatagacag agatagagag gcagattcca    7260
gagacagaga gaggagatct cagagagaca gaaatagaga ataagatccc agagagaaag    7320
tgagagaaag agacagagag agagaggaag atcccagaga cagacagcga aagagagagg    7380
aagatcctac aaaaagagac agatatatat atatatatat atggacagag agagagagaa    7440
agagagagag agattgagga gagcccagag agagacagtg ggagaaagag agacagagag    7500
gaaaattcca ggatgaggta gtaagagaga gaaagagaat gagagatata tggggaagga    7560
gggggacgga agatttgaga gagacagaga gagggagaga gagaaagaga atgagagata    7620
tatgggaag gaggggacg gaagatttga gagagacaga gagagggaga gagagaaaga     7680
gaatgagaga tatatgggga aggaggggga cggaagattt gagagagaca gagagaggga    7740
gagagagaga gagaaagaga aagagaggag atcttagtga tagtgagaga gaaagagaga    7800
ttcagagata gagaggagat cccagagaga gagagtggga gagagacaga gataggcaga    7860
tcccagagag agatattaga gagacagaga gagagacaga gagaggttga aacaggaaaa    7920
gagacaggta gggagagatg tgagcatccc agaggagaca gcttgagaga tgaagataga    7980
gacacaatga cagagagaga cagaccgaaa gacggaaaaa gacagagaca gaaagtactg    8040
atccttgaga cgccaactca gagggaaata agaacccaga gagacagaaa ctcagccaga    8100
cctggggaga cacagccaag agatggagac agacatcatg caaggcagag agacaaagaa    8160
ccagagatca gagagacaaa aaatcataga aagacacatg cagagagacc cagagactgg    8220
gatcaggata gagaatgaca gagacaacat aaagagatca gagcgataga gagagagaga    8280
gagctatcaa gagagagaaa cagccttgca aagacagaga tacagagatg gagagataaa    8340
gagacaggag acagagagat gatgaaacaa agcaataaga ccaagagcca aaaacagacc    8400
tggagataca catcaaggga gacagacaga ggagaaagag atggagatac acgtggagac    8460
atagaaaaga cagatacgag gccgggcacg gtggctcacg cctgtaatcc cagcactttg    8520
ggaggccgag acgggcggat cacgaggtca ggagattgcg accatcctgg ctaacacagt    8580
gaaaccctgt ctctactaaa aatacaaaaa aatgagccgg gcgtagtggc gggcgcctgt    8640
agtcccagct actcgggagg ctgaggcagg agaatggcgt gaacctggga ggcggagctt    8700
```

```
gcagtgagct gagatcatgc cactgcactc cagcctaggc gactaagcga gactccgtct    8760
caaaaaaaaa aaaaaaaaaa agacagatat gtaggaaggt tggacagggc cagggagagg    8820
gaagaagaga cagaagcaga gttaaaatgt cacatagagg tggggcacgg tggcttattc    8880
ctataatccc aacagtttgg gaggctaaag caggaggatc gcttgagtcc aggagttaga    8940
gaccagcctg ggcagtgtag tgagacccca tttctagaaa aaaattaaaa attagccggg    9000
cgtggtggca cacctgta gtcccagcta cacaggaggc ggaggcggga ggatcacctg      9060
agcctcagaa gtcgaggctg cagtgagctg tgattgctgc actccagcct gggcatcaga    9120
gtgagacatt gtttcaaaaa acgaaaacaa agtcacatag acacagaaca caaaaggggga   9180 gagccccgca aagatgggca cagaaacaga gagagactga aacacaggca gaagccagac    9240
agggaccttc ggggacagag actcagagac acacagaacc agagacaggg aagctgattg    9300
cagcagatga gactcacgag gcctgagagt caccagaggc agaagggagg tgaagtcacc    9360
cagaggctcc gggagacaca gggagacccc gagaggcaga cagagacccc ccacccagag    9420
atgcaggggc accggccagg aggatagctg gggcatggag ggccggtgtc ctcctggaac    9480
cccttctcgc ccgcagtctg gtggctctga cagctatcgt atcgccacct cgcaggacaa    9540
gaaagatgac aaggactcac ccaagaagaa caagggcaag gagcgccggg acctggatga    9600
cctcaagaag gaggtggcta tggtaagcct cgccctctgc ccgcacaccc tcccagagaa    9660
cctcgccagt tcttggctgg cctaggcact caccgtctcc cccaaactcc tgttcctcag    9720
acagagcaca agatgtcagt ggaagaggtc tgccggaaat acaacacaga ctgtgtgcag    9780
gtgtggccag gctgtgggct gggaccctgg gaactaggga ggaggagctg ggggctagga    9840
cccctgggtc tgagggagga ggggctgtgg ctggtgtctt aagttctggg ggtctggtga    9900
aggcctgggg tgccagggtt gcccaggag ggttctgtgt gagtcctctg tccctcaggg     9960
tttgacccac agcaaagccc aggagatcct ggcccgggat gggcctaacg cactcacgcc   10020
accgcctacc accccagagt gggtcaagtt ttgccggcag ctcttcgggg gcttctccat   10080
cctgctgtgg atcggggcta tcctctgctt cctggcctac ggtatccagg cgggcaccga   10140
ggacgacccc tctggtgaca acgtgagtgc ctggaccctg ccctgtgcaa ggctctgcac   10200
atttatttac ggacaccgca ccccaacttc ttcccatccc tctaagcttt tcacagccca   10260 ctctcccccct ttttcccatc taactcacaa tcacccagca agagaaccag atcaaataca  10320
aggcaaactg aggctcagaa aagccaggct acttgtccaa ggccccacag caggatgtgt   10380
gagccggggc tctgtcccaa ggctgtgtga cctcagcggc cttgagaaca gacaccagca   10440
ggtggtcatg gcttgacaga tacccagagt gagtgtcaca tagagaccca ggcacacccc   10500
gctgctgata catcagggcc catccccata acacagggac acattcgaga tgcagcctca   10560
gatcccatgc gcataacaca gaccacacac cagccacaca gagctgctca cctgggtagg   10620
cgtgtgtgca cacacgca tgtgcacgga gggtcaacgc agatgccaca ccaggatgtg     10680
gtttcaaaca tggccaccta attcagaaac acagacacag actcagatat acactgacag   10740
agaaactcac acacacactg acacgcacac acacacacag caatgcaggc ataacctggt   10800
gacagagaga catgagagtc aggcacagag agtgtcctca gatgttcaaa tctaaacagt   10860
cttagacata agctctcaca gagaggcaga gctggagaca cagagacaga gatccacaca   10920
cagagaacca aagaagctgc cttgtagaat gtaaagtcag gcatgcagcc agtcagacag   10980
acacatggac agacagccgc atcccagact caacatgtgc aggaggacag acacacacac   11040
aaaacagatg gacaagtcgg gcatggtggc tcacgcctgt catcccagca ccttgggagg   11100
```

```
ccaaggcagg agggtaactt gagaccagga gttccagtag cctgagtaac atacccagac   11160
agacccagcc tctaaaaaaa cacaaaacat agccgggcct ggtggcgcac acctgtagtc   11220
ctagctactc cggaggctga ggagggagga ttgcttgaat ctgggaggtt gaggctacag   11280
tgaactgaga ttgtgccact gtactccatc ctaggcagca gagcgagacc ctgtctcaaa   11340
aaaaaaaaaa aaaaaaaatg ccaggaaaga tggctcacac ctgtaatccc agcactttgg   11400
gaggccaagg tgatagatca caaggtcagg agatcaagac catcctagcc aacatggtga   11460
agccccatct ctactaaaaa tacacaaaat tagccaggtg tggtggcatg cacctgtagt   11520
cccagctact caggaggctg aggcaggagg atcgcttgaa ccaggaggcg gagattgcag   11580
tgagccaaga tcatgccatt gcactccagc ctgggcgaca gagtgagact ctgtctcaaa   11640
aaaaaaatcg acagacccct tagattcaaac acaaccatta cagaaagagg gactcaagca   11700
caaacagggg agactcagac acaccaaccc tcataaccaa cctagggtca gacacacaaa   11760
tacagacccc cactgacaca aagctcccct cccagactcc aggcgagcag ggactggtgg   11820
agagtggctt gggcggcccc tgatcaacat ccccacatct ccccacagct gtacctgggc   11880
atcgtgctgg cggccgtggt gatcatcact ggctgcttct cctactacca ggaggccaag   11940
agctccaaga tcatggagtc cttcaagaac atggtgcccc aggtgaaggg tgcccagcaa   12000
ggggccagac gggggtgtta gtgtatgggc tgggggccgg gcccagtgac ccccaggcag   12060
agggagtctg ggaggtgaca ttactccatc ccacctcagc aagccctggt gatccgggaa   12120
ggtgagaaga tgcaggtgaa cgctgaggag gtggtggtcg gggacctggt ggagatcaag   12180
ggtggagacc gagtgccagc tgacctgcgg atcatctcag cccacggctg caaggtgggc   12240
ctgggcctag ggcccggctt taccctccct cgggctgccc aggagctcag gcccagcccc   12300
tcctccctca cactcaggag tccaggtccc aaccctcct ccctcagacc caggagtcca   12360
ggcccccagg ccctcctccc tcagacccag gagtttaggc cctgggccac ctcctcaccc   12420
aacagtcagg agtccaggcc cagccctcac cttttcggaga tccttaggga ccctagacct   12480
tggccagcag cactgtgcct tccccaccct caagatccca gcctctggcc tcccacacac   12540
cactcaccca ctgggcaccc aggcttctag ctgtgatctc caggcacaca ggcttcagcc   12600
ccaagccctg tacacaaata ccctcctgtc ccaggccctg gactgaaccc tctctctgct   12660
gcacctaccc ccaggtggac aactcctccc tgactgcga atccgagccc agactcgct   12720 ctcccgactg cactcacgac aaccccttgg agactcggaa catcaccttc ttttccacca   12780
actgtgtgga aggtgaggcg ggtgcagaga agacacacag ctggggcaga cacagggatg   12840
tgtcccaggg ggtcaggcct ccagaacctc cctgagccac cccacctcag cctaacccct   12900
ctggcctgca ggcacggctc ggggcgtggt ggtggcacg ggcgaccgca ctgtcatggg   12960
ccgtatcgcc accctggcat cagggctgga ggtgggcaag acgcccatcg ccatcgagat   13020
tgagcacttc atccagctca tcaccggcgt ggctgtcttc ctgggtgtct ccttcttcat   13080
cctctccctc attctcggat acacctggct tgaggctgtc atcttcctca tcggcatcat   13140
cgtggccaat gtcccagagg gtctgctggc cactgtcact gtaaggccag gctcctgggt   13200
ctgggtgggg agggcctggg ggtctgggct cctgggtctg aggaggagg ggctgggatc   13260 ctggacccct gagtctgagg gaggaggggc tagaggcctg gacccgtgtg tctggggag   13320 gaggggctgg gatctggacc cctgggtccg gagaagggc tggggcctg gatcacagta   13380 ttcttgtgaa agacaacttg ggcctgactc agagggcctc attaacaaag caaacaatca   13440
```

```
aagaaagaaa caaacaaaaa tcttgagaaa cactggcaag ccgtaaagag ccaacaatcc   13500
tattgcaaaa ttaagaagtg cacgctcatg atgaaaagtt gaagagtaca tcaagttaaa   13560
aaataaaata atgaggctgg gtgcactggc tcacgctgta atcccagcac tttgggggc    13620 caaggcgggc agatcagctg aggtcaggag ttcaagacta gcctggccaa catggtgaaa   13680
ccctgtctct actgaaaata caaaattagt ggggcgtggt ggcacatgcc tgtaatccca   13740
gctactcagg aggctgaggc aggagaatcg cttgaacctg ggaggcggag gttgcagtga   13800
gccaagatca cgccattgca ctccagcctg ggtgacaaga gtgaaactcc atctcaaaaa   13860
taaataaata aataaataaa ataaaataat aagcctggcg cagtggctca cgcctttaat   13920
cccaacagtt tgggaggctg aggcaggagg actgcttgag gtcaggagtt tgagacaagc   13980
ctggacaaca tagtaagaac ccatctctac caaaaaatgt gaaggctggg cgcagtggct   14040
catgcctgta gtcccaagac tttgggaggc cgaggcgggt ggatcacctg aggtcaggag   14100
ttcgagacca gactggccaa catggcaaaa ccccatctct actaaaagta taaaaattag   14160
ccaggcgtgg tgatgggtgc ctggaatccc agctactcag gaggctgaga caggagaata   14220
gcttgagcct aggaggcaga gcttgcagtg agccgagatc gtgccacctc actccagcct   14280
gggcgacaaa agcgagattc tgtctcaaaa aaaaaaaaa aaaaaaaaa atttttttaa    14340 attagccagg cgtggtggta catgtctgta gttccagcta tttgggaggc tgacccggga   14400
ggttgaggct gtagtgggcc atgattgaac cactgcactc tagcctgtgt gacagaggga   14460
gactccatct caagaaaata ataataataa taattattat aataataata attattatta   14520
ttatttttaa aaattttttc tctggctgct ttgctgccag cttcacccca gaagtccatt   14580
ctctgtgagg ttccgcctga cagctgtgag catattgact aaatgctgtc ttcaaggtgc   14640
atggcaggga ctatcttaga aataccattc tcctctttca ttctttgact taatgttta   14700 tgtgaagttt tccatattag ggccgggcag ggtggctcac gcctgtaatc ccagcacttt   14760
gggaatccga ggtgggtgga tcacttgagg tcaggagttc aagaccagcc tggccaacat   14820
ggcaaaaccc catctctact aaaaatacaa aaattagcca ggcgtgatgg tgggcgcctg   14880
taatcccagc tacttgggag gctgaggcac aagaattgct tgaacctggg aggtggaggt   14940
tgcagtgagc tgagatcgag ccactgcact ccagcctgga cgacagagca agactgtgtc   15000
tcaaaaaaaa aaaagtttta ctgtttttcca tattagcaat gttgaatgct acccatgtc   15060 aaatggattt ttatacgcaa aggattaagc atattgtgag cacatagtct gatgatttgg   15120
ggcaaactga acagaatcac gtcagctgca acgagactgc gtctccctga agccccctca   15180
agaccttatt tagcccctgc ccccaaccc aagggtaacc cctgatctgg ctgctaacag    15240
catagattaa ctttgcctgt gttcaaactt cctattaacg gaataattca gtatgaactc   15300
atttctggct cttttttggct gaacatgttt ttgacgttca cccatgcagg tgcaggcagc   15360
agtaatgtat ttgttttttat caatgttagt attccattgt ccacaattta tctttttctgc   15420 tgttagtgga catttgagta gtttgcagtt ttggacaatt tttttttttt ttgagttgga   15480
gtctcactct gttgcccagg ctggagtgca gtgtcacgat ttcggatcac tgcaacctcc   15540
acctcctggg ttcaaggggt tctcgtgcct cagcttccca agtagctggg atgacaggag   15600
tgtaccatca tgccctgcta atttctgtat ttttagtagg gatggggttt caccatgtta   15660
gccaggctgg tctcgaactc ctgatctcaa gtgatgcgcc tacctcggcc tcccaaagtg   15720
ctgggattac aggcgtgagc cactgcacct ggctgttttg cactattatg catgtggctg   15780
ctatgagcat tctagtccct gtctttgggt gtctctgccc tgtttctatt ggtctgaatt   15840
```

```
gggggtggca ttgctgggtg ctgcctcatt cttttccagg ccctcaggat tctctggggg   15900
ctgggcagct gggctgtggc cctcgtgtcg ctcatccaac cctgctgccg ggcttgtccc   15960
tgtaacttgc ctgcccttgc tcgtcctcca ggtgtgtctg acgctgaccg ccaagcgcat   16020
ggcccggaag aactgcctgg tgaagaacct ggaggctgta gaaaccctgg gctccacgtc   16080
caccatctgc tcagataaga cagggaccct cactcagaac cgcatgacag tcgcccacat   16140
gtggtttgac aaccagatcc acgaggctga caccactgag gaccagtcag gtgagcgcag   16200
gccccgggtg aggaccatgg gggcctggct ccaggagtcc ctggccctca cacatgcctc   16260
ccccagggac ctcatttgac aagagttcgc acacctgggt ggccctgtct cacatcgctg   16320
ggctctgcaa tcgcgctgtc ttcaaggggtg gtcaggacaa catccctgtg ctcaaggtgg   16380
gttcagctac tggcctcacc tcggccctgc ctgtgtcctc ccctcagctg tccctgttct   16440
gacaacccct tctccttgca gagggatgtg gctggggatg cgtctgagtc tgccctgctc   16500
aagtgcatcg agctgtcctc tggctccgtg aagctgatgc gtgaacgcaa caagaaagtg   16560
gctgagattc ccttcaattc caccaacaaa taccaggtac tctgggcttt ccgggagagc   16620
cagcctggac ctcaggttcc ttatgacgcc tgtaaagagg tgtcatagag ccttgatttt   16680
cccgtctgta aaatgggaat gataataccc gcctggtggg gagaggaaca gggagagctt   16740
gagagtggga gccggatctc tgttggagtg agacgctgag gagtaaagat cttcctgcag   16800
gccaggcgcg gtggctcaca cctttaacac cagaactttg ggaggctgag gtgggggat   16860 cacttgaggc caggagttcg agacgagcct gggcaagatg gcaaaacccc atctgtacga   16920
aatttttttt ttaattagcc aggtgtggtg gtatgtgcct gtggtctcag cgatttggga   16980
gtctgaggca ggaggattgc ctgagccggg gaggttgggg ctgcagagag cctacatcac   17040
gcactgtact ccagcctggg tgacagagca agaccctgac tcaaaaaaaa aaaaaagtt   17100 ttcctacagc agagagtggg aacaagcagg agacctcttg gggcagagca gcaacttaa   17160 attattcagc aaactttttt tttttttgag acagagtttc gctctgtcac ccaggctgga   17220
gtgcagtggc gcgatctcag ctcactgcaa gctccacctc ccgggttcac accattctcc   17280
tgcctcagcc tccagaatag ctgggactac aggcgcccgc caccatgccc agctaatttt   17340
ttgtattttt agtagagacg ggggtttcacc gtgttagcca ggatggtctc gatctcctga   17400
cctcgtgatc tgcccgcctc agcctcccaa agtgctggga ttacaggcat gagccaccgc   17460
gcccggcctc agtaaacttt tttttgagat ggagtcttgc tctgtcgccc aggctaaaag   17520
gcagtggtgt gatcttggct cactgcaacc tctgtctctg ggttcaagtg attctcatat   17580
ctcagcctcc cgagtagctg gaattagagg cgtgcaccac cacacccagc tagttttgt   17640 atttttagta ttgatggggt ttcatcatgt tggccaggct ggtcttgaac tcctgacctc   17700
aagtgatcca cccacctcgg cctcccaaag tgctgggatt acaggcataa gccatcatgc   17760
ccggcccatt cagtatacat tttttgacca gccaccacat gttaggccct gttttggggtg   17820 ctgggtgtac acacagtagt gagtgacatg gtgaagtcac ccctctctga gacttacgct   17880
ctggttctag aagacagaca ataacaaagg catgaggagg taatcgtagt ggttgtggtg   17940
ctgagggagg gaaccctgca ggtgtctggg ggaagagcgc tccggtagca ggcacagcct   18000
gtgcaaaggc ccagaggcgg gagtgtgctg acgcatctga acaccagcca gccagccagt   18060 gcagagggc tgggagccag gggagcgtgg gggggtggtg ggtgctggcc agatcctgtc   18120
aggccccacg ggcatggaga ggacttggct gtgactctga ggagcacaca agcctccagg   18180
```

```
gggctctcag ccaaagagag acaggagttg actcagagct tttaaaataa ctttattaag   18240
atataattaa cataccatag ctcgtccctc taagtgtata atttaatagt tttagtatat   18300
tcgcagatat aggcagccat ccacatagtc aattttagag cattttcatc acctccaaaa   18360
agaaacccca catctctcag ctgtcacccg cccctcctc cccgacactc ccagccctaa    18420
gcaaccacta acctactttc tgtccgtatg gttttgccta ttctggacat ttcataaaaa   18480
tggaagcata cagctgggtg tggtggctca cgcctgtaat cccagcactt tgggagaccg   18540
aggcaggagg atcgcttgaa ctcaggagat ggagaccagc gtgggcaaca tagggagagc   18600
atgtctctat aaaaaattag ccaggcatgg tggtgtggac ctgtggtccc agctacgtgg   18660
gagaccgaag cgggaggatc gcatgagcct gggagatcaa ggctgcagtg agctgtgatc   18720
tcgccactgt tctccagcct gggtgacaga gtgagaccct gtcttaaaaa aaaaaaacag   18780
ggtgggagga ggggagcaca gacgtggtgg cttatgcctg ttatcccagc actttgagag   18840
gccgatgagg gcagatcact tgaggccagg agttcaagac cagcctggcc aacatggcaa   18900
aatcccgtct ctactaaaaa tacaaaagtt agctgggtgt ggtggtggtg cctgtaatcc   18960
caagctactc cggaggctga ggcaggagaa ttgcttgaac ccaggaggtg gaggttgcag   19020
tgagctgaga tcgtgccact gcactccagc ctgggcaaca gagcgagact ctgtctcaaa   19080
aaaaaaagaa aaagaaaaa aagaaaaaga aaagaaata tatatccatg acatagacag     19140
agcggacagg aatgagcaga ggtctctgtg agagagtgtg gggagccct ggtgtgggcc    19200 tatcctggca cccgtggctc tggacagggg acaggatggg gcaggagct cctggtgtc     19260 tgcgtggctc aggcacgcca ccctctgatc ggtccccagc tctccatcca tgagaccgag   19320
gaccccaacg acaaccgata cctgctggtg atgaagggtg cccccgagcg catcctggac   19380
cgctgctcca ccatcctgct acagggcaag gagcagcctc tggacgagga aatgaaggag   19440
gccttccaga atgcctacct tgagctcggt ggcctgggcg agcgcgtgct tggtgcgagg   19500
ctgccgggcg ggctctgggg tccctggagg gcaaggaggg ttgtgatgct gcccaaagcc   19560
tgtctcagcc cagggcctcc cagaatatac tgtaaatgaa tgaatgaatg aatgaatgga   19620
tggatgagag gggaaggtat cctaggaaat gaatgctgac tggccgtctt gctgatgggg   19680
agatggaatg cgggcgatgc agacatctag gggcatgggg cggaggttcc gaggctggga   19740
ccctcacacc ccaaccctc cctgccacta ggtttctgcc attattacct gcccgaggag    19800
cagttcccca agggctttgc cttcgactgt gatgacgtga acttcaccac ggacaacctc   19860
tgctttgtgg gcctcatgtc catgatcgac ccacccgggg cagccgtccc tgacgcggtg   19920
ggcaagtgtc gcagcgcagg catcaaggtg tggcttgggg tggctggggg aggcaaagcc   19980
aggcgtgggg cgggagaggc catccctaaa aaacaatgcc tgcaggtcat catggtcacc   20040
ggcgatcacc ccatcacggc caaggccatt gccaagggtg tgggcatcat ctctgagggc   20100
aacgagactg tggaggacat cgccgcccgg ctcaacattc ccgtcagcca ggttaacccc   20160
cggtgagcca cccatcccag ccaggccct ggacatccct ctagggtgtt gacacagggg    20220
gaccgcttcc ccccaacctc cctctgcact gcctgtccca ttctttctgg gactcctcca   20280
tggaccaggc cctgggtctg gccctccctc cggtgtgggg acattgcagc cacagaggta   20340
gccaggcata ggtttgcatc ccagccttta ttttattttta tttatttatt tatgttttg   20400 agatggagtc ttgctctgtc gcccaggctg gagtgcagtg gggcaacctc agctcactgc   20460
agcctccgcc tcccgggttc aagcaattat ctgcctcagc ctcttgagta gctgggatta   20520 cagggggccct ccaccatgcc ccgctaattt tttttttttt ttttgtatt tttagtagag   20580
```

```
acgggggttt cactatgttg gccaggctgg tctcgaactc ctgacctcag gtggtccacc    20640
tgccttggcc tcccaaagtg ctgggattac aggcgtgagc cactgcgccc ggcctgcatt    20700
ccagcttata ccgctcacaa gctgtgtgac attgggcaag tcctttagca tccatgaact    20760
tcagtttgcc catctctaaa atgggctact aataattcct atctcagagg attcagtaga    20820
atccagtact tctgtgtctg tctctctttt ttcctgtctg tctgtcattg tctctctttt    20880
ctgttctgtt tttctgactt cttcaacttt cccatcctca tacctatctc tgactctgcc    20940
ttccttcagc ttgtccattt atctccgttc ctctgaatcc actgtgtctt ggctgggcgc    21000
agtggctcac gcctgtaatc ccagcatttt gggaggccga ggtgggtgga tcacttgagg    21060
tcaggagttc gagagcagcc tggccaacat ggcaaaaccc catctgcact aaaaattaaa    21120
aaaaaattag ccaggcgtgg tggtgggcac ctgtaatcct atctactagg gaggctgaga    21180
caggaaaatc acttgaaccc aagaagcaaa ggttgcagtg agccgagatt gcgccactgc    21240
actccagctt gggtgacaga gcgagactcc atctcaaaaa taaataaata aataataaat    21300
aaataaataa ataaatccac tgccccaaag tccttcctca ggtctgcccg cacgccctgc    21360
tgcagtagcc cccttctccc ctgcttctcc cagaggcctc ttcccccagc ccctggtcct    21420
ctggctctcc tggttgtggg gctggcccct ctgtttctct gtctttcagg gatcactttg    21480
ccactcctca cacccctga cctcagccat cgctctctct gctcttccca gggatgccaa    21540
ggcctgcgtg atccacggca ccgacctcaa ggacttcacc tccgagcaaa tcgacgagat    21600
cctgcagaat cacaccgaga tcgtcttcgc ccgcacatcc ccccagcaga agctcatcat    21660
tgtggagggc tgtcagagac aggtgggctg cgctcccgca gaggagggga cggggccttg    21720
actcctgggt cctcactgag gccggggcct ggtttcctgg gtctgaggga ggaggggctg    21780
ggggtctgga cccctgggtc tgagagagga gggtctgggg gcctggactc ctgggtctga    21840
gggaggaggg ggctggggac ctggaccctt gggtctgagg gaggggcct ggacttctgg    21900
gtatgaggga agagggata ggggcctgaa ctcctgggtc tgagggagga gggggtgggg    21960
gcctggaccc ttgggtctga gggaggaggg gctgggggcc tggaccctg gtctgagg    22020
aggagggtct gggggcctgg actgctgagt ctgaggggaga aggaggctgg gggcctggac    22080
ctctgggtct gagggaggag ggtctggggg tctgaccccc tgggtctgag ggaggaaggt    22140
ctggaggcct gaactcctag gtctgagggg aagaggaggt tggggacctg aacttctagg    22200
tctgaaggag gaggggctg gggtcctggg cttctggatc tgagggaggg gactctgggg    22260
actggcctct gggtgtcatc cttaccctct ctccctccag ggtgcaattg tggctgtgac    22320
cggggatggt gtgaacgact ccccccgctct gaagaaggcc gacattgggg tggccatggg    22380
catcgctggc tctgacgtct ccaagcaggc agctgacatg atcctgctgg acgacaactt    22440
tgcctccatc gtcacagggg tggaggaggg tgagttggcc aggggtggcc ctggagacca    22500
gggtcactac cggaggcctg agaccagcaa ggggaactgg ccaggctgc aggggatgt    22560
gtggcagaga ccacaggccc cctggccctg gaggagcctg agcctgtcct tttctgtctt    22620
cctcccctgt ggggtcggga gctcccctgg gcaggactga gctgacacac ttcagggtcc    22680
ctgcgtcatc cagcccaggc ccatctggt gggtgaagct gacttggagg cttttttaaag    22740
atattctcag ccaggggcgg cagccacgcc tgtaatccca gcactttgga aggctgaagc    22800
aggcagatca tgaggtcaga agatcgagac catcctggct aacatggtga aaccccgtct    22860
ctactaaaaa tacaaaaaat tagccgggca ttgtggcggt tgcctgtagt cccagctact    22920
```

```
cgggaggctg aggcaggaga attgcttgaa cccaggaggt ggaggttgca gtgagctgag   22980
attgcgccac agcactccag cctgggggac agagcgagac tccgtctcaa aaaaaaaaaa   23040
aaattctcaa gcccaaccag ggggaagcca gggaccctgg gggatacccc ctctgccagc   23100
ctgggctggg ggtcaaggga gcttcccaga gtggacaggg atggctgagc caagtcaggg   23160
gccatgctgt gacgtccaca tagactagtg ccagggagtc gcaggcagag gaaccggtac   23220
acaggcaagg cggtgtgagg ggctgggtct gaggctggtg ctgctgagcc gacaggcacc   23280
acctcctgac aggcccagac aaggccacag aagggttggt tcacattcag atttattttg   23340
atcatcaaat taattcatga taatcataga caaatgcaga aaagcattca ggaaaaaagt   23400
agaatcaccc gtaacctcgc catccagaaa taatcacggt tcatgccttg gtggattttc   23460
ttccaatttc tctctcctat ttgaaatgtc tctggtgtaa aaagtagttc atggtaaaag   23520
agaattcaaa cggcaaagcc gagcccagag taacagatta aatgtcctca gcccttgtct   23580
cctatatccc agaggaaacc atggttaaca ccttcttatc tcccaagaga catctttttt   23640
tgggggctgg gggcggggat agagtctcaa tctgtcaccc aggatggagt gcagtggcac   23700
aatcacggct aactgcagcc tccacctccg ggacttaatc gatcctcctg cctcaggccc   23760
ctaagtagct gagactacag gtatgcacca tcacacctgg ctgatttta agattttgta   23820
gagatggggt ttcgccatgt tgcccagact agtctttctt ttttttgag acagagtctt   23880
gctctgtcac ccaggctgga gtacaggcat gcaatctcgg cttactgtag cctccacctc   23940
ctgggttcaa gcaattctcc tgcttcagcc tcccgagtag ctagaattac aggtgcatgc   24000
caccacacca ggctaatttt tgtatttta gtagagatgg ggtttcacca tgttagccag   24060
gctggtcttg atctcctgac ctgaagtgat ccccgcacct tggcctccca aagtgctggg   24120
attgcagggg tgagccacct cgcccagcga ggtcttcaac tcctgggctc aagcaatcct   24180
cccaccttgg cctcccaatt tgctgggatt acaggcatga gccaccacgc ctggcctccc   24240
caagacatct atgcatacac agtacacaca ctgtctcaga tacagccgtc tgctccttcc   24300
gaatcttgtg catcatgctg gaagcctggg aggcagctgt gagcagagca gacaccatcc   24360
ctgttctcac agggctggag agacagcctt aaacaagtta acagatatgt aattacaaat   24420
tgtgatatat gccccgaaga aagcaggccg ctgtgataga taatagtgag ggtcctgccc   24480
agatggggtg gacagggaag gcctctctga agtgagggaa gaaataccta acttccgtca   24540
ggggccaggc acggggctc acgcctgtaa tcccagcact ttgggagacc aaggcgggag   24600
gatcgcttga gcccaggagt tcaagacctg cctgtacaac aaattaagac ctcaaagatc   24660
aaaaaatttt aaaaattagc agggcgtggt gttgcacacc tgtagtctca gagacttggg   24720
gggctgaggc aggaggatca cttgagcctg ggtggtcgag gctgccatga accatgatgg   24780
tgccactgca ctccagcctg ggatagagcg agatccgaga ccctgtctca aacaaacaaa   24840
caaaataact tccaacgggg gcattccaga tatacccaaa agtaaagcaa aggcacagtg   24900
ggccctgcg cctccatccc acctgcagcg gcagtcagcg cacggcacac cttgtttctt   24960
ccccaccacc tggaacacac actggattat gctgatgcac atttgtcacc atttcatcca   25020
taaatagttt aggatgagaa acccctagtt tgtggagaag agcacaatgc agggaacgag   25080
aatatcaggt gggagcggcc caggcccta ttgctatgca agagacatca aagcaatcaa   25140
agaagccaca ccacaggcag cctgcttcac cttcccttcc ctccctccct cccttcctcc   25200
ctccctccgt cctgcctgc ctgccttcct tccttctttc cttccttcct tcttccttc   25260
cttccttcct tccttccttc cttccttcct tccccttcct tccttccttc cccctcccct   25320
```

```
cccctcccct ttttttgatg gagtcttgct ctgttgccag gctggagtgc agtggcgtga   25380
tgttggctca ctgcaacctc cacctcccag cttcaagcga ttcttctgcc tcagcttccc   25440
acatagctgg aactacaggc acacaccacc actcccagct aatttttgt gttttagtag    25500 agatggggtt tcaccatgtt ggccaggata gtctcgatct cctgacctcg tgatccaccc   25560
gcctcagcct cccaaagtgc tgggattaca ggtgtttgcc accgtgcccg cctgttcttt   25620
cttaatgatt gacctcattg ttcatgggct aatctttta cttatttatt tatttagaga    25680
caaggtctca ctctgttgcc caggctggag cgcagtgctg caatcatcag tcactgcaac   25740
ctcgacctcc tcaagtgatc ctcccacctc agcctcccaa gtagctgcga ccacaggctc   25800
gagccaccgt gcctgactaa tgtttatttt attttatttt attttttga gatggagtct    25860 tgctctgttg cccaggctgg agtgcaatgg cacaattgcg gctcactgca acgtctgcct   25920
ctgaggttca aatgattctc ctgcctcagc ctcccaagta gctggggtta caggtgccca   25980
ccaccacgcc cagctaattt ttgtattttt agtagagatg gggtttcatc atgttggcca   26040
ggctggtctt gaactcttga tctcaggcaa tcctcctgct tcggtctccc aaagtgttgg   26100
gattacaggt gtgagcccca cgcctggcc tggattaatc tttattttgt ttactttaga    26160
caacctgtac tggttgaata tttattgaga tatggcatgc atacagtgag ttgggcatat   26220
tatatctcat aaaatattc aaccagacag ggtgtataaa tttttacaca tgtacacagc    26280
catgcaacca ccagacccca gtcaagatag aaaaccattc cagcccccca tttaggtttt   26340
gtctgctctc ttccagtcta tatccctcct cctagacata accattatcc tgactttag    26400 cccagagacg ggtgctgagc ctgctccagt tggagttgga tgctaagaat gcttttgtgt   26460
ctggctcgtg tcactcagca cgggatccaa ggtccagctg tggagttgtg tccgtagctc   26520
gccccttctt gctgtgtagt atttgactgc atggatgtac cgtggtttat tcatccctca   26580
cctgttgatg gacatggggt tgactctggc ttttggctct gatgagtggt gctatggtga   26640
acattctcgt acttgctttt cgctgggcat aaacagtcct cctctctttt gggtataaaa   26700
cctaggagtc ggattactcg gtcggtgggg tgggggatgt ttgatagcaa ctccgaaacc   26760
atcttccaaa gtggttattt caagaatgtt tccacaaagg cgatgtggtt ggatgtttat   26820
gtggaaaggt aggtgggtga ggggccaggt gtggagactt atgcctgtaa tcccagcact   26880
tcgggaggct gagatggaat cacagcccag aaattagaca agcctaggaa aagtggtgag   26940
actctgtctc tactaaaaat acaaaaatta gctggacgtg gtggcgcgtg actgtagtct   27000
cagctacatg ggaggctgag gcaggaggat cacttgagcc tggagtcga ggttgcagtg    27060 agccgtgatc atgccactgc actgcagcct gggcaacaga gtgagaccct gtcccaaaaa   27120
gaaaataatg gtgggtgggc tgggggtag aaaaggacgc tggacaggcc gggcgcggtg    27180
gctcacgcct gtaatcccag cacttcagga ggccgaggag ggcagatcac gaggtcagga   27240
gattgagacc atgcaggcta acacagtgaa accccgtctc taataaaaat acaaaaaaat   27300
tagccgggcg tggtggcagg tgcctgtagt gccagctact cgggaggctg aggcaggaga   27360
atggcgtgaa cccgggaggc ggagcctgca gtgagccgag atcgcaccac tgcactccag   27420
cctgggcaac acagcgagac tctgtctcaa aaaaaaaaa aaaaaaaaa aggacgttgg    27480 atgagggcag aggaggggca gagggagtgg ggctccctgg catgggcgcc tgctctgagc   27540
ctgcctgtgc cacaggccgc ctgatcttcg acaacctaaa gaagtccatt gcctacaccc   27600
tgaccagcaa tatcccggag atcacgccct tcctgctgtt catcatggcc aacatcccgc   27660
```

```
tgcccctggg caccatcacc atcctctgca tcgatctggg cactgacatg gtgagccctg    27720
gcagccaccc ttggggccca ggagggtgga gtcctcccct ctccggctca cccggcctcc    27780
tccgcctagg tccctgccat ctcactggcg tacgaggctg ccgaaagcga catcatgaag    27840
agacagccca ggaacccgcg gacggacaaa ttggtcaatg agagactcat cagcatggcc    27900
tacgggcaga ttggtgaggc accggggact ccatctcctt accacccagt gccgggccta    27960
gagcagtgcc tggcccaccg tgggtgcttg ggaccctggc attgactcag gggagcagac    28020
gtgggcagga ccaaccagtg agctatctgt ggggggggtc tgcaccccat ccttctccac    28080
ctcctcctct ctgctgttga tgtgtgcgga tccccagagg agtggagcag ccacccttgg    28140
gggctgtccc agcaagcaga gacttcatgg cagtggttcc aggcccaggg aggtcattcc    28200
tgcgtaggga gctcaagctg gggatccccc aagaattcat gatgtttagg tggcctaggt    28260
caggtgagag aggggctcca ggttatccct ctgggagagc cctctctcca aagcccctgt    28320
cccaggtggc ccacccatct cagggcctca ccaccaagtg agacctcagg tcaccctctg    28380
ggaaccaatg tccagataac agggccagga gggcatactc ccctctccaa ggaggcctcc    28440
gggccctctg aggtgccctg ggttggctgc tggcccaat ctgagcctct cctcggcttc     28500
ctctctcctc cttccaggaa tgatccaggc tctcggtggc ttcttctctt actttgtgat    28560
cctggcagaa aatggcttct tgcccggcaa cctggtgggc atccggctga actgggatga    28620
ccgcaccgtc aatgacctgg aagacagtta cgggcagcag tgggtgagta gggcagggtg    28680
ctgtgtctct gcccaccgta agatccccgg ggtgagctgt tccagccatg catggccact    28740
tcctacgatg gcccctcag tctcccatgg cagcatcaag gcctttgctg ggcacctggg     28800
gcttcctgga tgcccttggc ccagcccatc tggagccttg tgtcccactg ctggagctct    28860
ctgccctgcc aggccttctt ccccacctct gtctgtccct tcaaagccca gttgctgtct    28920
gtcctccttg ggaggcccac agggtcctta tcctcctccc tggcccctgg tggatggtga    28980
gatcaccatt aacctttctt cttccttgta cgtctcctga ctcctccctc gggactatga    29040
gcccgcagaa ggaagacaca cctgaggccc tgaggacccc atgcaggatg gggcggggca    29100
aagagcaccg gaacgtcggg gtggcggcta ggctgcagt gccactaact gacgtcccgt     29160
gccctggtca ccgctcctgc agacatacga gcagaggaag gtggtggagt tcacctgcca    29220 cacgccttc tttgtgagca tcgttgtcgt ccagtgggcc gatctgatca tctgcaagac     29280
ccggaggaac tcggtcttcc agcagggcat gaagtgaggg ccggggcac atggtgactg     29340 gacagccatc tgtcctgtcc gagtgtctgt ctgtctgtgt acttcctctt gtgtccttgc    29400
tttggttttt tgttgttttg ttgaggcagg gtctcactct gtcacccaga ctggagttca    29460
gtggtgtaat catagctcac tgcagcctcg acctcctggg ctcaagtgac ccacccacct    29520
cagcctcctg agtagctgag actacaggtg tgcaccatca tatatggcta attttttattt    29580 atttatttag agacagagtc ttgctctgtt gcccaggctg gagtgcagtg gcacaatctt    29640
ggctcactgc aacctccgcc tcccgggttc aagcgattct catgcctcag cctcccaagt    29700
agctgggatt acaggtacgc accaccaggc tcggctaatt tttcgtattt ttagtagagt    29760
ttcaccatgt tgcccaggct ggtctcaaac tcctgagctc aggcaatctt cctgcctcag    29820
cctcccagag tgctaggatt acaggtgtga gccaccatgc ccagcccatt tgggttttg     29880 ccactgcact gattttctct caaggggtcc tgtgtgtcct agattctctc tcagcctctg    29940
tgtgtgtggt ggaggtgccc ctggcctttt ctttttatac cagtgcctct ctgtgtctgt    30000
ccctgtctct gtgtctgttt ctgtccctgt ctctgtgtct gtccctgtgt ctgtctctct    30060
```

```
gtctgtccct gtctgtctct gtgtctgtcc ctgtctctgt gtctgtccct gtcttttgtc    30120
tctttctgtg tcaccatcgc tctgcctcta tctttgtctc tctctgtcgg ggcatgtctc    30180
cccatctctg tctctcccta tgtctctgcc tctctgtctc tgtgtctgtg ctgctgtctc    30240
tgggtgtctg cactgtgcct ccccctgtct ctgcggggtg gcaggtgcag ggtgggtgct    30300
ctctgggccc agccctgccc ttctgtgcct ccaggaacaa gatcctgatc ttcgggctgt    30360
ttgaggagac ggccctggct gccttcctgt cctactgccc cggcatggac gtggccctgc    30420
gcatgtaccc tctcaagtga gtgccccgct gcccccagcc ctgcccacac cagcgcctgc    30480
catggagcct tcccttagac tcagcctgaa cctcaggccc cacctcccct ggtgtcccca    30540
ctgcagtccc cattctgatg cccccgagcc tccccatag gctgctccca ccacggatta    30600
ctccgaagac cccaggcccc agcccgccc agggcaccct ccacctgtga gcacgaagga    30660
tcctgggaga ctgcccctct gcgtccctc cagtcccctg aaactctgcc tctcgttagg    30720
gccccgcact caagccctcc tgctctcccc tctgcaggcc cagctggtgg ttctgtgcct    30780
tcccctacag tttcctcatc ttcgtctacg acgaaatccg caaactcatc ctgcgcagga    30840 acccagggg tgagggagct cggcaaggca gccgagggg gcgggggca gcagggtctc    30900 aggcagctgg tcccaggctc ccctcgccct gctggatggc tctgccacct ggttcccact    30960
cttctctctc ttcccatctc tccgggcacc cactctgtct tctcacgggt ctctgtctgt    31020
gtggtttcct tgtctctctc cctctctgtc cctctctctg ctgggcggct cgccttgcct    31080
gtctctctcc atctcttact ctgtctcttt ctttccttct ttgtctctcc aggttgggtg    31140
gagaaggaaa cctactactg acctcagccc caccacatcg cccatctctt ccccgtcccc    31200
caggcccagg accgccctg tcagtccccc caattttgta ttctgggggg aggagccctc    31260
tcttcctgtg gccccacctt ggcccccacc ccctccacta tctcctgccg ccccccactct   31320 ggctggcttc tctcccctgc cccaaacctc tctcctctct cttttctgtg tcagtttctc    31380
tccctctcct caccctcta tccattcctc ccgccccagc cacctccctg ggctcttttt    31440 tactccccttt cagccccccg gctgatgcca tctctggttc tggacaatta tcaaatatat   31500
cagtggggag agagaagcgg tgtgtgtgtt gtgcctgctt tccagacggg gactgcggct    31560
gggacagcat ccctctgtt ggggcgcgct gccaggcgac tctcgaaact gcaggaactt    31620
agcctggcac tggcttggaa gtcacggaat ctcagagcca tctaatcacg gagttttcaa    31680
ctccacgaaa gtcagagcag cttgaattca ccaggcgatg gcattgtgga atcagaacag    31740
gggagaggga gggaagcaga cgtgggatgg tgactgggag cctctcctat aggagtagga    31800
cccaggggac acaatgacga tgatgatggt gatgacagtg attcactgag tgcctgctat    31860
gtgctctgcc cacttctaag tgtgcattaa atgtgcacag agaagaag tgatttgcac    31920 acagctaaga agagacaaat ctgggatttg aaccaaggct gtccaaagtt ctaggtcact    31980
acgctattct ctcttttat tgagataaac tttcatacag tgaagtgcac gcatcttaag    32040
ggtatagctc aatgatttta aaaattgcat ctgcaggcca agcgcggtgg ctcccgcctg    32100
taatcccagc actttg                                                    32116
```

<210> SEQ ID NO 2
<211> LENGTH: 3551
<212> TYPE: DNA
<213> ORGANISM: Homo sapiens

<400> SEQUENCE: 2

```
cgcgcgcacc taccgaggcg cgggcgctgc agaggctccc agcccaagcc tgagcctgag        60
cccgccccga ggtccccgcc ccgcccgcct ggctctctcg ccgcggagcc gccaagatgg       120
gggacaagaa agatgacaag gactcaccca agaagaacaa gggcaaggag cgccgggacc       180
tggatgacct caagaaggag gtggctatga cagagcacaa gatgtcagtg aagaggtct        240 gccggaaata caacacagac tgtgtgcagg gtttgaccca cagcaaagcc caggagatcc       300
tggcccggga tgggcctaac gcactcacgc caccgcctac cacccagag tgggtcaagt        360 tttgccggca gctcttcggg ggcttctcca tcctgctgtg gatcggggct atcctctgct       420
tcctggccta cggtatccag gcgggcaccg aggacgaccc ctctggtgac aacctgtacc       480
tgggcatcgt gctggcggcc gtggtgatca tcactggctg cttctcctac taccaggagg       540
ccaagagctc caagatcatg gagtccttca gaacatggt gccccagcaa gccctggtga       600
tccgggaagg tgagaagatg caggtgaacg ctgaggaggg ggtggtcggg gacctggtgg       660
agatcaaggg tggagaccga gtgccagctg acctgcggat catctcagcc cacggctgca       720
aggtggacaa ctcctcctg actggcgaat ccgagcccca gactcgctct cccgactgca       780
cgcacgacaa ccccttggag actcggaaca tcaccttctt ttccaccaac tgtgtggaag       840
gcacggctcg gggcgtggtg gtggccacgg gcgaccgcac tgtcatgggc cgtatcgcca       900
ccctggcatc agggctggag gtgggcaaga cgcccatcgc catcgagatt gagcacttca       960
tccagctcat caccggcgtg gctgtcttcc tgggtgtctc cttcttcatc ctctccctca      1020
ttctcggata cacctggctt gaggctgtca tcttcctcat cggcatcatc gtggccaatg      1080
tcccagaggg tctgctggcc actgtcactg tgtgtctgac gctgaccgcc aagcgcatgg      1140
cccggaagaa ctgcctggtg aagaacctgg aggctgtaga accctgggc tccacgtcca       1200 ccatctgctc agataagaca gggacccctca ctcagaaccg catgcacagtc gcccacatgt      1260 ggtttgacaa ccagatccac gaggctgaca ccactgagga ccagtcaggg acctcatttg      1320
acaagagttc gcacacctgg gtggcccgt ctcacatcgc tgggctctgc aatcgcgctg       1380
tcttcaaggg tggtcaggac aacatccctg tgctcaagag ggatgtggct ggggatgcgt      1440
ctgagtctgc cctgctcaag tgcatcgagc tgtcctctgg ctccgtgaag ctgatgcgtg      1500
aacgcaacaa gaaagtggct gagattccct tcaattccac caacaaatac cagctctcca      1560
tccatgagac cgaggacccc aacgacaacc gatacctgct ggtgatgaag ggtgcccccg      1620
agcgcatcct ggaccgctgc tccaccatcc tgctacaggg caaggagcag cctctggacg      1680
aggaaatgaa ggaggccttc cagaatgcct accttgagct cggtggcctg ggcgagcgcg      1740
tgcttggttt ctgccattat tacctgcccg aggagcagtt ccccaagggc tttgccttcg      1800
actgtgatga cgtgaacttc accacggaca acctctgctt tgtgggcctc atgtccatga      1860
tcgacccacc ccgggcagcc gtccctgacg cggtgggcaa gtgtcgcagc gcaggcatca      1920
aggtcatcat ggtcaccggc gataccccca tcacggccaa ggccattgcc aagggtgtgg      1980
gcatcatctc tgagggcaac gagactgtgg aggacatcgc cgcccggctc aacattcccg      2040
tcagccaggt taaccccgg gatgccaagg cctgcgtgat ccacggcacc gacctcaagg      2100
acttcacctc cgagcaaatc gacgagatcc tgcagaatca caccgagatc gtcttcgccc      2160
gcacatcccc ccagcagaag ctcatcattg tggagggctg tcagagacag ggtgcaattg      2220
tggctgtgac cggggatggt gtgaacgact cccccgctct gaagaaggcc gacattgggg      2280
tggccatggg catcgctggc tctgacgtct ccaagcagga agctgacatg atcctgctgg      2340
acgacaactt tgcctccatc gtcacagggg tggaggaggg ccgcctgatc ttcgacaacc      2400
```

-continued

```
taaagaagtc cattgcctac accctgacca gcaatatccc ggagatcacg cccttcctgc    2460
tgttcatcat ggccaacatc ccgctgcccc tgggcaccat caccatcctc tgcatcgatc    2520
tgggcactga catggtccct gccatctcac tggcgtacga ggctgccgaa agcgacatca    2580
tgaagagaca gcccaggaac ccgcggacgg acaaattggt caatgagaga ctcatcagca    2640
tggcctacgg gcagattgga atgatccagg ctctcggtgg cttcttctct tactttgtga    2700
tcctggcaga aaatggcttc ttgcccggca acctggtggg catccggctg aactgggatg    2760
accgcaccgt caatgacctg gaagacagtt acgggcagca gtggacatac gagcagagga    2820
aggtggtgga gttcacctgc cacacggcct tctttgtgag catcgttgtc gtccagtggg    2880
ccgatctgat catctgcaag acccggagga actcggtctt ccagcagggc atgaagaaca    2940
agatcctgat cttcgggctg tttgaggaga cggccctggc tgccttcctg tcctactgcc    3000
ccggcatgga cgtggccctg cgcatgtacc ctctcaagcc cagctggtgg ttctgtgcct    3060 tccctacag tttcctcatc ttcgtctacg acgaaatccg caaactcatc ctgcgcagga    3120 acccagggg ttgggtggag aaggaaacct actactgacc tcagccccac cacatcgccc    3180
atctcttccc cgtcccgcag gcccaggacc gcccctgtca gtccccccaa ttttgtattc    3240 tgggggagg agccctctct tcctgtggcc ccaccttggc cccacccccc tccactatct    3300
cctgccgccc ccactctggc tggcttctct ccctgcccc aaacctctct cctctctctt    3360
ttctgtgtca gtttctctcc ctctcctcac ccctctatcc attcctcccg ccccagccac    3420
ctccctgggc tcttttttac tcccttcag ccccccggct gatgccatct ctggttctgg    3480
acaattatca aatatatcag tggggagaga gaaaaaaaaa aaaaaaaaa aaaaaaaaaa    3540 aaaaaaaaaa a                                                          3551
```

<210> SEQ ID NO 3
<211> LENGTH: 1013
<212> TYPE: PRT
<213> ORGANISM: Homo sapiens

<400> SEQUENCE: 3

```
Met Gly Asp Lys Lys Asp Asp Lys Asp Ser Pro Lys Lys Asn Lys Gly
1               5                   10                  15

Lys Glu Arg Arg Asp Leu Asp Asp Leu Lys Lys Glu Val Ala Met Thr
            20                  25                  30

Glu His Lys Met Ser Val Glu Glu Val Cys Arg Lys Tyr Asn Thr Asp
        35                  40                  45

Cys Val Gln Gly Leu Thr His Ser Lys Ala Gln Glu Ile Leu Ala Arg
    50                  55                  60

Asp Gly Pro Asn Ala Leu Thr Pro Pro Thr Thr Pro Glu Trp Val
65                  70                  75                  80

Lys Phe Cys Arg Gln Leu Phe Gly Gly Phe Ser Ile Leu Leu Trp Ile
                85                  90                  95

Gly Ala Ile Leu Cys Phe Leu Ala Tyr Gly Ile Gln Ala Gly Thr Glu
            100                 105                 110

Asp Asp Pro Ser Gly Asp Asn Leu Tyr Leu Gly Ile Val Leu Ala Ala
        115                 120                 125

Val Val Ile Ile Thr Gly Cys Phe Ser Tyr Tyr Gln Glu Ala Lys Ser
    130                 135                 140

Ser Lys Ile Met Glu Ser Phe Lys Asn Met Val Pro Gln Gln Ala Leu
145                 150                 155                 160
```

```
Val Ile Arg Glu Gly Glu Lys Met Gln Val Asn Ala Glu Glu Val Val
            165                 170                 175

Val Gly Asp Leu Val Glu Ile Lys Gly Gly Asp Arg Val Pro Ala Asp
            180                 185                 190

Leu Arg Ile Ile Ser Ala His Gly Cys Lys Val Asp Asn Ser Ser Leu
            195                 200                 205

Thr Gly Glu Ser Glu Pro Gln Thr Arg Ser Pro Asp Cys Thr His Asp
            210                 215                 220

Asn Pro Leu Glu Thr Arg Asn Ile Thr Phe Phe Ser Thr Asn Cys Val
225                 230                 235                 240

Glu Gly Thr Ala Arg Gly Val Val Ala Thr Gly Asp Arg Thr Val
                245                 250                 255

Met Gly Arg Ile Ala Thr Leu Ala Ser Gly Leu Glu Val Gly Lys Thr
            260                 265                 270

Pro Ile Ala Ile Glu Ile Glu His Phe Ile Gln Leu Ile Thr Gly Val
            275                 280                 285

Ala Val Phe Leu Gly Val Ser Phe Phe Ile Leu Ser Leu Ile Leu Gly
            290                 295                 300

Tyr Thr Trp Leu Glu Ala Val Ile Phe Leu Ile Gly Ile Ile Val Ala
305                 310                 315                 320

Asn Val Pro Glu Gly Leu Leu Ala Thr Val Thr Val Cys Leu Thr Leu
                325                 330                 335

Thr Ala Lys Arg Met Ala Arg Lys Asn Cys Leu Val Lys Asn Leu Glu
            340                 345                 350

Ala Val Glu Thr Leu Gly Ser Thr Ser Thr Ile Cys Ser Asp Lys Thr
            355                 360                 365

Gly Thr Leu Thr Gln Asn Arg Met Thr Val Ala His Met Trp Phe Asp
            370                 375                 380

Asn Gln Ile His Glu Ala Asp Thr Thr Glu Asp Gln Ser Gly Thr Ser
385                 390                 395                 400

Phe Asp Lys Ser Ser His Thr Trp Val Ala Leu Ser His Ile Ala Gly
            405                 410                 415

Leu Cys Asn Arg Ala Val Phe Lys Gly Gly Gln Asp Asn Ile Pro Val
            420                 425                 430

Leu Lys Arg Asp Val Ala Gly Asp Ala Ser Glu Ser Ala Leu Leu Lys
            435                 440                 445

Cys Ile Glu Leu Ser Ser Gly Ser Val Lys Leu Met Arg Glu Arg Asn
            450                 455                 460

Lys Lys Val Ala Glu Ile Pro Phe Asn Ser Thr Asn Lys Tyr Gln Leu
465                 470                 475                 480

Ser Ile His Glu Thr Glu Asp Pro Asn Asp Asn Arg Tyr Leu Leu Val
                485                 490                 495

Met Lys Gly Ala Pro Glu Arg Ile Leu Asp Arg Cys Ser Thr Ile Leu
            500                 505                 510

Leu Gln Gly Lys Glu Gln Pro Leu Asp Glu Met Lys Glu Ala Phe
            515                 520                 525

Gln Asn Ala Tyr Leu Glu Leu Gly Gly Leu Gly Glu Arg Val Leu Gly
            530                 535                 540

Phe Cys His Tyr Tyr Leu Pro Glu Glu Gln Phe Pro Lys Gly Phe Ala
545                 550                 555                 560

Phe Asp Cys Asp Asp Val Asn Phe Thr Thr Asp Asn Leu Cys Phe Val
                565                 570                 575

Gly Leu Met Ser Met Ile Asp Pro Pro Arg Ala Ala Val Pro Asp Ala
```

```
                580             585             590
    Val Gly Lys Cys Arg Ser Ala Gly Ile Lys Val Ile Met Val Thr Gly
                595             600             605

Asp His Pro Ile Thr Ala Lys Ala Ile Ala Lys Gly Val Gly Ile Ile
    610             615             620

Ser Glu Gly Asn Glu Thr Val Glu Asp Ile Ala Ala Arg Leu Asn Ile
    625             630             635             640

Pro Val Ser Gln Val Asn Pro Arg Asp Ala Lys Ala Cys Val Ile His
                645             650             655

Gly Thr Asp Leu Lys Asp Phe Thr Ser Glu Gln Ile Asp Glu Ile Leu
                660             665             670

Gln Asn His Thr Glu Ile Val Phe Ala Arg Thr Ser Pro Gln Gln Lys
                675             680             685

Leu Ile Ile Val Glu Gly Cys Gln Arg Gln Gly Ala Ile Val Ala Val
                690             695             700

Thr Gly Asp Gly Val Asn Asp Ser Pro Ala Leu Lys Lys Ala Asp Ile
    705             710             715             720

Gly Val Ala Met Gly Ile Ala Gly Ser Asp Val Ser Lys Gln Ala Ala
                        725             730             735

Asp Met Ile Leu Leu Asp Asp Asn Phe Ala Ser Ile Val Thr Gly Val
                    740             745             750

Glu Glu Gly Arg Leu Ile Phe Asp Asn Leu Lys Lys Ser Ile Ala Tyr
                755             760             765

Thr Leu Thr Ser Asn Ile Pro Glu Ile Thr Pro Phe Leu Leu Phe Ile
                770             775             780

Met Ala Asn Ile Pro Leu Pro Leu Gly Thr Ile Thr Ile Leu Cys Ile
    785             790             795             800

Asp Leu Gly Thr Asp Met Val Pro Ala Ile Ser Leu Ala Tyr Glu Ala
                        805             810             815

Ala Glu Ser Asp Ile Met Lys Arg Gln Pro Arg Asn Pro Arg Thr Asp
                820             825             830

Lys Leu Val Asn Glu Arg Leu Ile Ser Met Ala Tyr Gly Gln Ile Gly
                835             840             845

Met Ile Gln Ala Leu Gly Gly Phe Phe Ser Tyr Phe Val Ile Leu Ala
    850             855             860

Glu Asn Gly Phe Leu Pro Gly Asn Leu Val Gly Ile Arg Leu Asn Trp
    865             870             875             880

Asp Asp Arg Thr Val Asn Asp Leu Glu Asp Ser Tyr Gly Gln Gln Trp
                        885             890             895

Thr Tyr Glu Gln Arg Lys Val Val Glu Phe Thr Cys His Thr Ala Phe
                900             905             910

Phe Val Ser Ile Val Val Val Gln Trp Ala Asp Leu Ile Ile Cys Lys
                915             920             925

Thr Arg Arg Asn Ser Val Phe Gln Gln Gly Met Lys Asn Lys Ile Leu
                930             935             940

Ile Phe Gly Leu Phe Glu Glu Thr Ala Leu Ala Ala Phe Leu Ser Tyr
    945             950             955             960

Cys Pro Gly Met Asp Val Ala Leu Arg Met Tyr Pro Leu Lys Pro Ser
                        965             970             975

Trp Trp Phe Cys Ala Phe Pro Tyr Ser Phe Leu Ile Phe Val Tyr Asp
                    980             985             990

Glu Ile Arg Lys Leu Ile Leu Arg  Arg Asn Pro Gly Gly  Trp Val Glu
                995                  1000                 1005
```

Lys Glu Thr Tyr Tyr
        1010

<210> SEQ ID NO 4
<211> LENGTH: 429
<212> TYPE: DNA
<213> ORGANISM: Homo sapiens

<400> SEQUENCE: 4
ctgcagaggg ccctgcgtat gagtgcaagt gggttttagg accaggatga ggggggtgg       60 gggtgcctac ctgacgaccg accccgaccc actggacaag cacccaaccc ccattcccca     120
aattgcgcat ccctatcag agaggggag gggaaacagg atgcggcgag gcgcgtgcgc       180
actgccagct tcagcaccgc ggacagtgcc ttcgccccg cctggcggcg cgcgccaccg      240
ccgcctcagc actgaaggcg cgctgacgtc actcgccggt cccccgcaaa ctcccccttcc    300 cggccacctt ggtcgcgtcc gcgccgccgc cggcccagcc ggaccgcacc acgcgaggcg     360
cgagataggg gggcacgggc gcgaccatct gcgctgcggc ccggcgact cagcgctgcc      420 tcagtctgc                                                             429

<210> SEQ ID NO 5
<211> LENGTH: 402
<212> TYPE: DNA
<213> ORGANISM: Homo sapiens

<400> SEQUENCE: 5
ctgcagaggg ccctgcgtat gagtgcaagt gggttttagg accaggatga ggggggtgg       60 gggtgcctac ctgacgaccg accccgaccc actggacaag cacccaaccc ccattcccca     120
aattgcgcat ccctatcag agaggggag gggaaacagg atgcggcgag gcgcgtgcgc       180
actgccagct tcagcaccgc ggacagtgcc ttcgccccg cctggcggcg cgcgccaccg      240
ccgcctcagc actgaaggcg cgctgacgtc actcgccggt cccccgcaaa ctcccccttcc    300 cggccacctt ggtcgcgtcc gcgccgccgc cggcccagcc ggaccgcacc acgcgaggcg     360
cgagataggg gggcacgggc gcgaccatct gcgctgcggc gc                        402

<210> SEQ ID NO 6
<211> LENGTH: 1010
<212> TYPE: PRT
<213> ORGANISM: Homo sapiens

<400> SEQUENCE: 6

Met Gly Asp Lys Lys Asp Lys Asp Ser Pro Lys Lys Asn Lys Gly
1               5                   10                  15

Lys Glu Arg Arg Asp Leu Asp Asp Leu Lys Lys Glu Val Ala Met Thr
            20                  25                  30

Glu His Lys Met Ser Val Glu Glu Val Cys Arg Lys Tyr Asn Thr Asp
        35                  40                  45

Cys Val Gln Gly Leu Thr His Ser Lys Ala Gln Glu Ile Leu Ala Arg
    50                  55                  60

Asp Gly Pro Asn Ala Leu Thr Pro Pro Thr Thr Pro Glu Trp Val
65                  70                  75                  80

Lys Phe Cys Arg Gln Leu Phe Gly Gly Phe Ser Ile Leu Leu Trp Ile
                85                  90                  95

Gly Ala Ile Leu Cys Phe Leu Ala Tyr Gly Ile Gln Ala Gly Thr Glu
            100                 105                 110

-continued

```
Asp Asp Pro Ser Gly Asp Asn Leu Tyr Leu Gly Ile Val Leu Ala Ala
            115                 120                 125

Val Val Ile Ile Thr Gly Cys Phe Ser Tyr Tyr Gln Glu Ala Lys Ser
130                 135                 140

Ser Lys Ile Met Glu Ser Phe Lys Asn Met Val Pro Gln Gln Ala Leu
145                 150                 155                 160

Val Ile Arg Glu Gly Glu Lys Met Gln Val Asn Ala Glu Glu Val Val
            165                 170                 175

Val Gly Asp Leu Val Glu Ile Lys Gly Gly Asp Arg Val Pro Ala Asp
            180                 185                 190

Leu Arg Ile Ile Ser Ala His Gly Cys Lys Val Asp Asn Ser Ser Leu
            195                 200                 205

Thr Gly Glu Ser Glu Pro Gln Thr Arg Ser Pro Asp Cys Thr His Asp
            210                 215                 220

Asn Pro Leu Glu Thr Arg Asn Ile Thr Phe Phe Ser Thr Asn Cys Val
225                 230                 235                 240

Glu Gly Thr Ala Arg Gly Val Val Ala Thr Gly Asp Arg Thr Val
            245                 250                 255

Met Gly Arg Ile Ala Thr Leu Ala Ser Gly Leu Glu Val Gly Lys Thr
            260                 265                 270

Pro Ile Ala Ile Glu Ile Glu His Phe Ile Gln Leu Ile Thr Gly Val
            275                 280                 285

Ala Val Phe Leu Gly Val Ser Phe Phe Ile Leu Ser Leu Ile Leu Gly
            290                 295                 300

Tyr Thr Trp Leu Glu Ala Val Ile Phe Leu Ile Gly Ile Ile Val Ala
305                 310                 315                 320

Asn Val Pro Glu Gly Leu Leu Ala Thr Val Thr Val Cys Leu Thr Leu
            325                 330                 335

Thr Ala Lys Arg Met Ala Arg Lys Asn Cys Leu Val Lys Asn Leu Glu
            340                 345                 350

Ala Val Glu Thr Leu Gly Ser Thr Ser Thr Ile Cys Ser Asp Lys Thr
            355                 360                 365

Gly Thr Leu Thr Gln Asn Arg Met Thr Val Ala His Met Trp Phe Asp
            370                 375                 380

Asn Gln Ile His Glu Ala Asp Thr Thr Glu Asp Gln Ser Gly Thr Ser
385                 390                 395                 400

Phe Asp Lys Ser Ser His Thr Trp Val Ala Leu Ser His Ile Ala Gly
            405                 410                 415

Leu Cys Asn Arg Ala Val Phe Lys Gly Gly Gln Asp Asn Ile Pro Val
            420                 425                 430

Leu Lys Arg Asp Val Ala Gly Asp Ala Ser Glu Ser Ala Leu Leu Lys
            435                 440                 445

Cys Ile Glu Leu Ser Ser Gly Ser Val Lys Leu Met Arg Glu Arg Asn
            450                 455                 460

Lys Lys Val Ala Glu Ile Pro Phe Asn Ser Thr Asn Lys Tyr Gln Leu
465                 470                 475                 480

Ser Ile His Glu Thr Glu Asp Pro Asn Asp Asn Arg Tyr Leu Leu Val
            485                 490                 495

Met Lys Gly Ala Pro Glu Arg Ile Leu Asp Arg Cys Ser Thr Ile Leu
            500                 505                 510

Leu Gln Gly Lys Glu Gln Pro Leu Asp Glu Glu Met Lys Glu Ala Phe
            515                 520                 525

Gln Asn Ala Tyr Leu Glu Leu Gly Gly Leu Gly Glu Arg Val Leu Gly
```

-continued

```
            530                 535                 540
Phe Cys His Tyr Tyr Leu Pro Glu Glu Gln Phe Pro Lys Gly Phe Ala
545                 550                 555                 560

Phe Asp Cys Asp Asp Val Asn Phe Thr Thr Asp Asn Leu Cys Phe Val
                565                 570                 575

Gly Leu Met Ser Met Ile Asp Pro Pro Arg Ala Ala Val Pro Asp Ala
                580                 585                 590

Val Gly Lys Cys Arg Ser Ala Gly Ile Lys Val Ile Met Val Thr Gly
                595                 600                 605

Asp His Pro Ile Thr Ala Lys Ala Ile Ala Lys Gly Val Gly Ile Ile
                610                 615                 620

Ser Glu Gly Asn Glu Thr Val Glu Asp Ile Ala Ala Arg Leu Asn Ile
625                 630                 635                 640

Pro Val Ser Gln Val Asn Pro Arg Asp Ala Lys Ala Cys Val Ile His
                645                 650                 655

Gly Thr Asp Leu Lys Asp Phe Thr Ser Glu Gln Ile Asp Glu Ile Leu
                660                 665                 670

Gln Asn His Thr Glu Ile Val Phe Ala Arg Thr Ser Pro Gln Gln Lys
                675                 680                 685

Leu Ile Ile Val Glu Gly Cys Gln Arg Gln Gly Ala Ile Val Ala Val
                690                 695                 700

Thr Gly Asp Gly Val Asn Asp Ser Pro Ala Leu Lys Lys Ala Asp Ile
705                 710                 715                 720

Gly Val Ala Met Gly Ile Ala Gly Ser Asp Val Ser Lys Gln Ala Ala
                725                 730                 735

Asp Met Ile Leu Leu Asp Asp Asn Phe Ala Ser Ile Val Thr Gly Val
                740                 745                 750

Glu Glu Gly Arg Leu Ile Phe Asp Asn Leu Lys Lys Ser Ile Ala Tyr
                755                 760                 765

Thr Leu Thr Ser Asn Ile Pro Glu Ile Thr Pro Phe Leu Leu Phe Ile
                770                 775                 780

Met Ala Asn Ile Pro Leu Pro Leu Gly Thr Ile Thr Ile Leu Cys Ile
785                 790                 795                 800

Asp Leu Gly Thr Asp Met Val Pro Ala Ile Ser Leu Ala Tyr Glu Ala
                805                 810                 815

Ala Glu Ser Asp Ile Met Lys Arg Gln Pro Arg Asn Pro Arg Thr Asp
                820                 825                 830

Lys Leu Val Asn Glu Arg Leu Ile Ser Met Ala Tyr Gly Gln Ile Gly
                835                 840                 845

Met Ile Gln Ala Leu Gly Gly Phe Ser Tyr Phe Val Ile Leu Ala
850                 855                 860

Glu Asn Gly Phe Leu Pro Gly Asn Leu Val Gly Ile Arg Leu Asn Trp
865                 870                 875                 880

Asp Asp Arg Thr Val Asn Asp Leu Glu Asp Ser Tyr Gly Gln Gln Trp
                885                 890                 895

Thr Tyr Glu Gln Arg Lys Val Val Glu Phe Thr Cys His Thr Ala Phe
                900                 905                 910

Phe Val Ser Ile Val Val Gln Trp Ala Asp Leu Ile Ile Cys Lys
                915                 920                 925

Thr Arg Arg Asn Ser Val Phe Gln Gln Gly Met Lys Asn Lys Ile Leu
                930                 935                 940

Ile Phe Gly Leu Phe Glu Glu Thr Ala Leu Ala Ala Phe Leu Ser Tyr
945                 950                 955                 960
```

```
           Cys Pro Gly Met Asp Val Ala Leu Arg Met Tyr Pro Leu Lys Pro Ser
                       965                 970                 975

Trp Trp Phe Cys Ala Phe Pro Tyr Ser Phe Leu Ile Phe Val Tyr Asp
                       980                 985                 990

Glu Ile Arg Lys Leu Ile Leu Arg Arg Asn Pro Gly Gly Trp Val Glu
                       995                 1000                1005

Lys Glu
               1010

<210> SEQ ID NO 7
<211> LENGTH: 3031
<212> TYPE: DNA
<213> ORGANISM: Homo sapiens

<400> SEQUENCE: 7
atgggggaca agaaagatga caaggactca cccaagaaga caagggcaa ggagcgccgg      60 gacctggatg acctcaagaa ggaggtggct atgacagagc acaagatgtc agtggaagag    120
gtctgccgga aatacaacac agactgtgtg cagggtttga cccacagcaa agcccaggag    180
atcctggccc gggatgggcc taacgcactc acgccaccgc ctaccacccc agagtgggtc    240
aagttttgcc ggcagctctt cggggcttc tccatcctgc tgtggatcgg gctatcctc    300 tgcttcctgg cctacggtat ccaggcgggc accgaggacg accctctgg tgacaacctg    360 tacctgggca tcgtgctggc ggccgtggtg atcatcactg gctgcttctc ctactaccag    420
gaggccaaga gctccaagat catggagtcc ttcaagaaca tggtgcccca gcaagccctg    480
gtgatccggg aaggtgagaa gatgcaggtg aacgctgagg aggtggtggt cggggacctg    540
gtggagatca aggtggagc ccgagtgcca gctgacctgc ggatcatctc agcccacggc    600
tgcaaggtgg acaactcctc cctgactggc gaatccgagc ccagactcg ctctcccgac    660 tgcacgcacg acaaccccttt ggagactcgg aacatcacct tcttccac caactgtgtg    720 gaaggcacgg ctcggggcgt ggtggtggcc acgggcgacc gcactgtcat gggccgtatc    780
gccaccctgg catcagggct ggaggtgggc aagacgccca tcgccatcga gattgagcac    840
ttcatccagc tcatcaccgg cgtggctgtc ttcctgggtg tctccttctt catcctctcc    900
ctcattctcg gatacacctg gcttgaggct gtcatcttcc tcatcggcat catcgtggcc    960
aatgtcccag agggtctgct ggccactgtc actgtgtgtc tgacgctgac cgccaagcgc   1020
atggcccgga gaactgcctg ggtgaagaac ctggaggctg tagaaaccct gggctccacg   1080
tccaccatct gctcagataa gacagggacc ctcactcaga accgcatgac agtcgcccac   1140
atgtggtttg acaaccagat ccacgaggct gacaccactg aggaccagtc agggacctca   1200
tttgacaaga gttcgcacac ctgggtggcc ctgtctcaca tcgctgggct ctgcaatcgc   1260
gctgtcttca agggtggtca ggacaacatc cctgtgctca gagggatgt ggctggggat   1320 gcgtctgagt ctgccctgct caagtgcatc gagctgtcct ctggctccgt gaagctgatg   1380
cgtgaacgca caagaaagt ggctgagatt cccttcaatt ccaccaacaa ataccagctc   1440
tccatccatg agaccgagga ccccaacgac aaccgatacc tgctggtgat gaagggtgcc   1500
cccgagcgca tcctgaccgc tgctccacc atcctgctac agggcaagga gcagcctctg   1560
gacgaggaaa tgaaggaggc cttccagaat gcctaccttg agctcggtgg cctgggcgag   1620
cgcgtgcttg gttctgcca ttattacctg cccgaggagc agttccccaa gggctttgcc   1680
ttcgactgtg atgacgtgaa cttcaccacg gacaacctct gctttgtggg cctcatgtcc   1740
```

```
atgatcgacc cacccccgggc agccgtccct gacgcggtgg gcaagtgtcg cagcgcaggc    1800
atcaaggtca tcatggtcac cggcgatcac cccatcacgg ccaaggccat tgccaagggt    1860
gtgggcatca tctctgaggg caacgagact gtggaggaca tcgccgcccg gctcaacatt    1920
cccgtcagcc aggttaaccc ccgggatgcc aaggcctgcg tgatccacgg caccgacctc    1980
aaggacttca cctccgagca aatcgacgag atcctgcaga atcacaccga gatcgtcttc    2040
gcccgcacat cccccagca gaagctcatc attgtggagg gctgtcagag acagggtgca    2100
attgtggctg tgaccgggga tggtgtgaac gactcccccg ctctgaagaa ggccgacatt    2160
ggggtggcca tgggcatcgc tggctctgac gtctccaagc aggcagctga catgatcctg    2220
ctggacgaca actttgcctc catcgtcaca ggggtggagg agggccgcct gatcttcgac    2280
aacctaaaga gtccattgc ctacaccctg accagcaata tcccggagat cacgcccttc    2340
ctgctgttca tcatggccaa catcccgctg cccctgggca ccatcaccat cctctgcatc    2400
gatctgggca ctgacatggt ccctgccatc tcactggcgt acgaggctgc cgaaagcgac    2460
atcatgaaga gacagcccag gaacccgcgg acggacaaat tggtcaatga gagactcatc    2520
agcatggcct acgggcagat tggaatgatc caggctctcg gtggcttctt ctcttacttt    2580
gtgatcctgg cagaaaatgg cttcttgccc ggcaacctgg tgggcatccg gctgaactgg    2640
gatgaccgca ccgtcaatga cctggaagac agttacgggc agcagtggac atacgagcag    2700
aggaaggtgg tggagttcac ctgccacacg gccttctttg tgagcatcgt tgtcgtccag    2760
tgggccgatc tgatcatctg caagacccgg aggaactcgg tcttccagca gggcatgaag    2820
aacaagatcc tgatcttcgg gctgtttgag gagacggccc tggctgcctt cctgtcctac    2880
tgccccggca tggacgtggc cctgcgcatg taccctctca gcccagctg gtggttctgt    2940 gccttcccct acagtttcct catcttcgtc tacgacgaaa tccgcaaact catcctgcgc    3000
aggaacccag ggggttgggt ggagaaggaa a                                   3031

<210> SEQ ID NO 8
<211> LENGTH: 428
<212> TYPE: DNA
<213> ORGANISM: Mus musculus

<400> SEQUENCE: 8
aagtgcaatt tagcctaagg aatggaagag gttggtaaac agggtaggat cgtgggaggg     60
agtttcgtta ctacaggtcc ggaccctcag gacaagaacc ccacccccac tccccaaatt    120
gcgcatcccc cgcccccatc agaggggag gggaagaggt tgcggcgcgg cgcatgcgca    180
ctgtcggatt cagcaccgcg gtcagagcct tcgcctccgc tgccggcgcg caccaccacc    240
tccccagcac caaaggctga ctgacgtcac tcactagccc tccccaaact ccccttcctc    300
gccgccttgg tcgcgtccat gctgccgtga gtccagtcgg accgcaccac gagaggtgca    360
agatagggag gtgcgggcgc gaccatacgc tctgccgtgc gcagagcctc cgggctgcct    420
cagtctgc                                                            428

<210> SEQ ID NO 9
<211> LENGTH: 486
<212> TYPE: DNA
<213> ORGANISM: Artificial Sequence
<220> FEATURE:
<223> OTHER INFORMATION: Synthetic oligonucleotide

<400> SEQUENCE: 9
agtgcaagtg ggttttttagg accaggatga ggcggggtgg gggtgcctac ctgacgaccg     60
```

```
accccggacc cactggacaa gcacccaacc cccattcccc aaattgcgca tccctaatc      120 agagagggg  agggaaaca  ggatgcggcg aggcgcgtgc gcactgccaa gcttcagcac     180
cgcggacagt gccttcgccc ccgcctggcg gcgcgcgccc accgccgcct cagcactgaa    240
ggcgcgctga cgtcactcgc cggtcccccg acaaactccc cttcccggcc accttggtcg    300
cgtccgcgcc gccgccggcc ccagccggac cgcaccacgc gaggcgcgag ataggggggc    360
acgggcgcga cccatctgcg ctgcggcgcc ggcgactcag cgctgcctca gtctgcggtg    420
ggcaagcgga ggagtcgtgt cgtgcctgag agcgcagtcg agaaggtacc gaggagatct    480
gccgcc                                                                486

<210> SEQ ID NO 10
<211> LENGTH: 144
<212> TYPE: DNA
<213> ORGANISM: Artificial Sequence
<220> FEATURE:
<223> OTHER INFORMATION: AAV-ITR

<400> SEQUENCE: 10
tcctgcaggc agctgcgcgc tcgctcgctc actgaggccg cccgggcaaa gtcccgggcg    60
tcgggcgacc tttggtcgcc cggcctcagt gagcgagcga gctgcgcaga gagggagtgg    120
ccaactccat cactagggt tcct                                             144

<210> SEQ ID NO 11
<211> LENGTH: 27
<212> TYPE: DNA
<213> ORGANISM: Artificial Sequence
<220> FEATURE:
<223> OTHER INFORMATION: Linker

<400> SEQUENCE: 11
acctactaca cgcgtacgcg gccgctc                                         27

<210> SEQ ID NO 12
<211> LENGTH: 30
<212> TYPE: DNA
<213> ORGANISM: Artificial Sequence
<220> FEATURE:
<223> OTHER INFORMATION: Myc tag

<400> SEQUENCE: 12
gagcagaaac tcatctcaga agaggatctg                                      30

<210> SEQ ID NO 13
<211> LENGTH: 18
<212> TYPE: DNA
<213> ORGANISM: Artificial Sequence
<220> FEATURE:
<223> OTHER INFORMATION: Linker

<400> SEQUENCE: 13
gcagcaaatg atatcctg                                                   18

<210> SEQ ID NO 14
<211> LENGTH: 24
<212> TYPE: DNA
<213> ORGANISM: Artificial Sequence
<220> FEATURE:
<223> OTHER INFORMATION: FLAG tag

<400> SEQUENCE: 14
```
gattacaagg atgacgacga taaa 24

<210> SEQ ID NO 15
<211> LENGTH: 6
<212> TYPE: DNA
<213> ORGANISM: Artificial Sequence
<220> FEATURE:
<223> OTHER INFORMATION: Linker

<400> SEQUENCE: 15 ggattc 6

<210> SEQ ID NO 16
<211> LENGTH: 708
<212> TYPE: DNA
<213> ORGANISM: Artificial Sequence
<220> FEATURE:
<223> OTHER INFORMATION: mCherry ORF

<400> SEQUENCE: 16
gtgagcaagg gcgaggagga taacatggcc atcatcaagg agttcatgcg cttcaaggtg 60
cacatggagg gctccgtgaa cggccacgag ttcgagatcg agggcgaggg cgagggccgc 120
ccctacgagg gcacccagac cgccaagctg aaggtgacca agggtggccc cctgcccttc 180
gcctgggaca tcctgtcccc tcagttcatg tacggctcca aggcctacgt gaagcacccc 240
gccgacatcc ccgactactt gaagctgtcc ttccccgagg gcttcaagtg ggagcgcgtg 300
atgaacttcg aggacggcgg cgtggtgacc gtgacccagg actcctccct gcaggacggc 360
gagttcatct acaaggtgaa gctgcgcggc accaacttcc cctccgacgg ccccgtaatg 420
cagaagaaga ccatgggctg ggaggcctcc tccgagcgga tgtaccccga ggacggcgcc 480
ctgaagggcg agatcaagca gaggctgaag ctgaaggacg gcggccacta cgacgctgag 540
gtcaagacca cctacaaggc caagaagccc gtgcagctgc ccggcgccta caacgtcaac 600
atcaagttgg acatcaccto ccacaacgag gactacacca tcgtggaaca gtacgaacgc 660
gccgagggcc gccactccac cggcggcatg gacgagctgt acaagtaa 708

<210> SEQ ID NO 17
<211> LENGTH: 122
<212> TYPE: DNA
<213> ORGANISM: Artificial Sequence
<220> FEATURE:
<223> OTHER INFORMATION: sv40 polyA

<400> SEQUENCE: 17
taagatacat tgatgagttt ggacaaacca actagaat gcagtgaaaa aaatgcttta 60
tttgtgaaat ttgtgatgct attgctttat ttgtaaccat tataagctgc aataaacaag 120
tt 122

<210> SEQ ID NO 18
<211> LENGTH: 144
<212> TYPE: DNA
<213> ORGANISM: Artificial Sequence
<220> FEATURE:
<223> OTHER INFORMATION: AAV-ITR

<400> SEQUENCE: 18
aggaacccct agtgattgga gttggccact ccctctctgc gcgctcgctc gctcactgag 60
gccgggtcga ccaaaggtcg cccgacgccc gggctttgcc cggcggcct cagtgagtcg 120 agcgagcgcg cagctgcctg cagg 144

<210> SEQ ID NO 19
<211> LENGTH: 4740
<212> TYPE: DNA
<213> ORGANISM: Artificial Sequence
<220> FEATURE:
<223> OTHER INFORMATION: Synthetic vector

<400> SEQUENCE: 19

| | | | | | |
|---|---|---|---|---|---|
| tcctgcaggc | agctgcgcgc | tcgctcgctc | actgaggccg | cccgggcaaa | gtcccgggcg | 60 |
| tcgggcgacc | tttggtcgcc | cggcctcagt | gagcgagcga | gctgcgcaga | gagggagtgg | 120 |
| ccaactccat | cactaggggt | tcctagtgca | agtgggtttt | taggaccagg | atgaggcggg | 180 |
| gtggggtgc | ctacctgacg | accgaccccg | gacccactgg | acaagcaccc | aaccccatt | 240 |
| ccccaaattg | cgcatcccct | aatcagagag | ggggagggga | aacaggatgc | ggcgaggcgc | 300 |
| gtgcgcactg | ccaagcttca | gcaccgcgga | cagtgccttc | gccccgcct | ggcggcgcgc | 360 |
| gcccaccgcc | gcctcagcac | tgaaggcgcg | ctgacgtcac | tcgccggtcc | cccgacaaac | 420 |
| tccccttccc | ggccaccttg | gtcgcgtccg | cgccgccgcc | ggcccagcc | ggaccgcacc | 480 |
| acgcgaggcg | cgagataggg | gggcacgggc | gcgacccatc | tgcgctgcgg | cgccggcgac | 540 |
| tcagcgctgc | ctcagtctgc | ggtgggcaag | cggaggagtc | gtgtcgtgcc | tgagagcgca | 600 |
| gtcgagaagg | taccgaggag | atctgccgcc | atggggaca | agaaagatga | caaggactca | 660 |
| cccaagaaga | caagggcaa | ggagcgccgg | gacctggatg | acctcaagaa | ggaggtggct | 720 |
| atgacagagc | acaagatgtc | agtggaagag | gtctgccgga | atacaacac | agactgtgtg | 780 |
| cagggtttga | cccacagcaa | agcccaggag | atcctggccc | gggatgggcc | taacgcactc | 840 |
| acgccaccgc | ctaccacccc | agagtgggtc | aagttttgcc | ggcagctctt | cgggggcttc | 900 |
| tccatcctgc | tgtggatcgg | ggctatcctc | tgcttcctgg | cctacggtat | ccaggcgggc | 960 |
| accgaggacg | acccctctgg | tgacaacctg | tacctgggca | tcgtgctggc | ggccgtggtg | 1020 |
| atcatcactg | gctgcttctc | ctactaccag | gaggccaaga | gctccaagat | catggagtcc | 1080 |
| ttcaagaaca | tggtgcccca | gcaagccctg | gtgatccggg | aaggtgagaa | gatgcaggtg | 1140 |
| aacgctgagg | aggtggtggt | cggggacctg | gtggagatca | agggtggaga | ccgagtgcca | 1200 |
| gctgacctgc | ggatcatctc | agcccacggc | tgcaaggtgg | acaactcctc | cctgactggc | 1260 |
| gaatccgagc | cccagactcg | ctctcccgac | tgcacgcacg | acaaccctt | ggagactcgg | 1320 |
| aacatcacct | tcttttccac | caactgtgtg | gaaggcacgg | ctcggggcgt | ggtggtggcc | 1380 |
| acgggcgacc | gcactgtcat | gggccgtatc | gccaccctgg | catcaggct | ggaggtgggc | 1440 |
| aagacgccca | tcgccatcga | gattgagcac | ttcatccagc | tcatcaccgg | cgtggctgtc | 1500 |
| ttcctgggtg | tctccttctt | catcctctcc | ctcattctcg | gatacacctg | gcttgaggct | 1560 |
| gtcatcttcc | tcatcggcat | catcgtggcc | aatgtcccag | agggtctgct | ggccactgtc | 1620 |
| actgtgtgtc | tgacgctgac | cgccaagcgc | atggcccgga | agaactgcct | ggtgaagaac | 1680 |
| ctggaggctg | tagaaaccct | gggctccacg | tccaccatct | gctcagataa | gacagggacc | 1740 |
| ctcactcaga | accgcatgac | agtcgcccac | atgtggtttg | acaaccagat | ccacgaggct | 1800 |
| gacaccactg | aggaccagtc | agggacctca | tttgacaaga | gttcgcacac | ctgggtggcc | 1860 |
| ctgtctcaca | tcgctgggct | ctgcaatcgc | gctgtcttca | agggtggtca | ggacaacatc | 1920 |
| cctgtgctca | gagggatgt | ggctggggat | gcgtctgagt | ctgccctgct | caagtgcatc | 1980 |
| gagctgtcct | ctggctccgt | gaagctgatg | cgtgaacgca | acaagaaagt | ggctgagatt | 2040 |

```
cccttcaatt ccaccaacaa ataccagctc tccatccatg agaccgagga ccccaacgac    2100
aaccgatacc tgctggtgat gaagggtgcc cccgagcgca tcctggaccg ctgctccacc    2160
atcctgctac agggcaagga gcagcctctg gacgaggaaa tgaaggaggc cttccagaat    2220
gcctaccttg agctcggtgg cctgggcgag cgcgtgcttg gtttctgcca ttattacctg    2280
cccgaggagc agttccccaa gggctttgcc ttcgactgtg atgacgtgaa cttcaccacg    2340
gacaacctct gctttgtggg cctcatgtcc atgatcgacc caccccgggc agccgtccct    2400
gacgcggtgg gcaagtgtcg cagcgcaggc atcaaggtca tcatggtcac cggcgatcac    2460
cccatcacgg ccaaggccat tgccaagggt gtgggcatca tctctgaggg caacgagact    2520
gtggaggaca tcgccgcccg gctcaacatt cccgtcagcc aggttaaccc ccgggatgcc    2580
aaggcctgcg tgatccacgg caccgacctc aaggacttca cctccgagca aatcgacgag    2640
atcctgcaga atcacaccga gatcgtcttc gcccgcacat ccccccagca gaagctcatc    2700
attgtggagg gctgtcagag acagggtgca attgtggctg tgaccgggga tggtgtgaac    2760
gactcccccg ctctgaagaa ggccgacatt ggggtggcca tgggcatcgc tggctctgac    2820
gtctccaagc aggcagctga catgatcctg ctggacgaca actttgcctc catcgtcaca    2880
ggggtggagg agggccgcct gatcttcgac aacctaaaga agtccattgc ctacaccctg    2940
accagcaata tcccggagat cacgcccttc ctgctgttca tcatggccaa catcccgctg    3000
cccctgggca ccatcaccat cctctgcatc gatctgggca ctgacatggt ccctgccatc    3060
tcactggcgt acgaggctgc cgaaagcgac atcatgaaga cagcccag gaacccgcgg    3120 acggacaaat tggtcaatga gagactcatc agcatggcct acgggcagat tggaatgatc    3180
caggctctcg gtggcttctt ctcttacttt gtgatcctgg cagaaaatgg cttcttgccc    3240
ggcaacctgg tgggcatccg gctgaactgg gatgaccgca ccgtcaatga cctggaagac    3300
agttacgggc agcagtggac atacgagcag aggaaggtgg tggagttcac ctgccacacg    3360
gccttctttg tgagcatcgt tgtcgtccag tgggccgatc tgatcatctg caagacccgg    3420
aggaactcgg tcttccagca gggcatgaag aacaagatcc tgatcttcgg gctgtttgag    3480
gagacggccc tggctgcctt cctgtcctac tgccccggca tggacgtggc cctgcgcatg    3540
taccctctca gcccagctg tggttctgt gccttcccct acagtttcct catcttcgtc    3600
tacgacgaaa tccgcaaact catcctgcgc aggaacccag gggttgggt ggagaaggaa    3660 aacctactac acgcgtacgc ggccgctcga gcagaaactc atctcagaag aggatctggc    3720
agcaaatgat atcctggatt acaaggatga cgacgataaa ggattcgtga gcaagggcga    3780
ggaggataac atggccatca tcaaggagtt catgcgcttc aaggtgcaca tggagggctc    3840
cgtgaacggc cacagttcg agatcgaggg cgagggcgag ggccgcccct acgagggcac    3900
ccagaccgcc aagctgaagg tgaccaaggg tggcccctg cccttcgcct gggacatcct    3960
gtcccctcag ttcatgtacg gctccaaggc ctacgtgaag caccccgccg acatccccga    4020
ctacttgaag ctgtccttcc ccgagggctt caagtgggag cgcgtgatga cttcgagga    4080 cggcggcgtg gtgaccgtga cccaggactc ctccctgcag gacggcgagt tcatctacaa    4140
ggtgaagctg cgcggcacca acttcccctc cgacggcccc gtaatgcaga gaagaccat    4200 gggctgggag gcctcctccg agcggatgta ccccgaggac ggcgccctga agggcgagat    4260
caagcagagg ctgaagctga aggacggcgg ccactacgac gctgaggtca agaccaccta    4320
caaggccaag aagcccgtgc agctgccccg cgcctacaac gtcaacatca agttggacat    4380
cacctcccac aacgaggact acaccatcgt ggaacagtac gaacgcgccg agggccgcca    4440
```

```
ctccaccggc ggcatggacg agctgtacaa gtaataagat acattgatga gtttggacaa     4500
accacaacta gaatgcagtg aaaaaaatgc tttatttgtg aaatttgtga tgctattgct     4560
ttatttgtaa ccattataag ctgcaataaa caagttagga accctagtg attggagttg      4620 gccactccct ctctgcgcgc tcgctcgctc actgaggccg gtcgaccaa aggtcgcccg      4680 acgcccggc tttgcccggg cggcctcagt gagtcgagcg agcgcgcagc tgcctgcagg      4740
```

<210> SEQ ID NO 20
<211> LENGTH: 4803
<212> TYPE: DNA
<213> ORGANISM: Artificial Sequence
<220> FEATURE:
<223> OTHER INFORMATION: Synthetic vector

<400> SEQUENCE: 20

```
tcctgcaggc agctgcgcgc tcgctcgctc actgaggccg cccgggcaaa gtcccgggcg      60
tcgggcgacc tttggtcgcc cggcctcagt gagcgagcga gctgcgcaga gagggagtgg     120
ccaactccat cactagggt tcctagtgca agtgggtttt taggaccagg atgaggcggg      180 gtggggtgc ctacctgacg accgaccccg gacccactgg acaagcaccc aaccccatt       240 ccccaaattg cgcatcccct aatcagagag ggggagggga acaggatgc ggcgaggcgc       300 gtgcgcactg ccaagcttca gcaccgcgga cagtgccttc gccccgcct ggcggcgcgc       360 gcccaccgcc gcctcagcac tgaaggcgcg ctgacgtcac tcgccggtcc cccgacaaac     420
tccccttccc ggccaccttg gtcgcgtccg cgccgcgcc ggcccagcc ggaccgcacc      480 acgcgaggcg cgagatagg gggcacgggc gcgacccatc tgcgctgcgg cgccggcgac     540
tcagcgctgc ctcagtctgc ggtgggcaag cggaggagtc gtgtcgtgcc tgagagcgca     600
gtcgagaagg taccgaggag atctgccgcc atggggaca agaaagatga caaggactca       660
cccaagaaga acaagggcaa ggagcgccgg gacctggatg acctcaagaa ggaggtggct     720
atgacagagc acaagatgtc agtggaagag gtctgccgga atacaacac agactgtgtg      780 cagggtttga cccacagcaa agcccaggag atcctggccc gggatgggcc taacgcactc      840
acgccaccgc ctaccacccc agagtgggtc aagttttgcc ggcagctctt cggggggcttc     900 tccatcctgc tgtggatcgg gctatcctc tgcttcctgg cctacggtat ccaggcgggc       960
accgaggacg acccctctgg tgacaacctg tacctgggca tcgtgctggc ggccgtggtg     1020
atcatcactg gctgcttctc ctactaccag gaggccaaga gctccaagat catggagtcc     1080
ttcaagaaca tggtgcccca gcaagccctg gtgatccggg aaggtgagaa gatgcaggtg     1140
aacgctgagg aggtggtggt cggggacctg gtggagatca agggtggaga ccgagtgcca     1200
gctgacctgc ggatcatctc agcccacggc tgcaaggtgg acaactcctc cctgactggc     1260
gaatccgagc ccagactcg ctctcccgac tgcacgcacg acaacccctt ggagactcgg      1320
aacatcacct tcttttccac caactgtgtg gaaggcacgg ctcggggcgt ggtggtggcc     1380
acgggcgacc gcactgtcat gggccgtatc gccaccctgg catcagggct ggaggtgggc     1440
aagacgccca tcgccatcga gattgagcac ttcatccagc tcatcaccgg cgtggctgtc     1500
ttcctgggtg tctccttctt catcctctcc ctcattctcg gatacacctg gcttgaggct     1560
gtcatcttcc tcatcggcat catcgtggcc aatgtcccag agggtctgct ggccactgtc     1620
actgtgtgtc tgacgctgac cgccaagcgc atggcccgga agaactgcct ggtgaagaac     1680
ctggaggctg tagaaacct gggctccacg tccaccatct gctcagataa gacagggacc     1740
```

```
ctcactcaga accgcatgac agtcgcccac atgtggtttg acaaccagat ccacgaggct      1800
gacaccactg aggaccagtc agggacctca tttgacaaga gttcgcacac ctgggtggcc      1860
ctgtctcaca tcgctgggct ctgcaatcgc gctgtcttca agggtggtca ggacaacatc      1920
cctgtgctca gagggatgt ggctggggat cgtctgagt ctgccctgct caagtgcatc        1980
gagctgtcct ctggctccgt gaagctgatg cgtgaacgca acaagaaagt ggctgagatt      2040
cccttcaatt ccaccaacaa ataccagctc tccatccatg agaccgagga ccccaacgac     2100
aaccgatacc tgctggtgat gaagggtgcc cccgagcgca tcctggaccg ctgctccacc      2160
atcctgctac agggcaagga gcagcctctg gacgaggaaa tgaaggaggc cttccagaat      2220
gcctaccttg agctcggtgg cctgggcgag cgcgtgcttg gtttctgcca ttattacctg      2280
cccgaggagc agttcccaa gggctttgcc ttcgactgtg atgacgtgaa cttccaccacg      2340
gacaacctct gctttgtggg cctcatgtcc atgatcgacc caccccgggc agccgtccct      2400
gacgcggtgg gcaagtgtcg cagcgcaggc atcaaggtca tcatggtcac cggcgatcac      2460
cccatcacgg ccaaggccat tgccaagggt gtgggcatca tctctgaggg caacgagact      2520
gtggaggaca tcgccgcccg gctcaacatt cccgtcagcc aggttaaccc ccgggatgcc      2580
aaggcctgcg tgatccacgg caccgacctc aaggacttca cctccgagca aatcgacgag      2640
atcctgcaga atcacaccga gatcgtcttc gcccgcacat cccccagca gaagctcatc       2700
attgtgagg gctgtcagag acagggtgca attgtggctg tgaccgggga tggtgtgaac       2760
gactcccccg ctctgaagaa ggccgacatt ggggtggcca tgggcatcgc tggctctgac      2820
gtctccaagc aggcagctga catgatcctg ctggacgaca actttgcctc catcgtcaca      2880
ggggtggagg agggccgcct gatcttcgac aacctaaaga agtccattgc ctacaccctg      2940
accagcaata tcccggagat cacgcccttc ctgctgttca tcatggccaa catcccgctg      3000
cccctgggca ccatcaccat cctctgcatc gatctgggca ctgacatggt ccctgccatc      3060
tcactggcgt acgaggctgc cgaaagcgac atcatgaaga cagcccag gaacccgcgg         3120
acggacaaat tggtcaatga gagactcatc agcatggcct acgggcagat tggaatgatc      3180
caggctctcg gtggcttctt ctcttacttt gtgatcctgg cagaaaatgg cttcttgccc      3240
ggcaacctgg tgggcatccg gctgaactgg gatgaccgca ccgtcaatga cctggaagac      3300
agttacgggc agcagtggac atacgagcag aggaaggtgg tggagttcac ctgccacacg      3360
gccttctttg tgagcatcgt tgtcgtccag tgggccgatc tgatcatctg caagacccgg      3420
aggaactcgg tcttccagca gggcatgaag aacaagatcc tgatcttcgg gctgtttgag      3480
gagacggccc tggctgcctt cctgtcctac tgccccggca tggacgtggc cctgcgcatg      3540
taccctctca gcccagctg gtggttctgt gccttcccct acagtttcct catcttcgtc       3600
tacgacgaaa tccgcaaact catcctgcgc aggaacccag ggggttgggt ggagaaggaa      3660
aacctactac acgcgtacgc ggccgctcga gcagaaactc atctcagaag aggatctggc      3720
agcaaatgat atcctggatt acaaggatga cgacgataaa ggattcgcca cgaacttctc      3780
tctgttaaag caagcaggag acgtggaaga aaaccccggt cccggattcg tgagcaaggg      3840
cgaggaggat aacatggcca tcatcaagga gttcatgcgc ttcaaggtgc acatggaggg      3900
ctccgtgaac ggccacgagt tcgagatcga gggcgagggc gagggccgcc cctacgaggg      3960
cacccagacc gccaagctga aggtgaccaa gggtggcccc ctgcccttcg cctgggacat      4020
cctgtccct cagttcatgt acggctccaa ggcctacgtg aagcaccccg ccgacatccc       4080
cgactacttg aagctgtcct tccccgaggg cttcaagtgg gagcgcgtga tgaacttcga      4140
```

```
ggacggcggc gtggtgaccg tgacccagga ctcctccctg caggacgcg agttcatcta    4200 caaggtgaag ctgcgcggca ccaacttccc ctccgacggc cccgtaatgc agaagaagac    4260
catgggctgg gaggcctcct ccgagcggat gtaccccgag acggcgccc tgaagggcga    4320 gatcaagcag aggctgaagc tgaaggacg cggccactac gacgctgagg tcaagaccac    4380
ctacaaggcc aagaagcccg tgcagctgcc cggcgcctac aacgtcaaca tcaagttgga    4440
catcacctcc cacaacgagg actacaccat cgtggaacag tacgaacgcg ccgagggccg    4500
ccactccacc ggcggcatgg acgagctgta caagtaataa gatacattga tgagtttgga    4560
caaaccacaa ctagaatgca gtgaaaaaaa tgctttattt gtgaaatttg tgatgctatt    4620
gctttatttg taaccattat aagctgcaat aaacaagtta gaaccccta gtgattggag    4680 ttggccactc cctctctgcg cgctcgctcg ctcactgagg ccgggtcgac caaaggtcgc    4740
ccgacgcccg ggctttgccc gggcggcctc agtgagtcga gcgagcgcgc agctgcctgc    4800
agg                                                                  4803
```

<210> SEQ ID NO 21
<211> LENGTH: 3517
<212> TYPE: DNA
<213> ORGANISM: Artificial Sequence
<220> FEATURE:
<223> OTHER INFORMATION: Synthetic vector

<400> SEQUENCE: 21

```
agtgcaagtg ggttttagg accaggatga ggcggggtgg gggtgcctac ctgacgaccg      60
accccggacc cactggacaa gcacccaacc cccattcccc aaattgcgca tcccctaatc     120
agagaggggg aggggaaaca ggatgcggcg aggcgcgtgc gcactgccaa gcttcagcac     180
cgcggacagt gccttcgccc ccgcctggcg gcgcgcgccc accgccgcct cagcactgaa     240
ggcgcgctga cgtcactcgc cggtccccg acaaactccc cttccggcc accttggtcg      300 cgtccgcgcc gccgccggcc ccagccggac cgcaccacgc gaggcgcgag ataggggggc     360
acgggcgcga cccatctgcg ctgcggcgcc ggcgactcag cgctgcctca gtctgcggtg     420
ggcaagcgga ggagtcgtgt cgtgcctgag agcgcagtcg agaaggtacc gaggagatct     480
gccgccatgg gggacaagaa agatgacaag gactcaccca agaagaacaa gggcaaggag     540
cgccgggacc tggatgacct caagaaggag gtggctatga cagagcacaa gatgtcagtg     600
gaagaggtct gccggaaata caacacagac tgtgtgcagg gtttgaccca gcaaaagcc     660 caggagatcc tggcccggga tgggcctaac gcactcacgc caccgcctac caccccagag     720
tgggtcaagt tttgccggca gctcttcggg ggcttctcca tcctgctgtg gatcggggct     780
atcctctgct tcctgccta cggtatccag gcgggcaccg aggacgaccc ctctggtgac     840
aacctgtacc tgggcatcgt gctggcggcc gtggtgatca tcactggctg cttctcctac     900
taccaggagg ccaagagctc caagatcatg gagtccttca gaacatggt gccccagcaa     960 gccctggtga tccgggaagg tgagaagatg caggtgaacg ctgaggaggt ggtggtcggg    1020
gacctggtgg agatcaaggg tggagaccga gtgccagctg acctgcggat catctcagcc    1080
cacggctgca aggtggacaa ctcctccctg actggcgaat ccgagcccca gactcgctct    1140
cccgactgca cgcacgacaa ccccttggag actcggaaca tcaccttctt ttccaccaac    1200
tgtgtggaag gcacggctcg gggcgtggtg tgtggccacgg gcgaccgcac tgtcatgggc    1260
cgtatcgcca ccctggcatc agggctggag gtgggcaaga cgcccatcgc catcgagatt    1320
```

```
gagcacttca tccagctcat caccggcgtg gctgtcttcc tgggtgtctc cttcttcatc    1380
ctctccctca ttctcggata cacctggctt gaggctgtca tcttcctcat cggcatcatc    1440
gtggccaatg tcccagaggg tctgctggcc actgtcactg tgtgtctgac gctgaccgcc    1500
aagcgcatgg cccggaagaa ctgcctggtg aagaacctgg aggctgtaga acccctgggc    1560
tccacgtcca ccatctgctc agataagaca gggaccctca ctcagaaccg catgacagtc    1620
gcccacatgt ggtttgacaa ccagatccac gaggctgaca ccactgagga ccagtcaggg    1680
acctcatttg acaagagttc gcacacctgg gtggccctgt ctcacatcgc tgggctctgc    1740
aatcgcgctg tcttcaaggg tggtcaggac aacatccctg tgctcaagag ggatgtggct    1800
ggggatgcgt ctgagtctgc cctgctcaag tgcatcgagc tgtcctctgg ctccgtgaag    1860
ctgatgcgtg aacgcaacaa gaaagtggct gagattccct tcaattccac caacaaatac    1920
cagctctcca tccatgagac cgaggacccc aacgacaacc gatacctgct ggtgatgaag    1980
ggtgcccccg agcgcatcct ggaccgctgc tccaccatcc tgctacaggg caaggagcag    2040
cctctggacg aggaaatgaa ggaggccttc agaatgcct accttgagct cggtggcctg    2100
ggcgagcgcg tgcttggttt ctgccattat tacctgcccg aggagcagtt ccccaagggc    2160
tttgccttcg actgtgatga cgtgaacttc accacgaca acctctgctt tgtgggcctc    2220
atgtccatga tcgacccacc ccgggcagcc gtccctgacg cggtgggcaa gtgtcgcagc    2280
gcaggcatca aggtcatcat ggtcaccggc gatcacccca tcacggccaa ggccattgcc    2340
aagggtgtgg gcatcatctc tgagggcaac gagactgtgg aggacatcgc cgcccggctc    2400
aacattcccg tcagccaggt taaccccggg gatgccaagg cctgcgtgat ccacggcacc    2460
gacctcaagg acttcaccct cgagcaaatc gacgagatcc tgcagaatca caccgagatc    2520
gtcttcgccc gcacatcccc ccagcagaag ctcatcattg tggagggctg tcagagacag    2580
ggtgcaattg tggctgtgac cggggatggt gtgaacgact ccccgctct gaagaaggcc    2640 gacattgggg tggccatggg catcgctggc tctgacgtct ccaagcaggc agctgacatg    2700
atcctgctgg acgacaactt tgcctccatc gtcacagggg tggaggaggg ccgcctgatc    2760
ttcgacaacc taaagaagtc cattgcctac accctgacca gcaatatccc ggagatcacg    2820
cccttcctgc tgttcatcat ggccaacatc ccgctgcccc tgggcaccat caccatcctc    2880
tgcatcgatc tgggcactga catggtccct gccatctcac tggcgtacga ggctgccgaa    2940
agcgacatca tgaagagaca gcccaggaac ccgcggacgg acaaattggt caatgagaga    3000
ctcatcagca tggcctacgg gcagattgga atgatccagg ctctcggtgg cttcttctct    3060
tactttgtga tcctggcaga aaatggcttc ttgcccggca acctggtggg catccggctg    3120
aactgggatg accgcaccgt caatgacctg gaagacagtt acgggcagca gtggacatac    3180
gagcagagga aggtggtgga gttcacctgc cacacggcct tctttgtgag catcgttgtc    3240
gtccagtggg ccgatctgat catctgcaag acccggagga actcggtctt ccagcagggc    3300
atgaagaaca agatcctgat cttcgggctg tttgaggaga cggccctggc tgccttcctg    3360
tcctactgcc ccggcatgga cgtggccctg cgcatgtacc ctctcaagcc cagctggtgg    3420
ttctgtgcct tcccctacag tttcctcatc ttcgtctacg acgaaatccg caaactcatc    3480
ctgcgcagga acccagggg ttgggtggag aaggaaa                              3517

<210> SEQ ID NO 22
<211> LENGTH: 57
<212> TYPE: DNA
<213> ORGANISM: Artificial Sequence
```

```
<220> FEATURE:
<223> OTHER INFORMATION: p2A

<400> SEQUENCE: 22
gccacgaact tctctctgtt aaagcaagca ggagacgtgg aagaaaaccc cggtccc         57
```

COMPOSITIONS COMPRISING NUCLEIC ACID MOLECULES AND METHODS OF TREATING ATPASE-MEDIATED DISEASES

CROSS REFERENCE TO RELATED APPLICATIONS

This application is a bypass continuation of PCT/US2020/032978, filed May 14, 2020, which claims priority to U.S. Provisional Patent Application Ser. No. 62/847,416, filed May 14, 2019, the contents of each of which are incorporated herein by reference in its entirety.

FEDERAL FUNDING LEGEND

This invention was made with government support under Grant No. UL1TR002553 awarded by the National Center for Advancing Translational Sciences. The Federal Government has certain rights to this invention

INCORPORATION BY REFERENCE OF SEQUENCE LISTING PROVIDED ELECTRONICALLY

This application contains a substitute Sequence Listing submitted as an electronic text file named "20-489-US-CON_SequenceListing.txt", having a size in bytes of 88 kb, and created on Nov. 10, 2021. The information contained in this electronic file is incorporated herein by reference in its entirety.

BACKGROUND

Field

The present disclosure provides nucleic acid expression cassettes, vectors comprising a nucleic acid encoding ATPases, such as ATP1A3, and compositions thereof, and gene therapy methods for the treatment of ATPase-mediated diseases in a subject.

Description of the Related Art

Alternating Hemiplegia of Childhood (AHC) is a devastating neurological disorder that manifests with severe developmental impairments, episodes of hemiplegias, dystonias, epilepsy, behavioral problems, and often also regression. AHC causes severe morbidity and increased mortality estimated at 3.2/1000 patients/year and at least 4.5% by the age of 29 years. (Panagiotakaki et. al. (2015) *Orphanet J Rare Dis.* 10: 123). It affects approximately 1 in 1,000,000 children. About 80% of the cases are caused by ATP1A3 mutations with the D801N mutation being the most common of those (~40% of patients). AHC is an example of an ATPase-related disease caused by ATPase mutations and the most common of the disorders caused by ATP1A3 mutations. ATPase-related diseases also encompass disorders with secondary ATPase deficiency resulting from other causes such as neurodegenerative disease like Alzheimer's and Parkinson's diseases.

ATP1A3 is the principal subunit of the Na/K-ATPase protein that is expressed in neurons, while ATP1A2 is expressed in glia. ATP1A3 is an enzyme, a signal transduction factor and, most importantly, a pump that consumes 50% of the energy of the brain. (Holm et al. (2016) *Biochem Biophys Acta.* 1857(11): 1807-1828). Primary Na/K-ATPase dysfunction due to ATP1A3 mutations results in AHC and in other neurogenetic disorders. In addition, secondary dysfunction of this pump, resulting from other common neurological disorders, contributes to the pathophysiology of these disorders that include epilepsy, stroke, hypoglycemia, acute ataxia, dystonia and to neuronal death in neurodegenerative diseases including Alzheimer's and Parkinson's diseases. ATP1A3 disease causing mutations, including D801N and I810N, result in profound abnormalities in neuronal excitability. (Hunanyan et al. (2015) *Epilepsia* 56(1): 82-93; Hunanyan et al. (2018) *Epilepsia* 59(7): 1455-1468; Helseth et al. (2018) *Neurobiol Dis.* 119: 100-112). Despite normal levels of ATP1A3 protein expression, these mutations result in reduced ATPase enzyme activity in HeLa cells and COS cells (down to about 54% of normal) as well as in mouse brain (down to about 58% of normal). (Heinzen et al. (2012) *Nat Genet.* 44(9): 1030-1034; Clapcote et al. (2009) *Proc Natl Acad Sci USA.* 106(33): 14085-14090; Kirshenbaum et al. (2013) *PLoS One.* 8(3): e60141).

Currently, the only available therapy for AHC is the calcium channel blocker flunarizine, which causes partial reduction in the hemiplegia spells but has no effect on the other usually very severe manifestations of the disease. Accordingly, there is a need for novel and effective therapies for the treatment of ATP1A3-mediated diseases, including AHC. There is also an acute need for effective therapies to treat other disorders resulting from either secondary deficiencies of other ATPase activities or from mutations of other ATPases, such as mutations of ATP1A2 resulting in severe epileptic encephalopathy.

BRIEF SUMMARY OF THE DISCLOSURE

The present disclosure provides, in part, nucleic acid expression cassettes, vectors, pharmaceutical compositions, kits, and methods for the treatment of ATPase-mediated diseases (e.g., AHC) in a subject.

One aspect of the disclosure provides a nucleic acid expression cassette comprising a nucleic acid sequence encoding an ATPase. In some embodiments, the ATPase is ATP1A1, ATP1A2, ATP1A3, ATP2C1, ATP6A1, ATP6V1B1, ATP6V0A4, ATP7A, ATP7B, or ATP11C. In some embodiments, the ATPase is ATP1A3.

In some embodiments of the disclosure, the nucleic acid sequence encoding an ATPase comprises the sequence set forth in any of SEQ ID NO:01, SEQ ID NO:02, or SEQ ID NO:07, or a fragment, isoform, or homologue thereof, or a sequence having at least 50%-90% identity to the sequence set forth in SEQ ID NO:01, SEQ ID NO:02, or SEQ ID NO:07.

In some embodiments of the disclosure, the nucleic acid expression cassette further comprises a nucleotide sequence encoding ATP1A3 that is codon-optimized to reduce CpG methylation sites and for mammalian expression.

In some embodiments of the disclosure, the nucleic acid expression cassette comprises a nucleic acid sequence encoding ATP1A3 that is operably linked to a promoter and a polyadenylation sequence. In some embodiments of the disclosure, the promoter is a tissue-specific promoter (e.g., a neuron-specific promoter or a heart-specific promoter). In some embodiments of the disclosure, the neuron-specific promoter is selected from the group consisting of synapsin 1, calcium/calmodulin-dependent protein kinase II, tubulin alpha 1, neuron-specific enolase, and platelet-derived growth factor beta chain promoters.

In some embodiments of the disclosure, the promoter is a human synapsin promoter, which can comprise the proximal region of the synapsin 1 promoter (-422 to -22). In some embodiments of the disclosure, the human synapsin promoter comprises the nucleic acid sequence set forth in any of SEQ ID NO:04, SEQ ID NO:05, or SEQ ID NO:09.

In some embodiments of the disclosure, the promoter is a constitutively active promoter, such as the human β-actin, human elongation factor-1α, chicken β-actin combined with cytomegalovirus early enhancer, cytomegalovirus (CMV), simian virus 40, or herpes simplex virus thymidine kinase.

In some embodiments of the disclosure, the nucleic acid expression cassette comprises a transcriptional termination signal, such as the bovine growth hormone polyadenylation signal (BGHpA), Simian virus 40 polyadenylation signal (SV40pA), or a synthetic polyadenylation signal.

Another aspect of the present disclosure provides a vector comprising a nucleic acid sequence encoding an ATPase. In some embodiments, the ATPase is ATP1A1, ATP1A2, ATP1A3, ATP2C1, ATP6A1, ATP6V1B1, ATP6V0A4, ATP7A, ATP7B, or ATP11C. In other embodiments, the ATPase is ATP1A3.

In some embodiments, the vector is a viral vector or non-viral vector. In some embodiments, the vector is a recombinant viral vector.

In some embodiments, the viral vector is selected from the group consisting of an adenovirus vector, an adeno-associated virus vector, a herpes simplex virus vector, a retrovirus vector, a lentivirus vector, and alphavirus vector, a flavivirus vector, a rhabdovirus vector, a measles virus vector, a Newcastle disease viral vector, a poxvirus vector, or a picornavirus vector.

In some embodiments of the disclosure, the adenovirus vector is an AAV serotype selected from the group consisting of AAV1, AAV2, AAV3, AAV4, AAV5, AAV6, AAV7, AAVrh74, AAV8, AAV9, AAV10, AAV11, AAV12 and AAV13. In other embodiments of the disclosure, the adenovirus vector is an AAV serotype selected from the group consisting of AAV1, AAV8, or AAV9. In yet other embodiments of the disclosure, the adenovirus vector is AAV9.

In some embodiments of the disclosure, the vector comprises the AAV9-hSyn-ATP1A3-p2A-mCherry (pBK828) vector.

In some embodiments of the disclosure, the nucleic acid sequence encoding an ATPase is contained in a nucleic acid expression cassette within the vector.

In some embodiments of the disclosure, the vector further comprises one or more of the following elements: (a) an inverted terminal repeat sequence (ITR); (b) a promoter; (c) a transcription terminator; and (d) a flanking inverted terminal repeat sequence (ITR).

In some embodiments of the disclosure, the vector comprises a tissue specific promoter, such as a neuron-specific promoter, muscle-specific promoter, liver-specific promoter, or cardiac-specific promoter. In some embodiments of the disclosure, the vector comprises a promoter that is derived from the human synapsin promoter, which can have a nucleotide sequence set forth in any of SEQ ID NO:04, SEQ ID NO:05, or SEQ ID NO:09.

In some embodiments of the disclosure, the vector comprises a constitutively active promoter, such as a human β-actin, human elongation factor-1α, chicken β-actin combined with cytomegalovirus early enhancer, cytomegalovirus (CMV), simian virus 40, and herpes simplex virus thymidine kinase.

In some embodiments of the disclosure, the vector comprises a transcription terminator, such as the bovine growth hormone polyadenylation signal (BGHpA), Simian virus 40 polyadenylation signal (SV40pA), or a synthetic polyadenylation signal.

Yet another aspect of the disclosure provides a composition comprising a vector comprising a nucleic acid sequence encoding an ATPase.

Yet another aspect of the disclosure provides a pharmaceutical composition comprising a vector comprising a nucleic acid sequence encoding an ATPase and a pharmaceutically acceptable carrier and/or excipient.

Yet another aspect of the disclosure provides a method of treating or preventing an ATPase-mediated disease in a subject, the method comprising administering to the subject a therapeutically effective amount of the nucleic acid expression cassettes, vectors, or compositions thereof described herein, such that the ATPase-mediated disease in the subject is treated or prevented.

In some embodiments of the disclosure, the nucleic acid expression cassettes, vectors, or compositions thereof is administered by a route selected from the group consisting of intramuscular injection, systemically, parenterally by injection, infusion or implantation, intracerebroventricular, intra-cisterna magna, intrahippocampal, and intrathecal.

In some embodiments of the disclosure, the subject is a human.

In some embodiments of the disclosure, the subject has an ATP1A3 protein mutation selected from the group consisting of an E815K mutation, a D801N mutation, an I180N mutation, a R756C mutation, or a V589F mutation.

In some embodiments of the disclosure, the ATPase-mediated disease is selected from the group consisting of rapid-onset dystonia-parkinsonism (RDP), alternating hemiplegia of childhood (AHC), epileptic encephalopathy (EE), cerebellar ataxia, areflexia, pes cavus, optic atrophy and sensorineural hearing loss (CAPOS) syndrome, fever induced paroxysmal weakness and encephalopathy (FIPWE), recurrent episodes of cerebellar ataxia (RECA), early-onset schizophrenia Dystonia Dysmorphism of the face Encephalopathy MRI abnormalities without hemiplegia (D-DEMO) syndrome and Childhood Rapid Onset ataxia (CROA). In other embodiments, the ATPase-mediated disease is AHC.

Yet another aspect of the disclosure provides a use of the nucleic acid expression cassettes, vectors, or compositions thereof for the preparation of a medicament for the treatment or prevention of an ATPase-mediated disease (e.g., AHC).

Yet another aspect of the disclosure provides a kit for the treatment and/or prevention of an ATPase-mediated disease in a subject, the kit comprising a composition of the disclosure and instructions for use.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 6A is an image of neurons in CA1 hippocampal pyramidal layer. FIG. 6B is an image of stratum oriens interneuron of the same mouse.

FIG. 7A shows the CA1 ventral hippocampus. FIG. 7B shows cerebellar Purkinje cells and deep nucleus (insert). Images stained with DAPI (blue). Red color is mCherry. Scale bar is 50 μm. n=3 mice.

FIG. 9A is an image showing hippocampal CA3 region vector transduction (unilateral ICV injection of $20\times10^{10}$ vg). FIG. 9B is an image showing higher magnification image taken from CA3 region, box in FIG. 9A. FIG. 9C is an image showing expression in hippocampal CA1 region after the same ICV dose injected similarly. FIG. 9D is an image showing higher magnification image, also taken from CA1 region, after the same ICV dose injected similarly. FIG. 9E is an image showing trypan blue, 0.4%, staining of cerebellum two hours after intra-cisterna magna (ICM) injection showing robust staining of the cerebellum. FIG. 9F is an image showing cerebellar vector transduction after ICM injection of AAV9-ATP1A3-mcherrry ($15\times10^{10}$ vg). Robust signal, indicating robust viral vector mediated expression, is seen in cerebellar Purkinje cells but not in deeper areas. Scale bar in FIG. 9A, FIG. 9B, and FIG. 9C is 10, in FIG. 9B is 5 μm and FIG. 9E is 20 μm.

FIG. 10A is an image of expression of reporter genes at P40 in hippocampal CA1 region. FIG. 10B is a high power image of the image in FIG. 10A. FIG. 10C is an image of expression of reporter genes in the sensorimotor cortex. FIG. 10D is a magnification of the image in FIG. 10C. FIG. 10E is an image of expression of reporter genes in the cerebellum close to the ICM injection site. FIG. 10F is an image of expression of reporter genes in the cerebellum distant from the ICM injection site. FIG. 10G is an image of expression of reporter genes in the midbrain. FIG. 10H is an image of expression of reporter genes in the thalamus. Scale bars=100 μm (A, C), 10 μm (B, D) and 500 μm (E-H).

DETAILED DESCRIPTION

Figure 1:
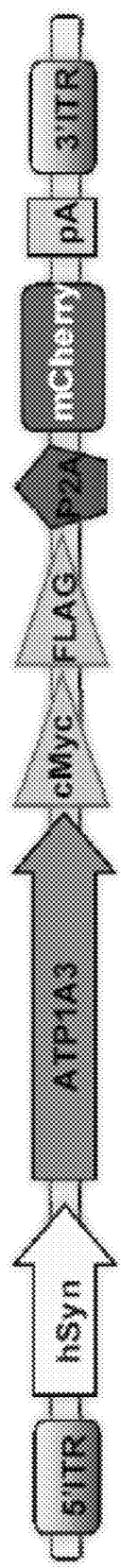
FIG. 1 is a schematic of a representative isolated nucleic acid molecule comprising the following elements: 5' ITR, hSyn promoter, ATP1A3 transgene, cMyc tag, FLAG tag, p2A peptide, mCherry, poly A (pA), and 3' ITR that can be used in the nucleic acid expression cassettes, vectors, and compositions described herein.

For the purposes of promoting an understanding of the principles of the present disclosure, reference will now be made to preferred embodiments and specific language will be used to describe the same. It will nevertheless be understood that no limitation of the scope of the disclosure is thereby intended, such alteration and further modifications of the disclosure as illustrated herein, being contemplated as would normally occur to one skilled in the art to which the disclosure relates.

As used in the specification, articles "a" and "an" are used herein to refer to one or to more than one (i.e., at least one) of the grammatical object of the article. By way of example, "an element" means at least one element and can include more than one element.

"About" is used to provide flexibility to a numerical range endpoint by providing that a given value may be "slightly above" or "slightly below" the endpoint without affecting the desired result. The term "about" in association with a numerical value means that the numerical value can vary plus or minus by 5% or less of the numerical value.

Throughout this specification, unless the context requires otherwise, the word "comprise" and "include" and variations (e.g., "comprises," "comprising," "includes," "including") will be understood to imply the inclusion of a stated component, feature, element, or step or group of components, features, elements or steps but not the exclusion of any other integer or step or group of integers or steps.

As used herein, "and/or" refers to and encompasses any and all possible combinations of one or more of the associated listed items, as well as the lack of combinations where interpreted in the alternative ("or").

As used herein, the transitional phrase "consisting essentially of" (and grammatical variants) is to be interpreted as encompassing the recited materials or steps "and those that do not materially affect the basic and novel characteristic(s)" of the claimed invention. Thus, the term "consisting essentially of" as used herein should not be interpreted as equivalent to "comprising."

Moreover, the present disclosure also contemplates that in some embodiments, any feature or combination of features set forth herein can be excluded or omitted. To illustrate, if the specification states that a complex comprises components A, B and C, it is specifically intended that any of A, B or C, or a combination thereof, can be omitted and disclaimed singularly or in any combination.

Recitation of ranges of values herein are merely intended to serve as a shorthand method of referring individually to each separate value falling within the range, unless otherwise-Indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

Unless otherwise defined, all technical terms used herein have the same meaning as commonly understood by one of ordinary skill in the art to which this disclosure belongs.

Gene Therapy of ATPase-Mediated Diseases

The inventors have developed a knock-in mouse model of the D801N mutation (referred to herein as Mashlool, Mashl, or Mashl$^{+/-}$) that faithfully reproduces the human condition including a response to flunarizine, which is similar to what is observed in humans. In support of using gene therapy to treat genetic ATP1A3 disease is that in the mouse model carrying the, albeit different, I810N ATP1A3 mutation, behavioral abnormalities were rescued by injection of bacterial artificial chromosome (BAC) containing the wild type ATP1A3 gene into pronuclei of fertilized oocytes. This behavioral improvement was associated with a 16% increase in brain-specific Na$^+$, K$^+$-ATPase activity. An alternative approach is to use gene therapy. This approach has proven to be a promising mode of therapy for rare and severe neurogenetic disorders in mouse models and in humans. Gene therapy that may prove to be effective in AHC may have implications on therapy of other neurological disorders of secondary ATPase deficiency such as Alzheimer's disease and Parkinson's disease because in these disorders ATP1A3 dysfunction has been shown to be responsible for neuronal death and degeneration. It has been shown in the above I810N model (Clapcote et al. (2006) *Proc Natl Acad Sci USA*, 106(33): 14085-14090) as well as in the D801N model (240±19, in wild type and 134±25 nmol Pi/min/mg protein, in Mashl mice, n=3 in each group, p=0.002) that mutations of ATP1A3 result in about a 40% reduction in ATPase activity. They also cause abnormal hippocampal firing and behavioral abnormalities in mutant mice (Clapcote et al. (2006) *Proc Natl Acad Sci USA*, 106(33): 14085-14090; Hunanyan et al. (2015) *Epilepsia* 56(1):82-93; Hunanyan et al. (2018) *Epilepsia* 59(7): 1455-1468; Masoud et al. (2017) *Curr Treat Options Neurol.* 19(2):8; Heinzen et al. (2012) *Nat Genet.* 44(9):1030-1034; Helseth et. al. (2018) *Neurobiol Dis.* 119:100-112; Holm et al. (2016) *Biochim Biophys Acta.* 1857(11):1807-1828; Ikeda et al. (2017) *Brain Res.* 1666: 27-37).

Hippocampus is one of the brain regions relevant to the AHC phenotype as human patients (as well as mice) with α-subunit mutations develop seizures of temporal lobe origin and have memory deficits. Another region relevant to the AHC phenotype is the cerebral cortex. Both humans and mice with AHC mutations also manifest neocortical onset seizures, behavioral impairments and cognitive deficits. In addition, basal ganglia, cerebellum and thalamus are involved due to the dystonia, movement control abnormalities and ataxia. The cerebellum is a region of particular interest. This is because patients with AHC invariably have ataxia, often have cerebellar hypometabolism on PET scans and cerebellar atrophy on MRIs and because the cerebellum is involved in the generation of dystonia (Severino et al. (2020) *J Neurol.* 2020 May; 267(5):1300-1311; Ghusayni et al. (2020) *European J Ped Neurol*; February 13:S1090-3798 (20)30032-5; Isaksen et al. (2017) *PLoS Genet.* 13(5): e1006763). The results described herein in the Examples section support the therapeutic effect of gene therapy in the D801N mouse model similar to studies in other neurogenetic disorders. The results described herein is the first demonstration of an effective gene therapy of any ATPase deficiency constituting gene therapy that targets an enzyme, a pump, and a signal transduction factor.

As used herein, the term "ATPase-mediated disease" refers to those diseases and/or disorders characterized by mutations in a gene encoding an ATPase. The term "ATPase" refers to a class of enzymes that catalyze the hydrolysis of phosphate bonds in an adenosine triphosphate (ATP) to form adenosine diphosphate (ADP) or the inverse reaction.

As used herein, the term "ATP1A3-mediated disease" refers to those diseases and/or disorders characterized by mutations in the ATP1A3 gene or by dysfunction of the ATP protein pump.

As used herein, the term "ATP1A3" refers to the ATPase Na+/K+ Transporting subunit alpha 3 [*Homo sapiens* (human)] gene, in which the protein encoded by this gene belongs to the family of P-type cation transport ATPases, and to the subfamily of $Na^+/K^+$-ATPases. The $Na^+/K^+$-ATPase is an integral membrane protein responsible for establishing and maintaining the electrochemical gradients of $Na^+$ and $K^+$ ions across the plasma membrane. According to the present disclosure, ATP1A3 polynucleotides are provided that function along or in combination with additional nucleic acid sequence(s) to encode the ATP1A3 protein.

As used herein, the term "ATP1A3 polynucleotide" is any nucleic acid polymer that encodes an ATP1A3 protein and when present in a vector, plasmid, or translatable construct, expresses such ATP1A3 protein in a cell, tissue, organ or organism. ATP1A3 polynucleotides include precursor molecules, which are expressed inside the cell. ATP1A3 polynucleotides or the processed forms thereof can be contained in a plasmid, vector, genome, or other nucleic acid expression vector for delivery into a cell. In some embodiments, the ATP1A3 polynucleotides are designed as components of AAV viral genomes and packaged in AAV viral particles, which are processed within the cell to express the wild-type ATP1A3 protein.

As used herein, the term "wild-type ATP protein" can be the ATP protein having the UniProtKB No. P13637, or any of the naturally occurring isoforms or variants encoded by the ATP1A3 gene, including any multiple alternatively spliced transcript variants encoding transcript variants encoding different isoforms of ATP1A3. A wild-type ATP1A3 protein can also include an ATP1A3 protein sequence that has at least 70%, 75%, 80%, 85%, or 90% sequence identity to a naturally occurring ATP1A3 protein sequence that retains the same or similar function to the naturally occurring APT1A3 protein.

Mutations in the ATP1A3 gene refer to an alteration in the ATP1A3 polynucleotide sequence as compared to the wild-type ATP1A3 polynucleotide sequence, resulting in the expression of an ATP1A3 protein mutant.

As used herein, the term "ATP1A3 protein mutant" refers to an ATP1A3 protein having an amino acid sequence in which at least one amino acid residue in a wild-type ATP1A3 protein is lost, substituted, or added. Examples of ATP1A3 protein mutants that can be associated with an ATP1A3-mediated disease include, but are not limited to the following mutations: E815K, D801N, G947R, I180N, R756C, V589F, E818K, T613M, E277K, D923N, R756H, V589F, F913del, S137F, S137Y, Q140L, D220N, I274N, I274T, V322D, C333F, T335P, G358C, G358V, I363N, T370N, L371P, S684F, G706R, G755A, G755C, G755S, L757P, I758S, T771I, T771N, S772R, N773I, N773S, F780L, D801E, D801Y, L802P, T804I, D805E, D805H, M806K, 806R, P808L, I810F, I810N, I810S, S811P, L839P, G867D, D923N, C927F, C927Y, A955D, and D992Y and any other disease-causing ATP1A3 protein mutants. In some embodiments, the ATP1A3 protein mutant comprises a D801N mutation.

Mutations in the ATP1A3 gene can cause a variety of neurological diseases, movement disorders and epilepsies. Examples of ATP1A3-mediated diseases include, but are not limited to, rapid-onset dystonia-parkinsonism (RDP), alternating hemiplegia of childhood (AHC), epileptic encephalopathy (EE), cerebellar ataxia, areflexia, pes cavus, optic atrophy and sensorineural hearing loss (CAPOS) syndrome, fever induced paroxysmal weakness and encephalopathy (FIPWE, also called RECA or Relapsing Encephalopathy with Cerebellar Ataxia), recurrent episodes of cerebellar ataxia (RECA), early-onset schizophrenia, Dystonia Dysmorphism of the face Encephalopathy MRI abnormalities without hemiplegia (D-DEMO) syndrome and Childhood Rapid Onset ataxia (CROA). In some embodiments, this could include other diseases that are likely to be described in the future as being caused by other ATP1A3 mutations or caused by abnormalities in ATP1A3 protein structure or function. In some embodiments, the ATP1A3-mediated disease comprises Alternating Hemiplegia of Childhood (AHC), epilepsy, stroke, hypoglycemia acute ataxia, dystonia and neuronal death in neurodegenerative diseases including Alzheimer's and Parkinson's diseases. In some embodiments, the use of a vector comprising an ATP1A3 transgene (e.g., AAV9-specific promoter-ATP1A3-FLAG-p2a-Cherry-SV40polyA) or a related construct can include therapy of disorders resulting from mutations of other ATPases that may benefit from the ATP1A3 vector that is targeted at the specific tissue of that disorder. An example of that can include kidney diseases caused by decreased function of the V-ATPase due to mutations in the ATP6V1B1 or ATP6V0A4 ATPase genes.

In some embodiments, the nucleic acid expression cassettes, vectors or related construct of the disclosure can include ATPase-mediated diseases resulting from mutations of other ATPase genes leading to other ATPase deficiencies. In such cases, the transgene can be the relevant ATPase for that disease and the promoter can be one that is capable of driving expression of the ATPase gene in a relevant organ system or cell. Examples of ATPase-mediated diseases include immunodeficiency disorders caused by ATP6A1 mutations, liver disease caused by ATP7A or ATP7B mutations. Another example is central nervous system disorders such as hemiplegic migraine or epileptic encephalopathy that result from ATP1A2 mutations, or peripheral neuropathy and hypomagnesemia/intellectual disability syndrome caused by ATP1A1 mutations. Other examples include mutations to the ATPase genes that cause muscle disease such as Myosin and ATP2A1 genes or mutations causing hematologic diseases such as mutations in ATP11C and ATP2C1 mutations that cause skin disease.

In some embodiments, the use of the nucleic acid expression cassettes, active vectors or related constructs can include disorders resulting from other disease states leading to symptoms caused by dysfunction of any ATPase. In such cases, the transgene can be the relevant ATPase for that disease and the promoter can be one that is capable of driving expression of the ATPase gene in a pertinent organ system or cell. Examples of such diseases would be VMA21 gene mutations resulting in secondary V-ATPase misassembly and dysfunction of the V-ATPase as seen in congenital disorder of glycosylation with autophagic liver disease and WDR72 gene mutations that results in abnormal trafficking of kidney V-ATPase and secondary kidney disease. Another includes inflammatory bowel disease with secondary abnormal ATPase function due to chronic mucosal inflammation resulting in gastrointestinal symptoms.

Nucleic Acid Expression Cassettes

The present disclosure provides, in part, a nucleic acid expression cassette comprising, consisting of, or consisting essentially of a nucleic acid sequence encoding an ATPase (e.g., ATP1A3).

As used herein, the term "nucleic acid expression cassette" refers to an isolated nucleic acid molecule that includes one or more transcriptional control elements (e.g., promoters, enhancers, and/or regulatory elements, polyadenylation sequences, and introns) that direct gene expression in one or more desired cell types, tissues or organs. A nucleic acid expression cassette can contain a transgene, although it is also envisaged that a nucleic acid expression cassette directs expression of an endogenous gene in a cell into which the nucleic acid sequence is inserted.

As used herein, the term "transgene" refers to exogenous nucleic acid sequences that encode a polypeptide to be expressed in a cell into which the transgene is introduced. A transgene can include a heterologous nucleic acid sequence that is not naturally found in the cell into which it has been introduced, a nucleic acid sequence that is a mutant form of a nucleic acid sequence naturally found in the cell into which it has been introduced, or a nucleic acid sequence that is the same as a naturally occurring nucleic in the cell into which it has been introduced. A transgene can include genes from the same organism into which it is introduced or from a different organism.

A transgene of the disclosure can include, but is not limited to, ATP1A1, ATP1A2, ATP1A3, ATP1A4, ATP1B1, ATP1B2, ATP1B3, ATP1B4, ATP2A1, ATP2A2, ATP2A3, ATP2B1, ATP2B2, ATP2B3, ATP2B4, ATP2C1, ATP2C2, ATP3, ATP4, ATP5A1, ATP5B, ATP5C1, ATP5C2, ATP5D, ATP5E, ATP5F1, ATP5G1, ATP5G2, ATP5G3, ATP5H, ATP5I, ATP5J, ATP5J2, ATP5L, ATP5L2, ATP5O, ATP5S, ATP6A1, ATP6AP1, ATP6AP2, ATP6V1A, ATP6V1B1, ATP6V1B2, ATP6V1C1, ATP6V1C2, ATP6V1D, ATP6V1E1, ATP6V1E2, ATP6V1F, ATP6V1G1, ATP6V1G2, ATP6V1G3, ATP6V1H, ATP6V0A1, ATP6V0A2, ATP6V0A4, ATP6V0B, ATP6V0C, ATP6V0D1, ATP6V0D2, ATP6V0E, ATP11C, ATP7A, ATP7B, ATP8A1, ATP8B1, ATP8B2, ATP8B3, ATP8B4, ATP9A, ATP9B, ATP10A, ATP10B, ATP10D, ATP11A, ATP11B, ATP11C, ATP12A, ATP13A1, ATP13A2, ATP13A3, ATP13A4, ATP13A5, VMA21, V-ATPase, or WDR72 or any gene encoding an ATPase. In some embodiments, the transgene is a nucleic acid sequence encoding ATP1A3.

The term "nucleic acid sequence," "nucleic acid molecule," "polynucleotide," and "oligonucleotide" are used interchangeably and refer to a polymeric form of nucleotides that may have various lengths, either deoxyribonucleotides or ribonucleotides, or analogs thereof. Nucleic acid molecules can be deoxyribonucleic acid (DNA) or ribonucleic acid (RNA) fragments generated, for example, by a polymerase chain reaction (PCR) or by in vitro translation, and fragments generated by any one or more of ligation, scission, endonuclease action, or exonuclease action. Nucleic acid molecules can be composed of monomers that are naturally occurring nucleotides (such as deoxyribonucleotides and ribonucleotides), analogs of naturally occurring nucleotides (e.g., α-enantiomeric forms of naturally-occurring nucleotides), or a combination thereof. Modified nucleotides can have modifications in or replacement of sugar moieties, or pyrimidine or purine base moieties. Nucleic acid monomers can be linked by phosphodiester bonds or analogs of such linkages. Analogs of phosphodiester linkages include phosphorothioate, phosphorodithioate, phosphoroselenoate, phosphorodiselenoate, phosphoroanilothioate, phosphoranilidate, phosphoramidate, morpholino, or the like. Nucleic acid molecules can be either single stranded or double stranded (e.g., ssDNA, dsDNA, ssRNA, or dsRNA).

The term "nucleotide" refers to sequences with conventional nucleotide bases, sugar residues and internucleotide phosphate linkages, but also to those that contain modifications of any or all of these moieties. The term "nucleotide" as used herein includes those moieties that contain not only the natively found purine and pyrimidine bases adenine (A), guanine (G), thymine (T), cytosine (C), and uracil (U), but also modified or analogous forms thereof. Polynucleotides include RNA and DNA sequences of more than one nucleotide in a single chain. Modified RNA or modified DNA, as used herein, refers to a nucleic acid molecule in which one or more of the components of the nucleic acid, namely sugars, bases, and phosphate moieties, are different from that which occurs in nature.

As used herein, the term "isolated" nucleic acid molecule (e.g., an isolated DNA, isolated cDNA, or an isolated vector genome) means a nucleic acid molecule separated or substantially free from at least some of the other components of the naturally occurring organism or virus, for example, the cell or viral structural components or other polypeptides or nucleic acids commonly found associated with the nucleic acid.

Likewise, an "isolated" polypeptide means a polypeptide that is separated or substantially free from at least some of the other components of the naturally occurring organism or virus, for example, the cell or viral structural components or other polypeptides or nucleic acids commonly found associated with the polypeptide.

In some embodiments, the nucleic acid sequence encoding ATP1A3 is provided in ensemble.org (HGNC ID: HGNC:801, encoding the ATP1A3 protein corresponding to UniProtKB identifier P13637) as set forth in SEQ ID NO:01, and any fragments, isoforms, and/or homologues thereof. In another embodiment, the nucleic acid sequence encoding ATP1A3 comprises a cDNA nucleic acid sequence as set forth in SEQ ID NO:02, and any fragments, isoforms, or homologues thereof. In another embodiment, the nucleic acid sequence encoding ATP1A3 comprises a nucleic acid sequence as set forth in SEQ ID NO:07, and any fragments, isoforms, or homologues thereof.

In other embodiments, the nucleic acid sequence encoding ATP1A3 can be any of the nucleic acid sequences set forth in the following GenBank Accession Numbers: BC009282.2, BC015566.2, AK295078.1, AK296557.1, AK295833.1, AK316069.1, BC013763.1, KJ896471.1, JF432325.1, KR710324.1, KR710323.1, or KR710322.1 or NCBI Accession Numbers: NM_152296.5, XM_016934231.2, NM_001256213.1, XM_004060817.3, NM_001256214.2, or AK223569.1. In other embodiments, the nucleic acid sequence encodes a wild-type ATP1A3 protein having the amino acid sequence set forth in SEQ ID NO:03 (NCBI Reference Sequence: P13637-1) or the amino acid sequence set forth in SEQ ID NO:06, or a sequence having at least 50%, 60%, 70%, 80%, 85%, 86%, 87%, 88%, 89%, 90%, 91%, 92%, 93%, 94%, 95%, 96%, 97%, 98%, or 99% sequence identity to the sequence set forth in SEQ ID NO:03 or SEQ ID NO:06.

Table 1 provides exemplary sequences that are related to the transgenes of the present disclosure.

TABLE 1

| Nucleic Acid and Amino Acid Sequences | |
|---|---|
| Representative Nucleic acid sequence encoding ATP1A3 | ATGGGGGACAAGAAAGATGACAAGGACTCACCCAAGAAGAACAAGGGCAAGGAGCGCCGGGAC<br>CTGGATGACCTCAAGAAGGAGGTGGCTATGACAGAGCACAAGATGTCAGTGGAAGAGGTCTGC<br>CGGAAATACAACACAGACTGTGTGCAGGGTTTGACCCACAGCAAAGCCCAGGAGATCCTGGCC<br>CGGGATGGGCCTAACGCACTCACGCCACCGCCTACCACCCCAGAGTGGGTCAAGTTTTGCCGG<br>CAGCTCTTCGGGGGCTTCTCCATCCTGCTGTGGATCGGGGCTATCCTCTGCTTCCTGGCCTAC<br>GGTATCCAGGCGGGCACCGAGGACGACCCCTCTGGTGACAACCTGTACCTGGGCATCGTGCTG<br>GCGGCCGTGGTGATCATCACTGGCTGCTTCTCCTACTACCAGGAGGCCAAGAGCTCCAAGATC<br>ATGGAGTCCTTCAAGAACATGGTGCCCCAGCAAGCCCTGGTGATCCGGGAAGGTGAGAAGATG<br>CAGGTGAACGCTGAGGAGGTGGTGGTCGGGGACCTGGTGGAGATCAAGGGTGGAGACCGAGTG<br>CCAGCTGACCTGCGGATCATCTCAGCCCACGGCTGCAAGGTGGACAACTCCTCCCTGACTGGC<br>GAATCCGAGCCCCAGATCGCTCTCCCGACTGCACGCACGACAACCCCTTGGAGACTCGGAAC<br>ATCACCTTCTTTTCCACCAACTGTGTGGAAGGCACGGCTCGGGGCGTGGTGGTGGCCACGGGC<br>GACCGCACTGTCATGGGCCGTATCGCCACCCTGGCATCAGGGCTGGAGGTGGGCAAGACGCCC<br>ATCGCCATCGAGATTGAGCACTTCATCCAGCTCATCACCGGCGTGGCTGTCTTCCTGGGTGTC<br>TCCTTCTTCATCCTCTCCCTCATTCTCGGATACACCTGGCTTGAGGCTGTCATCTTCCTCATC<br>GGCATCATCGTGGCCAATGTCCCAGAGGGTCTGCTGGCCACTGTCACTGTGTGTCTGACGCTG<br>ACCGCCAAGCGCATGGCCCGGAAGAACTGCCTGGTGAAGAACCTGGAGGCTGTAGAAACCCTG<br>GGCTCCACGTCCACCATCTGCTCAGATAAGACAGGGACCCTCACTCAGAACCGCATGACAGTC<br>GCCCACATGTGGTTTGACAACCAGATCCACGAGGCTGACACCACTGAGGACCAGTCAGGGACC<br>TCATTTGACAAGAGTTCGCACACCTGGGTGGCCCTGTCTCACATCGCTGGGCTCTGCAATCGC<br>GCTGTCTTCAAGGGTGGTCAGGACAACATCCCTGTGCTCAAGAGGGATGTGGCTGGGGATGCG<br>TCTGAGTCTGCCCTGCTCAAGTGCATCGAGCTGTCCTCTGGCTCCGTGAAGCTGATGCGTGAA<br>CGCAACAAGAAAGTGGCTGAGATTCCCTTCAATTCCACCAACAAATACCAGCTCTCCATCCAT<br>GAGACCGAGGACCCCAACGACAACCGATACCTGCTGGTGATGAAGGGTGCCCCGAGCGCATC<br>CTGGACCGCTGCTCCACCATCCTGCTACAGGGCAAGGAGCAGCCTCTGGACGAGGAAATGAAG<br>GAGGCCTTCCAGAATGCCTACCTTGAGCTCGGTGGCCTGGGCGAGCGCGTGCTTGGTTTCTGC<br>CATTATTACCTGCCCGAGGAGCAGTTCCCCAAGGGCTTTGCCTTCGACTGTGATGACGTGAAC<br>TTCACCACGGACAACCTCTGCTTTGTGGGCCTCATGTCCATGATCGACCCACCCCGGGCAGCC<br>GTCCCTGACGCGGTGGGCAAGTGTCGCAGCGCAGGCATCAAGGTCATCATGGTCACCGGCGAT<br>CACCCCATCACGGCCAAGGCCATTGCCAAGGGTGTGGGCATCATCTCTGAGGGCAACGAGACT<br>GTGGAGGACATCGCCGCCCGGCTCAACATTCCCGTCAGCCAGGTTAACCCCCGGGATGCCAAG<br>GCCTGCGTGATCCACGGCACCGACCTCAAGGACTTCACCTCCGAGCAAATCGACGAGATCCTG<br>CAGAATCACACCGAGATCGTCTTCGCCCGCACATCCCCCCAGCAGAAGCTCATCATTGTGGAG<br>GGCTGTCAGAGACAGGGTGCAATTGTGGCTGTGACCGGGGATGGTGTGAACGACTCCCCCGCT<br>CTGAAGAAGGCCGACATTGGGGTGGCCATGGGCATCGCTGGCTCTGACGTCTCCAAGCAGGCA<br>GCTGACATGATCCTGCTGGACGACAACTTTGCCTCCATCGTCACAGGGGTGGAGGAGGGCCGC<br>CTGATCTTCGACAACCTAAAGAAGTCCATTGCCTACACCCTGACCAGCAATATCCCGGAGATC<br>ACGCCCTTCCTGCTGTTCATCATGGCCAACATCCCGCTGCCCCTGGGCACCATCACCATCCTC<br>TGCATCGATCTGGGCACTGACATGGTCCCTGCCATCTCACTGGCGTACGAGGCTGCCGAAAGC<br>GACATCATGAAGAGACAGCCCAGGAACCCGCGGACGGACAAATTGGTCAATGAGAGACTCATC<br>AGCATGGCCTACGGGCAGATTGGAATGATCCAGGCTCTCGGTGGCTTCTTCTCTTACTTTGTG<br>ATCCTGGCAGAAAATGGCTTCTTGCCCGGCAACCTGGTGGGCATCCGGCTGAACTGGGATGAC<br>CGCACCGTCAATGACCTGGAAGACAGTTACGGGCAGCAGTGGACATACGAGCAGAGGAAGGTG<br>GTGGAGTTCACCTGCCACACGGCCTTCTTTGTGAGCATCGTTGTCGTCCAGTGGGCCGATCTG<br>ATCATCTGCAAGACCCGGAGGAACTCGGTCTTCCAGCAGGGCATGAAGAACAAGATCCTGATC<br>TTCGGGCTGTTTGAGGAGACGGCCCTGGCTGCCTTCCTGTCCTACTGCCCCGGCATGGACGTG<br>GCCCTGCGCATGTACCCTCTCAAGCCCAGCTGGTGGTTCTGTGCCTTCCCCTACAGTTTCCTC<br>ATCTTCGTCTACGACGAAATCCGCAAACTCATCCTGCGCAGGAACCCAGGGGGTTGGGTGGAG<br>AAGGAAA (SEQ ID NO: 07) |
| Representative nucleic acid sequence encoding ATP1A3 | CGCGCGCACCTACCGAGGCGCGGGCGCTGCAGAGGCTCCCAGCCCAAGCCTGAGCCTGAGCCC<br>GCCCCGAGGTCCCCGCCCCGCCCGCCTGGCTCTCTCGCCGCGGAGCCGCCAAGATGGGGGACA<br>AGAAAGATGACAAGGACTCACCCAAGAAGAACAAGGGCAAGGAGCGCCGGGACCTGGATGACC<br>TCAAGAAGGAGGTGGCTATGACAGAGCACAAGATGTCAGTGGAAGAGGTCTGCCGGAAATACA<br>ACACAGACTGTGTGCAGGGTTTGACCCACAGCAAAGCCCAGGAGATCCTGGCCCGGGATGGGC<br>CTAACGCACTCACGCCACCGCCTACCACCCCAGAGTGGGTCAAGTTTTGCCGGCAGCTCTTCG<br>GGGGCTTCTCCATCCTGCTGTGGATCGGGGCTATCCTCTGCTTCCTGGCCTACGGTATCCAGG<br>CGGGCACCGAGGACGACCCCTCTGGTGACAACCTGTACCTGGGCATCGTGCTGGCGGCCGTGG<br>TGATCATCACTGGCTGCTTCTCCTACTACCAGGAGGCCAAGAGCTCCAAGATCATGGAGTCCT<br>TCAAGAACATGGTGCCCCAGCAAGCCCTGGTGATCCGGGAAGGTGAGAAGATGCAGGTGAACG<br>CTGAGGAGGTGGTGGTCGGGGACCTGGTGGAGATCAAGGGTGGAGACCGAGTGCCAGCTGACC<br>TGCGGATCATCTCAGCCCACGGCTGCAAGGTGGACAACTCCTCCCTGACTGGCGAATCCGAGC<br>CCCAGACTCGCTCTCCCGACTGCACGCACGACAACCCCTTGGAGACTCGGAACATCACCTTCT<br>TTTCCACCAACTGTGTGGAAGGCACGGCTCGGGGCGTGGTGGTGGCCACGGGCGACCGCACTG<br>TCATGGGCCGTATCGCCACCCTGGCATCAGGGCTGGAGGTGGGCAAGACGCCCATCGCCATCG<br>AGATTGAGCACTTCATCCAGCTCATCACCGGCGTGGCTGTCTTCCTGGGTGTCTCCTTCTTCA<br>TCCTCTCCCTCATTCTCGGATACACCTGGCTTGAGGCTGTCATCTTCCTCATCGGCATCATCG<br>TGGCCAATGTCCCAGAGGGTCTGCTGGCCACTGTCACTGTGTGTCTGACGCTGACCGCCAAGC<br>GCATGGCCCGGAAGAACTGCCTGGTGAAGAACCTGGAGGCTGTAGAAACCCTGGGCTCCACGT<br>CCACCATCTGCTCAGATAAGACAGGGACCCTCACTCAGAACCGCATGACAGTCGCCCACATGT<br>GGTTTGACAACCAGATCCACGAGGCTGACACCACTGAGGACCAGTCAGGGACCTCATTTGACA |

TABLE 1-continued

Nucleic Acid and Amino Acid Sequences

```
AGAGTTCGCACACCTGGGTGGCCCTGTCTCACATCGCTGGGCTCTGCAATCGCGCTGTCTTCA
AGGGTGGTCAGGACAACATCCCTGTGCTCAAGAGGGATGTGGCTGGGGATGCGTCTGAGTCTG
CCCTGCTCAAGTGCATCGAGCTGTCCTCTGGCTCCGTGAAGCTGATGCGTGAACGCAACAAGA
AAGTGGCTGAGATTCCCTTCAATTCCACCAACAAATACCAGCTCTCCATCCATGAGACCGAGG
ACCCCAACGACAACCGATACCTGCTGGTGATGAAGGGTGCCCCCGAGCGCATCCTGGACCGCT
GCTCCACCATCCTGCTACAGGGCAAGGAGCAGCCTCTGGACGAGGAAATGAAGGAGGCCTTCC
AGAATGCCTACCTTGAGCTCGGTGGCCTGGGCGAGCGCGTGCTTGGTTTCTGCCATTATTACC
TGCCCGAGGAGCAGTTCCCCAAGGGCTTTGCCTTCGACTGTGATGACGTGAACTTCACCACGG
ACAACCTCTGCTTTGTGGGCCTCATGTCCATGATCGACCCACCCCGGGCAGCCGTCCCTGACG
CGGTGGGCAAGTGTCGCAGCGCAGGCATCAAGGTCATCATGGTCACCGGCGATCACCCCATCA
CGGCCAAGGCCATTGCCAAGGGTGTGGGCATCATCTCTGAGGGCAACGAGACTGTGGAGGACA
TCGCCGCCCGGCTCAACATTCCCGTCAGCCAGGTTAACCCCCGGGATGCCAAGGCCTGCGTGA
TCCACGGCACCGACCTCAAGGACTTCACCTCCGAGCAAATCGACGAGATCCTGCAGAATCACA
CCGAGATCGTCTTCGCCCGCACATCCCCCCAGCAGAAGCTCATCATTGTGGAGGGCTGTCAGA
GACAGGGTGCAATTGTGGCTGTGACCGGGGATGGTGTGAACGACTCCCCCGCTCTGAAGAAGG
CCGACATTGGGGTGGCCATGGGCATCGCTGGCTCTGACGTCTCCAAGCAGGCAGCTGACATGA
TCCTGCTGGACGACAACTTTGCCTCCATCGTCACAGGGGTGGAGGAGGGCCGCCTGATCTTCG
ACAACCTAAAGAAGTCCATTGCCTACACCCTGACCAGCAATATCCCGGAGATCACGCCCTTCC
TGCTGTTCATCATGGCCAACATCCCGCTGCCCCTGGGCACCATCACCATCCTCTGCATCGATC
TGGGCACTGACATGGTCCCTGCCATCTCACTGGCGTACGAGGCTGCCGAAAGCGACATCATGA
AGAGACAGCCCAGGAACCCGCGGACGGACAAATTGGTCAATGAGAGACTCATCAGCATGGCCT
ACGGGCAGATTGGAATGATCCAGGCTCTCGGTGGCTTCTTCTCTTACTTTGTGATCCTGGCAG
AAAATGGCTTCTTGCCCGGCAACCTGGTGGGCATCCGGCTGAACTGGGATGACCGCACCGTCA
ATGACCTGGAAGACAGTTACGGGCAGCAGTGGACATACGAGCAGAGGAAGGTGGTGGAGTTCA
CCTGCCACACGGCCTTCTTTGTGAGCATCGTTGTCGTCCAGTGGGCCGATCTGATCATCTGCA
AGACCCGGAGGAACTCGGTCTTCCAGCAGGGCATGAAGAACAAGATCCTGATCTTCGGGCTGT
TTGAGGAGACGGCCCTGGCTGCCTTCCTGTCCTACTGCCCCGGCATGGACGTGGCCCTGCGCA
TGTACCCTCTCAAGCCCAGCTGGTGGTTCTGTGCCTTCCCCTACAGTTTCCTCATCTTCGTCT
ACGACGAAATCCGCAAACTCATCCTGCGCAGGAACCCAGGGGGTTGGGTGGAGAAGGAAACCT
ACTACTGACCTCAGCCCCACCACATCGCCCATCTCTTCCCCGTCCCGCAGGCCCAGGACCGCC
CCTGTCAGTCCCCCCAATTTTGTATTCTGGGGGGAGGAGCCCTCTCTTCCTGTGGCCCCACCT
TGGCCCCACCCCCTCCACTATCTCCTGCCGCCCCCACTCTGGCTGGCTTCTCTCCCCTGCCC
CAAACCTCTCTCCTCTCTTTTCTGTGTCAGTTTCTCTCCCTCTCCTCACCCCTCTATCCAT
TCCTCCCGCCCCAGCCACCTCCCTGGGCTCTTTTTTACTCCCCTTCAGCCCCCCGGCTGATGC
CATCTCTGGTTCTGGACAATTATCAAATATATCAGTGGGGAGAGAGAAAAAAAAAAAAAAAAA
AAAAAAAAAAAAAAAAAAAAAAAA (SEQ ID NO: 02)
```

| Representative amino acid sequence for ATP1A3 | MGDKKDDKDS PKKNKGKERR DLDDLKKEVA MTEHKMSVEE VCRKYNTDCV<br>QGLTHSKAQE ILARDGPNAL TPPPTTPEWV KFCRQLFGGF SILLWIGAIL<br>CFLAYGIQAG TEDDPSGDNL YLGIVLAAVV IITGCFSYYQ EAKSSKIMES<br>FKNMVPQQAL VIREGEKMQV NAEEVVVGDL VEIKGGDRVP ADLRIISAHG<br>CKVDNSSLTG ESEPQTRSPD CTHDNPLETR NITFFSTNCV EGTARGVVVA<br>TGDRTVMGRI ATLASGLEVG KTPIAIEIEH FIQLITGVAV FLGVSFFILS<br>LILGYTWLEA VIFLIGIIVA NVPEGLLATV TVCLTLTAKR MARKNCLVKN<br>LEAVETLGST STICSDKTGT LTQNRMTVAH MWFDNQIHEA DTTEDQSGTS<br>FDKSSHTWVA LSHIAGLCNR AVFKGGQDNI PVLKRDVAGD ASESALLKCI<br>ELSSGSVKLM RERNKKVAEI PFNSTNKYQL SIHETEDPND NRYLLVMKGA<br>PERILDRCST ILLQGKEQPL DEEMKEAFQN AYLELGGLGE RVLGFCHYYL<br>PEEQFPKGFA FDCDDVNFTT DNLCFVGLMS MIDPPRAAVP DAVGKCRSAG<br>IKVIMVTGDH PITAKAIAKG VGIISEGNET VEDIAARLNI PVSQVNPRDA<br>KACVIHGTDL KDFTSEQIDE ILQNHTEIVF ARTSPQQKLI IVEGCQRQGA<br>IVAVTGDGVN DSPALKKADI GVAMGIAGSD VSKQAADMIL LDDNFASIVT<br>GVEEGRLIFD NLKKSIAYTL TSNIPEITPF LLFIMANIPL PLGTITILCI<br>DLGTDMVPAI SLAYEAAESD IMKRQPRNPR TDKLVNERLI SMAYGQIGMI<br>QALGGFFSYF VILAENGFLP GNLVGIRLNW DDRTVNDLED SYGQQWTYEQ<br>RKVVEFTCHT AFFVSIVVVQ WADLIICKTR RNSVFQQGMK NKILIFGLFE<br>ETALAAFLSY CPGMDVALRM YPLKPSWWFC AFPYSFLIFV YDEIRKLILR<br>RNPGGWVEKE TYY (SEQ ID NO: 03) |
|---|---|
| Representative amino acid sequence for ATP1A3 | MGDKKDDKDSPKKNKGKERRDLDDLKKEVAMTEHKMSVEEVCRKYNTDCVQGLTHSKAQEILA<br>RDGPNALTPPPTTPEWVKFCRQLFGGFSILLWIGAILCFLAYGIQAGTEDDPSGDNLYLGIVL<br>AAVVIITGCFSYYQEAKSSKIMESFKNMVPQQALVIREGEKMQVNAEEVVVGDLVEIKGGDRV<br>PADLRIISAHGCKVDNSSLTGESEPQTRSPDCTHDNPLETRNITFFSTNCVEGTARGVVVATG<br>DRTVMGRIATLASGLEVGKTPIAIEIEHFIQLITGVAVFLGVSFFILSLILGYTWLEAVIFLI<br>GIIVANVPEGLLATVTVCLTLTAKRMARKNCLVKNLEAVETLGSTSTICSDKTGTLTQNRMTV<br>AHMWFDNQIHEADTTEDQSGTSFDKSSHTWVALSHIAGLCNRAVFKGGQDNIPVLKRDVAGDA<br>SESALLKCIELSSGSVKLMRERNKKVAEIPFNSTNKYQLSIHETEDPNDNRYLLVMKGAPERI<br>LDRCSTILLQGKEQPLDEEMKEAFQNAYLELGGLGERVLGFCHYYLPEEQFPKGFAFDCDDVN<br>FTTDNLCFVGLMSMIDPPRAAVPDAVGKCRSAGIKVIMVTGDHPITAKAIAKGVGIISEGNET<br>VEDIAARLNIPVSQVNPRDAKACVIHGTDLKDFTSEQIDEILQNHTEIVFARTSPQQKLIIVE<br>GCQRQGAIVAVTGDGVNDSPALKKADIGVAMGIAGSDVSKQAADMILLDDNFASIVTGVEEGR<br>LIFDNLKKSIAYTLTSNIPEITPFLLFIMANIPLPLGTITILCIDLGTDMVPAISLAYEAAES<br>DIMKRQPRNPRTDKLVNERLISMAYGQIGMIQALGGFFSYFVILAENGFLPGNLVGIRLNWDD<br>RTVNDLEDSYGQQWTYEQRKVVEFTCHTAFFVSIVVVQWADLIICKTRRNSVFQQGMKNKILI<br>FGLFEETALAAFLSYCPGMDVALRMYPLKPSWWFCAFPYSFLIFVYDEIRKLILRRNPGGWVE<br>KE (SEQ ID NO: 06) |

As provided herein and in accordance with one embodiment of the present disclosure, the nucleic acid sequence encoding ATP1A3 can comprise a sequence which has a sequence identity to any of SEQ ID NO:01, SEQ ID NO:02, or SEQ ID NO:07. The nucleic acid sequence encoding ATP1A3 can have 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 99% or 100% identity to the nucleic acid sequences set forth in SEQ ID NO:01, SEQ ID NO:02, or SEQ ID NO:07. The nucleic acid sequence encoding ATP1A3 can have 1-10%, 10-20%, 30-40%, 50-60%, 50-70%, 50-80%, 50-90%, 50-99%, 50-100%, 60-70%, 60-80%, 60-90%, 60-99%, 60-100%, 70-80%, 70-90%, 70-99%, 70-100%, 80-85%, 80-90%, 80-95%, 80-99%, 80-100%, 90-95%, 90-99%, or 90-100% to the nucleic acid sequences set forth in SEQ ID NO:01, SEQ ID NO:02, or SEQ ID NO:07. As a non-limiting example, the nucleic acid sequence encoding ATP1A3 can comprise a sequence which has 80% identity to the nucleic acid sequences set forth in SEQ ID NO:01, SEQ ID NO:02, or SEQ ID NO:07. As another non-limiting example, the nucleic acid sequence encoding ATP1A3 can comprise a sequence which has 85% identity to the nucleic acid sequences set forth in SEQ ID NO:01, SEQ ID NO:02, or SEQ ID NO:07. As another non-limiting example, the nucleic acid sequence encoding ATP1A3 can comprise a sequence which has 90% identity to the nucleic acid sequences set forth in SEQ ID NO:01, SEQ ID NO:02, or SEQ ID NO:07. As another non-limiting example, the nucleic acid sequence encoding ATP1A3 can comprise a sequence which has 95% identity to the nucleic acid sequences set forth in SEQ ID NO:01, SEQ ID NO:02, or SEQ ID NO:07. As another non-limiting example, the nucleic acid sequence encoding ATP1A3 can comprise a sequence which has 99% identity to the nucleic acid sequences set forth in SEQ ID NO:01, SEQ ID NO:02, or SEQ ID NO:07.

In another embodiment, the expression cassette comprises, consists of, or consists essentially of a transgene that encodes mRNA that can be translated into an amino sequence encoding the protein for ATP1A3. In some embodiment, the nucleic acid sequence encoding ATP1A3 is a cDNA sequence that has the sequence set forth in SEQ ID NO:02, or fragments, isoforms, or homologues thereof.

The term "sequence identity" refers to the number of identical or similar residues (i.e., nucleotide bases or amino acid) on a comparison between a test and reference nucleotide or amino acid sequence. Sequence identity can be determined by sequence alignment of nucleic acid to identify regions of similarity or identity. As described herein, sequence identity is generally determined by alignment to identify identical residues. Matches, mismatches, and gaps can be identified between compared sequences. Alternatively, sequence identity can be determined without taking into account gaps as the number of identical positions/length of the total aligned sequence×100. In one non-limiting embodiment, the term "at least 90% sequence identity to" refers to percent identities from 90 to 100%, relative to the reference nucleotide or amino acid sequence. Identity at a level of 90% or more is indicative of the fact that, assuming for exemplary purposes a test and reference oligonucleotide or length of 100 nucleotides are compared, no more than 10% (i.e., 10 out of 100) of the nucleotides in the test oligonucleotide differ from those of the reference oligonucleotide. Differences are defined as nucleic acid or amino acid substitutions, insertions, or deletions.

In some embodiments, the expression cassette comprises a nucleotide sequence encoding ATP1A3 that is codon-optimized to reduce CpG methylation sites and for mammalian expression (e.g., human cell expression). In other embodiments, the nucleic acid expression cassette does not contain codon optimized nucleic acid sequences.

The term "codon optimized" relates to the alteration of codons in nucleic acid molecules to reflect the typical codon usage of the host organism (e.g., mammals such as humans) without altering the polypeptide encoded by the DNA, to improve expression. Many methods and software tools for codon optimization have been reported previously. See, for example, genomes.urv.es/OPTIMIZER/; Puigbò et al., *Nucleic Acids Res.* (2007) (Web Server issue): W126-W131; Chin et al. (2014) *Bioinformatics*, 30(15):2210-2; Fuglsang, (2003) *Protein Expr. Purif.,* 31(2):247-9; Narum et al., (2001) *Infect. Immun.,* 69(12):7250-7253, Outchkourov et al., (2002) *Protein Expr. Purif,* 24(1):18-24, Humphreys et al., (2000) *Protein Expr. Purif.,* 20(2):252-64.

Those of ordinary skill in the art will appreciate that the nucleic acid expression cassette comprising a nucleic acid encoding ATP1A3 can contain transcription/translation control signals or secretory signal sequences, which can be included in the nucleic acid expression cassette or by a vector backbone. For example, specific initiation signals can be required for efficient translation of inserted protein coding sequences. These exogenous translational control sequences, which can include the ATG initiation codon and adjacent sequences, can be of a variety of origins, both natural and synthetic.

A variety of promoter/enhancer elements can be used depending on the level and tissue-specific expression desired. The promoter can be tissue-specific or ubiquitous and can be constitutive or inducible, depending on the pattern of the gene expression desired. The promoter can be native or foreign and can be a natural or a synthetic sequence. By foreign, it is intended that the transcriptional initiation region is not found in the wild-type host into which the transcriptional initiation region is introduced.

The promoter can be chosen so that it will function in the target cell(s) of interest. Tissue-specific promoters refer to promoters that have activity in only certain cell types. The use of a tissue-specific promoter in a nucleic acid expression cassette can restrict unwanted transgene expression in the unaffected tissues as well as facilitate persistent transgene expression by escaping from transgene induced host immune responses. Tissue specific promoters include, but are not limited to, neuron-specific promoters, muscle-specific promoters, liver-specific promoters, skeletal muscle-specific promoters, and heart-specific promoters.

Neuron-specific promoters include, but are not limited to, the synapsin I (SYN) promoter, the calcium/calmodulin-dependent protein kinase II promoter, the tubulin alpha I promoter, the neuron-specific enolase promoter, and the platelet-derived growth factor beta chain promoter. In some embodiments, the neuron-specific promoter is a human synapsin promoter. In other embodiments, the neuron-specific promoter is the human synapsin promoter has the nucleic acid sequence that is set forth in SEQ ID NO:04 or SEQ ID NO:09 human promoter sequence or the mouse promoter sequence set forth in SEQ ID NO:08. In other embodiments, the human synapsin promoter comprises the proximal region of the synapson 1 promoter (−422 to −22). In some embodiments, the proximal region of the synapsin 1 promoter (−422 to −22) has the nucleic acid sequence that is set forth in SEQ ID NO:05.

Liver-specific promoters include, but are not limited to, the α1-microglobulin/bikunin enhancer/thyroid hormone-binding globulin promoter, the human albumin (hALB) promoter, the thyroid hormone-binding globulin promoter, the α-1-antitrypsin promoter, the bovine albumin (bAlb) promoter, the murine albumin (mAlb) promoter, the human a1-antitrypsin (hAAT) promoter, the ApoEhAAT promoter composed of the ApoE enhancer and the hAAT promoter, the transthyretin (TTR) promoter, the liver fatty acid binding protein promoter, the hepatitis B virus (HBV) promoter, the DC172 promoter consisting of the hAAT promoter and the a1-microglobulin enhancer, the DC190 promoter containing the human albumin promoter and the prothrombin enhancer, and other natural and synthetic liver-specific promoters.

Muscle specific promoters include, but are not limited to, the MHCK7 promoter, the muscle creatine kinase (MCK) promoter/enhancer, the slow isoform of troponin I (TnIS) promoter, the MYODI promoter, the MYLK2 promoter, the SPc5-12 promoter, the desmin (Des) promoter, the unc45b promoter, and other natural and synthetic muscle-specific promoters.

Skeletal muscle-specific promoters include, but are not limited to, the HSA promoter, the human α-skeletal actin promoter.

Heart-specific promoters include, but art not limited to, the MYH6 promoter, the TNNI3 promoter, the cardiac troponin C (cTnC) promoter, the alpha-myosin heavy chain (α-MHC) promoter, myosin light chain 2 (MLC-2), and the MYBPC3 promoter.

Constitutive promoters refer to promoters that allow for continual transcription of its associated gene. Constitutive promoters are always active and can be used to express genes in a wide range of cells and tissues, including, but not limited to, the liver, kidney, skeletal muscle, cardiac muscle, smooth muscle, diaphragm muscle, brain, spinal cord, endothelial cells, intestinal cells, pulmonary cells (e.g., smooth muscle or epithelium), peritoneal epithelial cells and fibroblasts.

Constitutive promoters include, but are not limited to, a CMV major immediate-early enhancer/chicken beta-actin promoter, a cytomegalovirus (CMV) major immediate-early promoter, an Elongation Factor 1-α (EF1-α) promoter, a simian vacuolating virus 40 (SV40) promoter, an AmpR promoter, a PγK promoter, a human ubiquitin C gene (Ubc) promoter, a MFG promoter, a human beta actin promoter, a CAG promoter, a EGR1 promoter, a FerH promoter, a FerL promoter, a GRP78 promoter, a GRP94 promoter, a HSP70 promoter, a β-kin promoter, a murine phosphoglycerate kinase (mPGK) or human PGK (hPGK) promoter, a ROSA promoter, human Ubiquitin B promoter, a Rous sarcoma virus promoter, or any other natural or synthetic ubiquitous promoters. In some embodiments, the constitutively active promoter is selected from the group consisting of human β-actin, human elongation factor-1α, chicken β-actin combined with cytomegalovirus early enhancer, cytomegalovirus (CMV), simian virus 40, or herpes simplex virus thymidine kinase.

Inducible promoters refer to promoters that can be regulated by positive or negative control. Factors that can regulate an inducible promoter include, but are not limited to, chemical agents (e.g., the metallothionein promoter or a hormone inducible promoter), temperature, and light.

The tissue-specific promoters can be operably linked to one or more (e.g., 2, 3, 4, 5, 6, 7, or 8) enhancer elements (e.g., a neuron-specific promoter fused to a cytomegalovirus enhancer) or combined to form a tandem promoter (e.g., neuron-specific/constitutive tandem promoter). When two or more tissue-specific promoters are present, the isolated nucleic acid can be targeted to two or more different tissues at the same time.

An enhancer element is a nucleic acid sequence that functions to enhance transcription.

In some embodiments, the expression cassette comprises the ATP1A3 transgene sequence operably linked to a promoter and a polyadenylation sequence.

In other aspects, the nucleic acid expression cassette according to the present disclosure further comprises a transcriptional termination signal. A transcriptional termination signal is a nucleic acid sequence that marks the end of a gene during transcription. Examples of a transcriptional termination signal include, but are not limited to, bovine growth hormone polyadenylation signal (BGHpA), Simian virus 40 polyadenylation signal (Sv40 PolyA), and a synthetic polyadenylation signal. A polyadenylation sequence can comprise the nucleic acid sequence AATAAA. In some embodiments, a Sv40 PolyA has the sequence set forth in SEQ ID NO:17, or a sequence having at least 50%, 60%, 70%, 80%, 85%, 86%, 87%, 88%, 89%, 90%, 91%, 92%, 93%, 94%, 95%, 96%, 97%, 98%, or 99% sequence identity to the sequence set forth in SEQ ID NO:17.

As used herein, the term "intron" refers to nucleic acid sequences that can enhance transgene expression. An intron can also be a part of the nucleic acid expression cassette or positioned downstream or upstream of the expression cassette in the expression vector. Introns can include, but are not limited to, the SV40 intron, EF-1alpha gene intron 1, or the MVM intron. In some embodiments, the nucleic acid expression cassettes do not contain an intron.

As used herein, the terms "enhance" and "enhancement" with respect to nucleic acid expression or polypeptide production, refers to an increase and/or prolongation of steady-state levels of the indicated nucleic acid or polypeptide, e.g., by at least about 2%, 5%, 10%, 15%, 20%, 25%, 40%, 50%, 60%, 75%, 2-fold, 2.5-fold, 3-fold, 5-fold, 10-fold, 15-fold, 20-fold, 30-fold, 50-fold, 100-fold or more.

In some embodiments, the nucleic acid sequence encoding ATP1A3 is used as a "donor" template for homologous recombination with a mutant ATP1A3 gene in diseased cells. Further embodiments according to the present disclosure include the co-administration of the nucleic acid sequence with gene editing nucleases selected from the group consisting of zinc finger nucleases, TALENS, RNA-guided nucleases such as CRISPR/Cas98, and other programmable endonucleases.

Vectors

Another aspect of the present disclosure provides a vector comprising, consisting of, or consisting essentially of a nucleic acid sequence encoding ATP1A3. In some embodiments, the vector comprises, consists, or consists essentially of a nucleic acid expression cassette comprising a nucleic acid sequence encoding ATP1A3.

It will be apparent to those skilled in the art that any suitable vector can be used to deliver the isolated nucleic acids of the disclosure to the target cell(s) or subject of interest. The choice of delivery vector can be made based on a number of factors known in the art, including age and species of the target host, in vitro vs. in vivo delivery, level and persistence of expression desired, intended purpose (e.g., for therapy or enzyme production), the target cell or organ, route of delivery, size of the isolated nucleic acid, safety concerns, and the like.

Suitable vectors that are known in the art and that can be used to deliver, and optionally, express the isolated nucleic acids of the disclosure (e.g., viral and non-viral vectors), including, virus vectors (e.g., retrovirus, adenovirus, AAV, lentiviruses, or herpes simplex virus), lipid vectors, polylysine vectors, synthetic polyamino polymer vectors that are used with nucleic acid molecules, such as a plasmid, and the like. In some embodiments, the non-viral vector can be a polymer based vector (e.g., polyethyleimine (PEI), chitosan, poly (DL-Lactide) (PLA), or poly (DL-lactidie-co-glycoside) (PLGA), dendrimers, polymethacrylate) a peptide based vector, a lipid nanoparticle, a solid lipid nanoparticle, or a cationic lipid based vector.

Protocols for producing recombinant viral vectors and for using viral vectors for nucleic acid delivery can be found in *Current Protocols in Molecular Biology*; Ausubel, F. M. et al. (eds.) Greene Publishing Associates; (1989) and other standard laboratory manuals (e.g., Vectors for Gene Therapy, In: *Current Protocols in Human Genetics*, John Wiley and Sons, Inc.; 1997).

"Recombinant" is used herein to refer to new combinations of genetic material as a result of genetic engineering. For instance, a recombinant organism (e.g., bacteria) can be an organism that contains different genetic material from either of its parents as a result of genetic modification, recombinant DNA can be a form of artificial DNA, a recombinant protein or enzyme can be an artificially produced and purified form of the protein or enzyme, and a recombinant virus can be a virus formed by recombining genetic material.

In some embodiments, the nucleic acid expression cassettes and/or transgenes (e.g., ATP1A3 and variants thereof) can be incorporated into a recombinant viral vector.

As used herein, the term "viral vector" refers to a virus (e.g., AAV) particle that functions as a nucleic acid delivery vehicle, and which comprises the vector genome (e.g., viral DNA) packaged within a virion. Alternatively, in some contexts, the term "vector" is used to refer to the vector genome/viral DNA alone.

Any suitable recombinant viral vector suitable for gene therapy is suitable for use in the compositions and methods according to the present disclosure. Examples of such viral vectors include, but are not limited to vectors derived from: Adenoviridae; Birnaviridae; Bunyaviridae; Caliciviridae, Capillovirus group; Carlavirus group; Carmovirus virus group; Group Caulimovirus; Closterovirus Group; Commelina yellow mottle virus group; Comovirus virus group; Coronaviridae; PM2 phage group; Corcicoviridae; Group Cryptic virus; group Cryptovirus; Cucumovirus virus group family ([PHgr]6 phage group; Cysioviridae; Group Carnation ringspot; Dianthovirus virus group; Group Broad bean wilt; Fabavirus virus group; Filoviridae; Flaviviridae; Furovirus group; Group Germinivirus; Group Giardiavirus; Hepadnaviridae; Herpesviridae; Hordeivirus virus group; Illarvirus virus group; Inoviridae; Iridoviridae; Leviviridae; Lipothrixviridae; Luteovirus group; Marafivirus virus group; Maize chlorotic dwarf virus group; icroviridae; Myoviridae; Necrovirus group; Nepovirus virus group; Nodaviridae; Orthomyxoviridae; Papovaviridae; Paramyxoviridae; Parsnip yellow fleck virus group; Partitiviridae; Parvoviridae; Pea enation mosaic virus group; Phycodnaviridae; Picornaviridae; Plasmaviridae; Prodoviridae; Polydnaviridae; Potexvirus group; Potyvirus; Poxyiridae; Reoviridae; Retroviridae; Rhabdoviridae; Group Rhizidiovirus; Siphoviridae; Sobemovirus group; SSV 1-Type Phages; Tectiviridae; Tenuivirus; Tetraviridae; Group Tobamovirus; Group Tobravirus; Togaviridae; Group Tombusvirus; Group Torovirus; Totiviridae; Group Tymovirus; and plant virus satellites.

In some embodiments, the recombinant viral vector is selected from the group consisting of adenoviruses, Adeno-associated viruses (AAV) (e.g., AAV serotypes and genetically modified AAV variants), a herpes simplex viruses (e.g., e.g., HSV-1, HSV), a retrovirus vector (e.g., MMSV, MSCV), a lentivirus vector (HIV-1, HIV-2), and alphavirus vector (e.g., SFV, SIN, VEE, M1), a flavivirus vector (e.g., Kunjin, West Nile, Dengue virus), a rhabdovirus vector (e.g., Rabies, VSV), a measles virus vector (e.g., MV-Edm), a Newcastle disease virus vector, a poxvirus vector (VV), or a picornavirus vector (e.g., Coxsackievirus). The recombinant viral vector of the present disclosure includes any type of viral vector that is capable of packaging and delivering the ATP1A3 transgene or viral vectors that can be designed engineered and generated by methods known in the art.

In some embodiments, the delivery vector is an adenovirus vector. The term "adenovirus" as used herein encompasses all adenoviruses, including the Mastadenovirus and Aviadenovirus genera.

The various regions of the adenovirus genome have been mapped and are understood by those skilled in the art. The genomic sequences of the various Ad serotypes, as well as the nucleotide sequence of the particular coding regions of the Ad genome, are known in the art and may be accessed from GenBank and NCBI (see, e.g., GenBank Accession Nos. J0917, M73260, X73487, AF108105, L19443, NC 003266 and NCBI Accession Nos. NC 001405, NC 001460, NC 002067, NC 00454).

A recombinant adenovirus (rAd) vector genome can comprise the adenovirus terminal repeat sequences and packaging signal. An "adenovirus particle" or "recombinant adenovirus particle" comprises an adenovirus vector genome or recombinant adenovirus vector genome, respectively, packaged within an adenovirus capsid. Generally, the adenovirus vector genome is most stable at sizes of about 28 kb to 38 kb (approximately 75% to 105% of the native genome size). In the case of an adenovirus vector containing large deletions and a relatively small transgene, "stutter DNA" can be used to maintain the total size of the vector within the desired range by methods known in the art.

The genome of an adenovirus can be manipulated such that it encodes and expresses a gene product of interest but is inactivated in terms of its ability to replicate in a normal lytic viral life cycle. Suitable adenoviral vectors derived from the adenovirus strain Ad type 5 (Ad5) or other strains of adenovirus (e.g., Ad2, Ad3, Ad7, etc.) are known to those skilled in the art.

In some embodiments, the viral vector comprises a recombinant Adeno-Associated Viruses (AAV). AAV are parvoviruses and have small icosahedral virions and can contain a single stranded DNA molecule about 4.7 kb (e.g., about 4.5 kb, 4.6 kb, 4.8 kb, 4.9 kb, or 5.0 kb) or less in size. The viruses contain either the sense or antisense strand of the DNA molecule and either strand is incorporated into the virion. Two open reading frames encode a series of Rep and Cap polypeptides. Rep polypeptides (e.g., Rep50, Rep52, Rep68 and Rep78) are involved in replication, rescue and integration of the AAV genome, although significant activity may be observed in the absence of all four Rep polypeptides. The Cap proteins (e.g., VP1, VP2, VP3) form the virion capsid. Flanking the rep and cap open reading frames at the 5' and 3' ends of the genome are inverted terminal repeats (ITRs). Typically, in recombinant AAV (rAAV) vectors, the entire rep and cap coding regions are excised and replaced with a transgene of interest.

Recombinant AAV vectors generally require only the terminal repeat(s) (TR(s)) in cis to generate virus. All other viral sequences are dispensable and may be supplied in trans. Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments of the present disclosure, the rAAV vector genome comprises at least one terminal repeat (TR) sequence (e.g., AAV TR sequence), optionally two TRs (e.g., two AAV TRs), which typically will be at the 5' and 3' ends of the vector genome and flank the heterologous nucleic acid sequence, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic, such as the "double-D sequence."

An "AAV terminal repeat" or "AAV TR" may be from any AAV, including but not limited to serotypes 1, 2, 3, 4, 5, 6, 7, 8, 9, 10 or 11 or any other AAV now known or later discovered. An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like. In some embodiments, the vector comprises flanking ITRs derived from the AAV2 genome. The ITRs of the present disclosure can have a sequence set forth in SEQ ID NO:10 or SEQ ID NO:18, or a sequence having at least 50%, 60%, 70%, 80%, 85%, 86%, 87%, 88%, 89%, 90%, 91%, 92%, 93%, 94%, 95%, 96%, 97%, 98%, or 99% sequence identity to the sequence set forth in SEQ ID NO:10 or SEQ ID NO:18.

Wild-type AAV can integrate their DNA into non-dividing cells, and exhibit a high frequency of stable integration into human chromosome 19. A rAAV vector genome will typically comprise the AAV terminal repeat sequences and packaging signal.

An "AAV particle" or "rAAV particle" comprises an AAV vector genome or rAAV vector genome, respectively, packaged within an AAV capsid. The AAV rep/cap genes can be expressed on a single plasmid. The AAV rep and/or cap sequences may be provided by any viral or non-viral vector. For example, the rep/cap sequences may be provided by a hybrid adenovirus or herpesvirus vector (e.g., inserted into the E1a or E3 regions of a deleted adenovirus vector). EBV vectors may also be employed to express the AAV cap and rep genes. One advantage of this method is that EBV vectors are episomal, yet will maintain a high copy number throughout successive cell divisions (i.e., are stably integrated into the cell as extrachromosomal elements, designated as an "EBV based nuclear episome," see Margolski (1992) *Curr. Top. Microbiol. Immun.* 158:67). The AAV rep and cap genes may be from any AAV serotype for which recombinant virus can be derived and may be from a different AAV serotype than the rAAV genome ITRs.

However, the rAAV vector itself need not contain AAV genes encoding the capsid (cap) and Rep proteins. In particular embodiments of the disclosure, the rep and/or cap genes are deleted from the AAV genome. In a representative embodiment, the rAAV vector retains only the terminal AAV sequences (ITRs) necessary for integration, excision, and replication.

Sources for the AAV capsid genes can include naturally isolated serotypes, including but not limited to, AAV1, AAV2, AAV3 (including 3a and 3b), AAV4, AAV5, AAV6, AAV7, AAV8, AAVrh8, AAV9, AAV10, AAVrh10, AAV11, AAV12, AAV13, AAVrh39, AAVrh43, AAVcy.7, as well as bovine AAV, caprine AAV, canine AAV, equine AAV, ovine AAV, avian AAV, primate AAV, non-primate AAV, and any other virus classified by the International Committee on Taxonomy of Viruses (ICTV) as an AAV. In particular embodiments, the AAV capsids are chimeras either created by capsid evolution or by rational capsid engineering from the naturally isolated AAV variants to capture desirable serotype features such as enhanced or specific tissue tropism and host immune response escape, including but not limited to AAV-DJ, AAV-HAE1, AAV-HAE2, AAVM41, AAV-1829, AAV2 Y/F, AAV2 T/V, AAV2i8, AAV2.5, AAV9.45, AAV9.61, AAV-B1, AAV-AS, AAV9.45A-String (e.g., AAV9.45-AS), AAV9.45Angiopep, AAV9.47-Angiopep, and AAV9.47-AS., AAV-PHP.B, AAV-PHP.eB, and AAV-PHP.S.

Accordingly, when referring herein to a specific AAV capsid protein (e.g., an AAV2, AAV3, AAV4, AAV5, AAV6, AAV7, AAV8, AAV9, AAV10, AAV1 or AAV12 capsid protein) it is intended to encompass the native capsid protein as well as capsid proteins that have alterations other than the modifications of the invention. Such alterations include substitutions, insertions and/or deletions.

In some embodiments, the recombinant AAV vector is selected from the group consisting of AAV1, AAV8, or AAV9. In certain embodiments, the recombinant AAV vector comprises AAV9 due to its ability to easily cross the blood-brain barrier.

In some embodiments, the recombinant viral vectors (e.g., rAAV) according to the present disclosure generally comprise, consist of, or consist essentially of one or more of the following elements: (1) an Inverted Terminal Repeat sequence (ITR); (2) a promoter (e.g., a neuron-specific promoter); (3) a transgene (e.g., a nucleic acid sequence encoding ATP1A3, a fragment thereof, an isoform thereof, or a homologue thereof); (4) a transcription terminator (e.g., a polyadenylation signal); and (5) a flanking Inverted Terminal Repeat sequence (ITR).

In some embodiments, the recombinant viral vector can comprise a linker sequence. The term "linker sequence" as used herein refers to a nucleic acid sequence that encodes a short polypeptide sequence. A linker sequence can comprise at least 6 nucleotide sequences, at least 15 nucleotides, 27 nucleotides, or at least 30 nucleotides. In some embodiments, the linker sequence has 6 to 27 nucleotides. In other embodiments, the linker sequence has 6 nucleotides, 15 nucleotides, and/or 27 nucleotides. A linker sequence can be used to connect various encoded elements in the vector constructs. For example, a transgene and Myc tag can be operably linked via a linker, or a Myc tag and FLAG can be operably linked via a linker or a FLAG tag and mCherry tag can be operably linked via a linker. Alternatively, the vector elements can be directly linked (e.g., not via a linker). Exemplary linker sequences are shown in Table 2:

TABLE 2

Representative Linker Sequences

| | |
|---|---|
| Linker Sequence (27 nucleotides) | ACCTACTACACGCGTACGCGGCCGCTC (SEQ ID NO: 11) |
| Linker Sequence (15 nucleotides) | GCAGCAAATGATATCCTG (SEQ ID NO: 13) |
| Linker Sequence (6 nucleotides) | GGATTC (SEQ ID NO: 15) |

In some embodiments, the vectors according to the present disclosure can comprise fluorescent protein tags (e.g., mCherry, sfGFP, and mKikGR) and/or epitope tags (e.g., HA, Myc, FLAG).

In some embodiments, a mCherry tag can be encoded by the nucleic acid sequence set forth in SEQ ID NO:16, or a sequence having at least 50%, 60%, 70%, 80%, 85%, 86%, 87%, 88%, 89%, 90%, 91%, 92%, 93%, 94%, 95%, 96%, 97%, 98%, or 99% sequence identity to the sequence set forth in SEQ ID NO:16.

In some embodiments, a Myc tag can be encoded by the nucleic acid sequence set forth in SEQ ID NO:12, or a sequence having at least 50%, 60%, 70%, 80%, 85%, 86%, 87%, 88%, 89%, 90%, 91%, 92%, 93%, 94%, 95%, 96%, 97%, 98%, or 99% sequence identity to the sequence set forth in SEQ ID NO:12.

In some embodiments, a FLAG tag can be encoded by the nucleic acid sequence set forth in SEQ ID NO:14, or a sequence having at least 50%, 60%, 70%, 80%, 85%, 86%, 87%, 88%, 89%, 90%, 91%, 92%, 93%, 94%, 95%, 96%, 97%, 98%, or 99% sequence identity to the sequence set forth in SEQ ID NO:14.

In other embodiments, the vectors can optionally comprise a 2A self-cleaving peptide (2A peptide), which is a class of peptides that can be about 18-22 amino acids in length and can induce the cleaving of a recombinant protein in a cell. Examples of 2A peptides include, but are not limited to, P2A, E2A, F2A and T2A. In some embodiments, the 2A peptide can be P2A. In some embodiments, P2A can be encoded by the nucleic acid sequence set forth in SEQ ID NO:22, or a sequence having at least 50%, 60%, 70%, 80%, 85%, 86%, 87%, 88%, 89%, 90%, 91%, 92%, 93%, 94%, 95%, 96%, 97%, 98%, or 99% sequence identity to the sequence set forth in SEQ ID NO:22.

In some embodiments, a 2A peptide can be combined with an internal ribosome entry site (IRES) element, which can make it possible to generate four separated peptides within a single transcript. The location for IRES elements can be at the 5'UTR, but can also occur elsewhere in the nucleic acid sequence.

In some embodiments, the vectors of the present disclosure optionally comprise an intron. In other embodiments, the vectors of the present disclosure do not contain an intron.

In one embodiment, the recombinant AAV vector comprises a nucleotide sequence encoding ATP1A3.

In some embodiments, the active vector comprises a construct as shown in FIG. 1.

Figure 2:
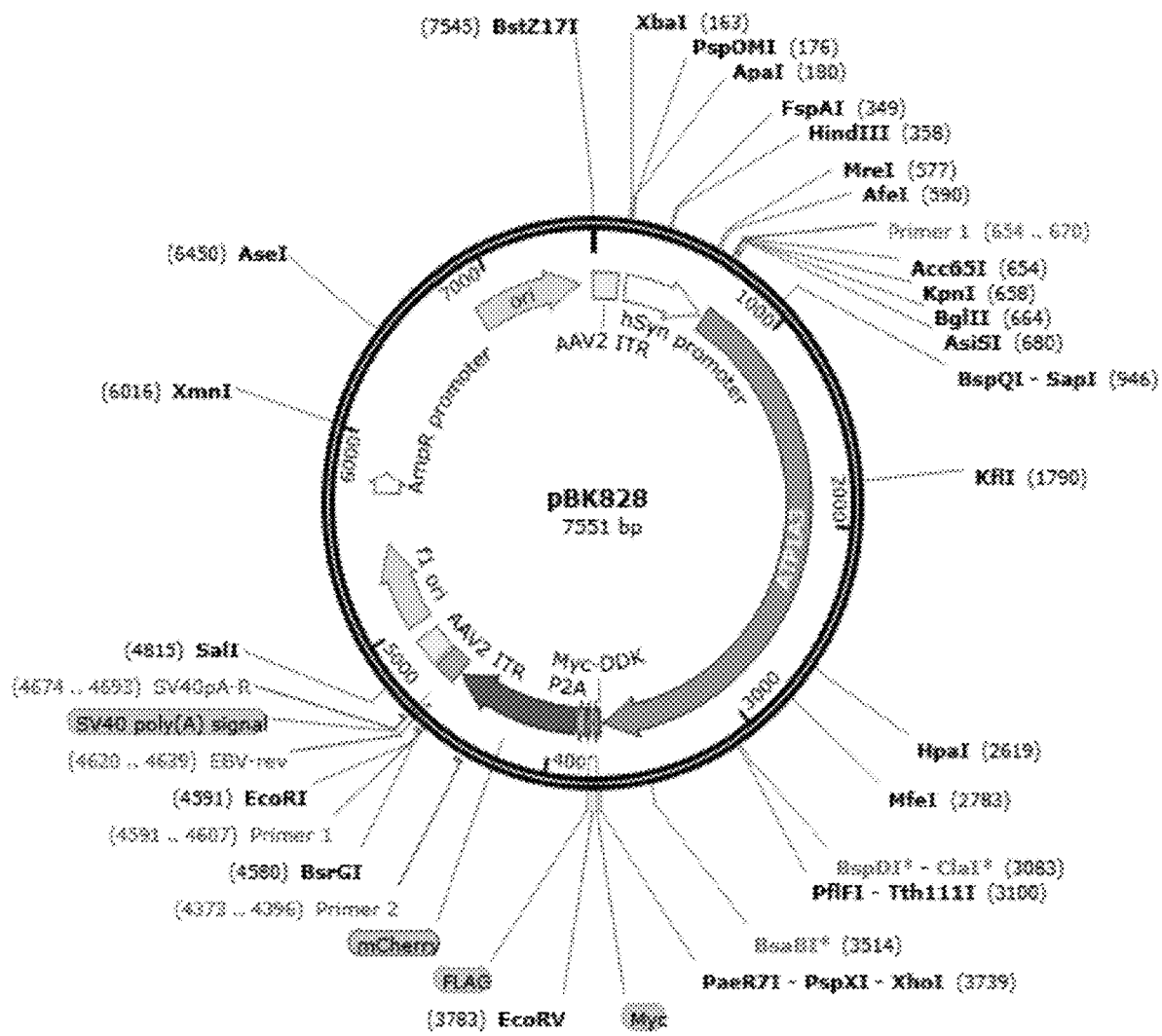
FIG. 2 is a construct map of the AAV vector comprising pBK828 (AAV9-hSyn-ATP1A3-FLAG-p2a-Cherry-SV40polyA, active vector).

In some embodiments, the active vector comprises AAV9-pBK828-ATP1A3-cherry (also referred to herein as AAV9-hSyn-ATP1A3-FLAG-p2a-Cherry-SV40polyA or AAV9-ATP1A3-Cherry or active vector) (FIG. 2). An AAV9-hSyn-ATP1A3-FLAG-p2a-Cherry-SV40polyA vector of the present disclosure can comprise an ITR, a human Syn promoter, an ATP1A3 open reading frame (ORF), one or more epitope tags (e.g., a Myc tag, or a FLAG tag), a P2A sequence, one or more fluorescence tags (e.g., an mCherry tag), a Sv40 PolyA tail, and a flanking ITR (FIG. 1). The AAV9-hSyn-ATP1A3-FLAG-p2a-Cherry-SV40polyA vector can also comprise one or more linker sequences in between the elements.

In some embodiments, the AAV9-hSyn-ATP1A3-FLAG-p2a-Cherry-SV40polyA vector can comprise the following elements operably linked in order of 5' to 3': an AAV-ITR, a human Syn promoter, an ATP1A3 transgene, a linker sequence, a Myc tag, a linker sequence, a FLAG tag, a linker sequence, a p2A sequence, a linker sequence, a mCherry tag, a Sv40 PolyA sequence, and an AAV-ITR.

The active vector can comprise the nucleic acid sequence set forth in SEQ ID NO:19, SEQ ID NO:20, or SEQ ID NO:21, or a sequence having at least 50%, 60%, 70%, 80%, 85%, 86%, 87%, 88%, 89%, 90%, 91%, 92%, 93%, 94%, 95%, 96%, 97%, 98%, or 99% sequence identity to the sequence set forth in SEQ ID NO:19, SEQ ID NO:20, or SEQ ID NO:21.

Figure 3:
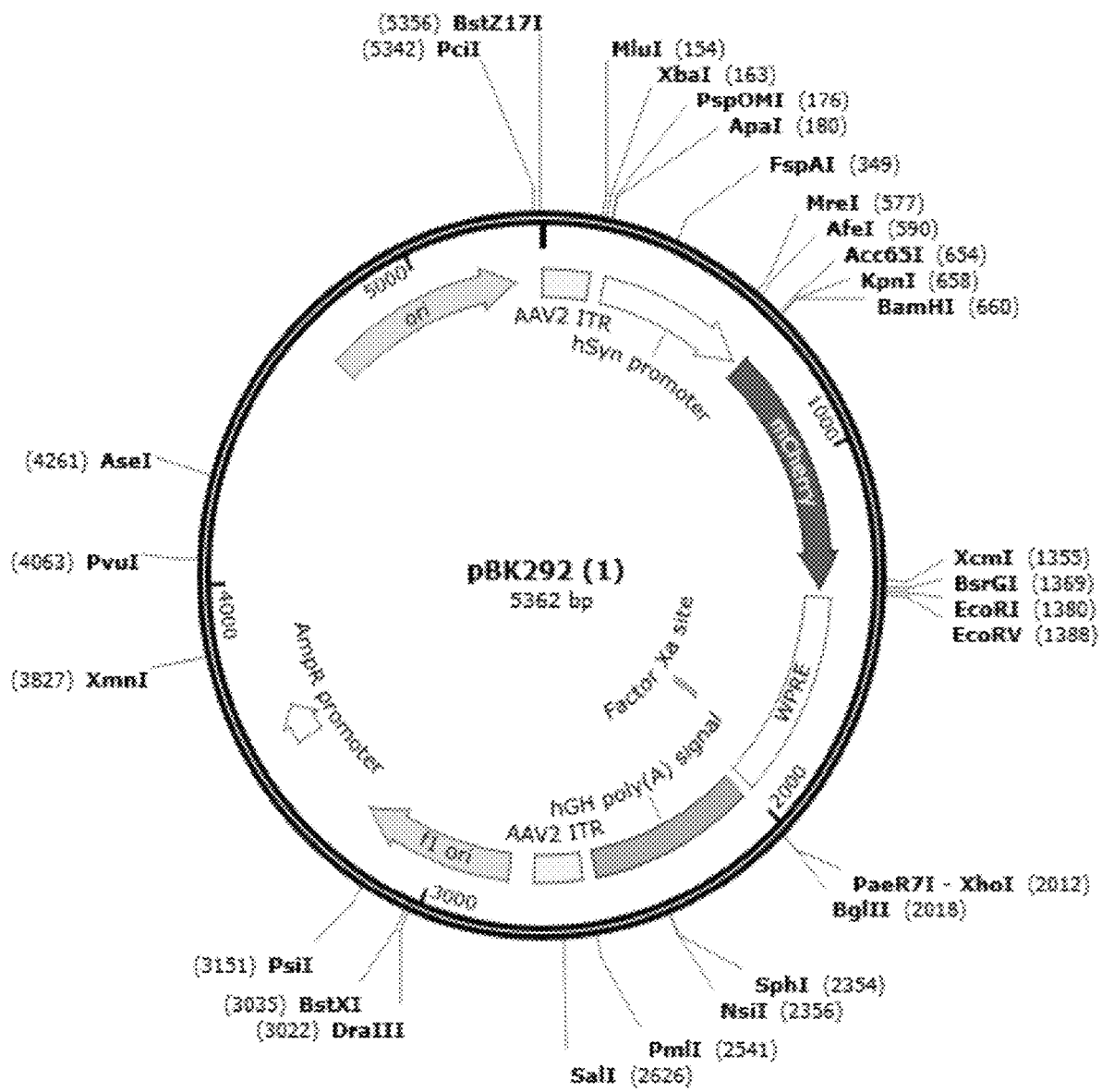
FIG. 3 is a construct map of the AAV vector comprising pBK292 (control vector).

In another embodiment, the recombinant AAV control vector can comprise AAV9-hSyn-mCherry-pBK292-9 (FIG. 3). This vector does not contain a transgene can be used as a control vector to the AAV9-pBK828-ATP1A3-cherry vector.

TABLE 3

Nucleic Acid Constructs

| | |
|---|---|
| Nucleic Acid construct containing the following elements in order of 5' to 3': AAV-ITR, hSyn promoter, ATP1A3, linker, Myc tag, linker, Flag tag, linker, mCherry, Sv40 PolyA, AAV-ITR | TCCTGCAGGCAGCTGCGCGCTCGCTCGCTCACTGAGGCCGCCCGGGCAAAGTCCCGGGC<br>GTCGGGCGACCTTTGGTCGCCCGGCCTCAGTGAGCGAGCGAGCTGCGCAGAGAGGGAGT<br>GGCCAACTCCATCACTAGGGGTTCCTAGTGCAAGTGGGTTTTTAGGACCAGGATGAGGC<br>GGGGTGGGGGTGCCTACCTGACGACCGACCCCGGACCCACTGGACAAGCACCCAACCCC<br>CATTCCCCAAATTGCGCATCCCCTAATCAGAGAGGGGGAGGGGAAACAGGATGCGGCGA<br>GGCGCGTGCGCACTGCCAAGCTTCAGCACCGCGGACAGTGCCTTCGCCCCCGCCTGGCG<br>GCGCGCGCCCACCGCCGCCTCAGCACTGAAGGCGCGCTGACGTCACTCGCCGGTCCCCC<br>GACAAACTCCCCTTCCCGGCCACCTTGGTCGCGTCCGCGCCGCCGCCGCCCAGCCGG<br>ACCGCACCACGCGAGGCGCGAGATAGGGGGGCACGGGCGCGACCCATCTGCGCTGCGGC<br>GCCGGCGACTCAGCGCTGCCTCAGTCTGCGGTGGGCAAGCGGAGGAGTCGTGTCGTGCC<br>TGAGAGCGCAGTCGAGAAGGTACCGAGGAGATCTGCCGCCATGGGGGACAAGAAAGATG<br>ACAAGGACTCACCCAAGAAGAACAAGGGCAAGGAGCGCCGGGACCTGGATGACCTCAAG<br>AAGGAGGTGGCTATGACAGAGCACAAGATGTCAGTGGAAGAGGTCTGCCGGAAATACAA<br>CACAGACTGTGTGCAGGGTTTGACCCACAGCAAAGCCCAGGAGATCCTGGCCCGGGATG<br>GGCCTAACGCACTCACGCCACCGCCTACCACCCCAGAGTGGGTCAAGTTTTGCCGGCAG<br>CTCTTCGGGGGCTTCTCCATCCTGCTGTGGATCGGGGCTATCCTCTGCTTCCTGGCCTA<br>CGGTATCCAGGCGGGCACCGAGGACGACCCCTCTGGTGACAACCTGTACCTGGGCATCG<br>TGCTGGCGGCCGTGGTGATCATCACTGGCTGCTTCTCCTACTACCAGGAGGCCAAGAGC<br>TCCAAGATCATGGAGTCCTTCAAGAACATGGTGCCCCAGCAAGCCCTGGTGATCCCGGA<br>AGGTGAGAAGATGCAGGTGAACGCTGAGGAGGTGGTGGTCGGGGACCTGGTGGAGATCA<br>AGGGTGGAGACCGAGTGCCAGCTGACCTGCGGATCATCTCAGCCCACGGCTGCAAGGTG |

TABLE 3-continued

Nucleic Acid Constructs

GACAACTCCTCCCTGACTGGCGAATCCGAGCCCCAGACTCGCTCTCCCGACTGCACGCA
CGACAACCCCTTGGAGACTCGGAACATCACCTTCTTTTCCACCAACTGTGTGGAAGGCA
CGGCTCGGGGCGTGGTGGTGGCCACGGGCGACCGCACTGTCATGGGCCGTATCGCCACC
CTGGCATCAGGGCTGGAGGTGGGCAAGACGCCCATCGCCATCGAGATTGAGCACTTCAT
CCAGCTCATCACCGGCGTGGCTGTCTTCCTGGGTGTCTCCTTCTTCATCCTCTCCCTCA
TTCTCGGATACACCTGGCTTGAGGCTGTCATCTTCCTCATCGGCATCATCGTGGCCAAT
GTCCCAGAGGGTCTGCTGGCCACTGTCACTGTGTGTCTGACGCTGACCGCCAAGCGCAT
GGCCCGGAAGAACTGCCTGGTGAAGAACCTGGAGGCTGTAGAAACCCTGGGCTCCACGT
CCACCATCTGCTCAGATAAGACAGGGACCCTCACTCAGAACCGCATGACAGTCGCCCAC
ATGTGGTTTGACAACCAGATCCACGAGGCTGACACCACTGAGGACCAGTCAGGGACCTC
ATTTGACAAGAGTTCGCACACCTGGGTGGCCCTGTCTCACATCGCTGGGCTCTGCAATC
GCGCTGTCTTCAAGGGTGGTCAGGACAACATCCCTGTGCTCAAGAGGGATGTGGCTGGG
GATGCGTCTGAGTCTGCCCTGCTCAAGTGCATCGAGCTGTCCTCTGGCTCCGTGAAGCT
GATGCGTGAACGCAACAAGAAAGTGGCTGAGATTCCCTTCAATTCCACCAACAAATACC
AGCTCTCCATCCATGAGACCGAGGACCCCAACGACAACCGATACCTGCTGGTGATGAAG
GGTGCCCCCGAGCGCATCCTGGACCGCTGCTCCACCATCCTGCTACAGGGCAAGGAGCA
GCCTCTGGACGAGGAAATGAAGGAGGCCTTCCAGAATGCCTACCTTGAGCTCGGTGGCC
TGGGCGAGCGCGTGCTTGGTTTCTGCCATTATTACCTGCCCGAGGAGCAGTTCCCCAAG
GGCTTTGCCTTCGACTGTGATGACGTGAACTTCACCACGGACAACCTCTGCTTTGTGGG
CCTCATGTCCATGATCGACCCACCCCGGGCAGCCGTCCCTGACGCGGTGGGCAAGTGTC
GCAGCGCAGGCATCAAGGTCATCATGGTCACCGGCGATCACCCCATCACGGCCAAGGCC
ATTGCCAAGGGTGTGGGCATCATCTCTGAGGGCAACGAGACTGTGGAGGACATCGCCGC
CCGGCTCAACATTCCCGTCAGCCAGGTTAACCCCCGGGATGCCAAGGCCTGCGTGATCC
ACGGCACCGACCTCAAGGACTTCACCTCCGAGCAAATCGACGAGATCCTGCAGAATCAC
ACCGAGATCGTCTTCGCCCGCACATCCCCCCAGCAGAAGCTCATCATTGTGGAGGGCTG
TCAGAGACAGGGTGCAATTGTGGCTGTGACCGGGGATGGTGTGAACGACTCCCCCGCTC
TGAAGAAGGCCGACATTGGGGTGGCCATGGGCATCGCTGGCTCTGACGTCTCCAAGCAG
GCAGCTGACATGATCCTGCTGGACGACAACTTTGCCTCCATCGTCACAGGGGTGGAGGA
GGGCCGCCTGATCTTCGACAACCTAAAGAAGTCCATTGCCTACACCCTGACCAGCAATA
TCCCGGAGATCACGCCCTTCCTGCTGTTCATCATGGCCAACATCCCGCTGCCCCTGGGC
ACCATCACCATCCTCTGCATCGATCTGGGCACTGACATGGTCCCTGCCATCTCACTGGC
GTACGAGGCTGCCGAAAGCGACATCATGAAGAGACAGCCCAGGAACCCGCGGACGGACA
AATTGGTCAATGAGAGACTCATCAGCATGGCCTACGGGCAGATTGGAATGATCCAGGCT
CTCGGTGGCTTCTTCTCTTACTTTGTGATCCTGGCAGAAAATGGCTTCTTGCCCGGCAA
CCTGGTGGGCATCCGGCTGAACTGGGATGACCGCACCGTCAATGACCTGGAAGACAGTT
ACGGGCAGCAGTGGACATACGAGCAGAGGAAGGTGGTGGAGTTCACCTGCCACACGGCC
TTCTTTGTGAGCATCGTTGTCGTCCAGTGGGCCGATCTGATCATCTGCAAGACCCGGAG
GAACTCGGTCTTCCAGCAGGGCATGAAGAACAAGATCCTGATCTTCGGGCTGTTTGAGG
AGACGGCCCTGGCTGCCTTCCTGTCCTACTGCCCCGGCATGGACGTGGCCCTGCGCATG
TACCCTCTCAAGCCCAGCTGGTGGTTCTGTGCCTTCCCCTACGTTTCCTCATCTTCGT
CTACGACGAAATCCGCAAACTCATCCTGCGCAGGAACCCAGGGGGTTGGGTGGAGAAGG
AAAACCTACTACACGCGTACGCGGCCGCTCGAGCAGAAACTCATCTCAGAAGAGGATCT
GGCAGCAAATGATATCCTGGATTACAAGGATGACGACGATAAAGGATTCGTGAGCAAGG
GCGAGGAGGATAACATGGCCATCATCAAGGAGTTCATGCGCTTCAAGGTGCACATGGAG
GGCTCCGTGAACGGCCACGAGTTCGAGATCGAGGGCGAGGGCGAGGGCCGCCCCTACGA
GGGCACCCAGACCGCCAAGCTGAAGGTGACCAAGGGTGGCCCCCTGCCCTTCGCCTGGG
ACATCCTGTCCCCTCAGTTCATGTACGGCTCCAAGGCCTACGTGAAGCACCCCGCCGAC
ATCCCCGACTACTTGAAGCTGTCCTTCCCCGAGGGCTTCAAGTGGGAGCGCGTGATGAA
CTTCGAGGACGGCGGCGTGGTGACCGTGACCCAGGACTCCTCCCTGCAGGACGGCGAGT
TCATCTACAAGGTGAAGCTGCGCGGCACCAACTTCCCCTCCGACGGCCCCGTAATGCAG
AAGAAGACCATGGGCTGGGAGGCCTCCTCCGAGCGGATGTACCCCGAGGACGGCGCCCT
GAAGGGCGAGATCAAGCAGAGGCTGAAGCTGAAGGACGGCGGCCACTACGACGCTGAGG
TCAAGACCACCTACAAGGCCAAGAAGCCCGTGCAGCTGCCCGGCGCCTACAACGTCAAC
ATCAAGTTGGACATCACCTCCCACAACGAGGACTACACCATCGTGGAACAGTACGAACG
CGCCGAGGGCCGCCACTCCACCGGCGGCATGGACGAGCTGTACAAGTAATAAGATACAT
TGATGAGTTTGGACAAACCACAACTAGAATGCAGTGAAAAAAATGCTTTATTTGTGAAA
TTTGTGATGCTATTGCTTTATTTGTAACCATTATAAGCTGCAATAAACAAGTTAGGAAC
CCTAGTGATTGGAGTTGGCCACTCCCTCTCTGCGCGCTCGCTCGCTCACTGAGGCCGG
GTCGACCAAAGGTCGCCCGACGCCCGGGCTTTGCCCGGGCGGCCTCAGTGAGTCGAGCG
AGCGCGCAGCTGCCTGCAGG (SEQ ID NO: 19)

| | |
|---|---|
| Nucleic Acid construct containing the following elements in order of 5' to 3': AAV-ITR, hSyn promoter, ATP1A3, linker, Myc tag, linker, Flag tag, linker, p2a, linker, mCherry, Sv40 PolyA, AAV-ITR | TCCTGCAGGCAGCTGCGCGCTCGCTCGCTCACTGAGGCCGCCCGGGCAAAGTCCCGGGC<br>GTCGGGCGACCTTTGGTCGCCCGGCCTCAGTGAGCGAGCGAGCGCGCAGAGAGGGAGT<br>GGCCAACTCCATCACTAGGGGTTCCTAGTGCAAGTGGGTTTTTAGGACCAGGATGAGGC<br>GGGGTGGGGGTGCCTACCTGACGACCGACCCCGGACCCACTGGACAAGCACCCAACCCC<br>CATTCCCCAAATTGCGCATCCCCTAATCAGAGAGGGGGAGGGGAAACAGGATGCGGCGA<br>GGCGCGTGCGCACTGCCAAGCTTCAGCACCGCGGACAGTGCCTTCGCCCCCGCCTGGCG<br>GCGCGCGCCCACCGCCGCCTCAGCACTGAAGGCGCGCTGACGTCACTCGCCGGTCCCCC<br>GACAAACTCCCCTTCCCGGCCACCTTGGTCGCGTCCGCGCCGCCGCCGGCCCCAGCCGG<br>ACCGCACCACGCGAGGCGCGAGATAGGGGGCACGGGCGCGACCCATCTGCGCTGCGGC<br>GCCGGCGACTCAGCGCTGCCTCAGTCTGCGGTGGGCAAGCGGAGGAGTCGTGTCGTGCC<br>TGAGAGCGCAGTCGAGAAGGTACCGAGGAGATCTGCCGCCATGGGGACAAGAAAGATG<br>ACAAGGACTCACCCAAGAAGAACAAGGGCAAGGAGCGCCGGGACCTGGATGACCTCAAG<br>AAGGAGGTGGCTATGACAGAGCACAAGATGTCAGTGGAGAGGTCTGCCGGAAATACAA<br>CACAGACTGTGTGCAGGGTTTGACCCACAGCAAAGCCCAGGAGATCCTGGCCCGGGATG<br>GGCCTAACGCACTCACGCCACCGCCTACCACCCCAGAGTGGGTCAAGTTTTGCCGGCAG<br>CTCTTCGGGGCTTCTCCATCCTGCTGTGGATCGGGCTATCCTCTGCTTCCTGGCCTA<br>CGGTATCCAGGCGGGCACCGAGGACGACCCCTCTGGTGACAACCTGTACCTGGGCATCG |

TABLE 3-continued

Nucleic Acid Constructs

| | |
|---|---|
| | TGCTGGCGGCCGTGGTGATCATCACTGGCTGCTTCTCCTACTACCAGGAGGCCAAGAGC<br>TCCAAGATCATGGAGTCCTTCAAGAACATGGTGCCCCAGCAAGCCCTGGTGATCGGGA<br>AGGTGAGAAGATGCAGGTGAACGCTGAGGAGGTGGTGGTCGGGGACCTGGTGGAGATCA<br>AGGGTGGAGACCGAGTGCCAGCTGACCTGCGGATCATCTCAGCCCACGGCTGCAAGGTG<br>GACAACTCCTCCCTGACTGGCGAATCCGAGCCCCAGACTCGCTCTCCCGACTGCACGCA<br>CGACAACCCCTTGGAGACTCGGAACATCACCTTCTTTTCCACCAACTGTGTGGAAGGCA<br>CGGCTCGGGGCGTGGTGGTGGCCCACGGGCGACCGCACTGTCATGGGCCGTATCGCCACC<br>CTGGCATCAGGGCTGGAGGTGGGCAAGACGCCCATCGCCATCGAGATTGAGCACTTCAT<br>CCAGCTCATCACCGGCGTGGCTGTCTTCCTGGGTGTCTCCTTCTTCATCCTCTCCCTCA<br>TTCTCGGATACACCTGGCTTGAGGCTGTCATCTTCCTCATCGGCATCATCGTGGCCAAT<br>GTCCCAGAGGGTCTGCTGGCCACTGTCACTGTGTGTCTGACGCTGACCGCCAAGCGCAT<br>GGCCCGGAAGAACTGCCTGGTGAAGAACCTGGAGGCTGTAGAAACCCTGGGCTCCACGT<br>CCACCATCTGCTCAGATAAGACAGGGACCCTCACTCAGAACCGCATGACAGTCGCCCAC<br>ATGTGGTTTGACAACCAGATCCACGAGGCTGACACCACTGAGGACCAGTCAGGGACCTC<br>ATTTGACAAGAGTTCGCACACCTGGGTGGCCCTGTCTCACATCGCTGGGCTCTGCAATC<br>GCGCTGTCTTCAAGGGTGGTCAGGACAACATCCCTGTGCTCAAGAGGGATGTGGCTGGG<br>GATGCGTCTGAGTCTGCCCTGCTCAAGTGCATCGAGCTGTCCTCTGGCTCCGTGAAGCT<br>GATGCGTGAACGCAACAAGAAAGTGGCTGAGATTCCCTTCAATTCCACCAACAAATACC<br>AGCTCTCCATCCATGAGACCGAGGACCCCAACGACAACCGATACCTGCTGGTGATGAAG<br>GGTGCCCCCGAGCGCATCCTGGACCGCTGCTCCACCATCCTGCTACAGGGCAAGGAGCA<br>GCCTCTGGACGAGGAAATGAAGGAGGCCTTCCAGAATGCCTACCTTGAGCTCGGTGGCC<br>TGGGCGAGCGCGTGCTTGGTTTCTGCCATTATTACCTGCCCGAGGAGCAGTTCCCCAAG<br>GGCTTTGCCTTCGACTGTGATGACGTGAACTTCACCACGGACAACCTCTGCTTTGTGGG<br>CCTCATGTCCATGATCGACCCACCCCGGGCAGCCGTCCCTGACGCGGTGGGCAAGTGTC<br>GCAGCGCAGGCATCAAGGTCATCATGGTCACCGGCGATCACCCCATCACGGCCAAGGCC<br>ATTGCCAAGGGTGTGGGCATCATCTCTGAGGGCAACGAGACTGTGGAGGACATCGCCGC<br>CCGGCTCAACATTCCCGTCAGCCAGGTTAACCCCGGGATGCCAAGGCCTGCGTGATCC<br>ACGGCACCGACCTCAAGGACTTCACCTCCGAGCAAATCGACGAGATCCTGCAGAATCAC<br>ACCGAGATCGTCTTCGCCCGCACATCCCCCCAGCAGAAGCTCATCATTGTGGAGGGCTG<br>TCAGAGACAGGGTGCAATTGTGGCTGTGACCGGGGATGGTGTGAACGACTCCCCCGCTC<br>TGAAGAAGGCCGACATTGGGGTGGCCATGGGCATCGCTGGCTCTGACGTCTCCAAGCAG<br>GCAGCTGACATGATCCTGCTGGACGACAACTTTGCCTCCATCGTCACAGGGGTGGAGGA<br>GGGGCCGCTGATCTTCGACAACCTAAAGAAGTCCATTGCCTACACCCTGACCAGCAATA<br>TCCCGGAGATCACGCCCTTCCTGCTGTTCATCATGGCCAACATCCCGCTGCCCCTGGGC<br>ACCATCACCATCCTCTGCATCGATCTGGGCACTGACATGGTCCCTGCCATCTCACTGGC<br>GTACGAGGCTGCCGAAAGCGACATCATGAAGAGACAGCCCAGGAACCCGCGGACGGACA<br>AATTGGTCAATGAGAGACTCATCAGCATGGCCTACGGGCAGATTGGAATGATCCAGGCT<br>CTCGGTGGCTTCTTCTCTTACTTTGTGATCCTGGCAGAAAATGGCTTCTTGCCCGGCAA<br>CCTGGTGGGCATCCGGCTGAACTGGGATGACCGCACCGTCAATGACCTGGAAGACAGTT<br>ACGGGCAGCAGTGGACATACGAGCAGAGGAAGGTGGTGGAGTTCACCTGCCACACGGCC<br>TTCTTTGTGAGCATCGTTGTCGTCCAGTGGGCCGATCTGATCATCTGCAAGACCCGGAG<br>GAACTCGGTCTTCCAGCAGGGCATGAAGAACAAGATCCTGATCTTCGGGCTGTTTGAGG<br>AGACGGCCCTGGCTGCCTTCCTGTCCTACTGCCCCGGCATGGACGTGGCCCTGCGCATG<br>TACCCTCTCAAGCCCAGCTGGTGGTTCTGTGCCTTCCCCTACAGTTTCCTCATCTTCGT<br>CTACGACGAAATCCGCAAACTCATCCTGCGCAGGAACCCAGGGGGTTGGGTGGAGAAGG<br>AAAACCTACTACACGCGTACGCGGCCGCTCGAGCAGAAACTCATCTCAGAAGAGGATCT<br>GGCAGCAAATGATATCCTGGATTACAAGGATGACGACGATAAAGGATTCGCCACGAACT<br>TCTCTCTGTTAAAGCAAGCAGGAGACGTGGAAGAAAACCCCGGTCCCGGATTCGTGAGC<br>AAGGGCGAGGAGGATAACATGGCCATCATCAAGGAGTTCATGCGCTTCAAGGTGCACAT<br>GGAGGGCTCCGTGAACGGCCACGAGTTCGAGATCGAGGGCGAGGGCGAGGGCCGCCCCT<br>ACGAGGGCACCCAGACCGCCAAGCTGAAGGTGACCAAGGGTGGCCCCCTGCCCTTCGCC<br>TGGGACATCCTGTCCCCTCAGTTCATGTACGGCTCCAAGGCCTACGTGAAGCACCCCGC<br>CGACATCCCCGACTACTTGAAGCTGTCCTTCCCCGAGGGCTTCAAGTGGGAGCGCGTGA<br>TGAACTTCGAGGACGGCGGCGTGGTGACCGTGACCCAGGACTCCTCCCTGCAGGACGGC<br>GAGTTCATCTACAAGGTGAAGCTGCGCGGCACCAACTTCCCCTCCGACGGCCCCGTAAT<br>GCAGAAGAAGACCATGGGCTGGGAGGCCTCCTCCGAGCGGATGTACCCCGAGGACGGCG<br>CCCTGAAGGGCGAGATCAAGCAGAGGCTGAAGCTGAAGGACGGCGGCCACTACGACGCT<br>GAGGTCAAGACCACCTACAAGGCCAAGAAGCCCGTGCAGCTGCCCGGCGCCTACAACGT<br>CAACATCAAGTTGGACATCACCTCCCACAACGAGGACTACACCATCGTGGAACAGTACG<br>AACGCGCCGAGGGCCGCCACTCCACCGGCGGCATGGACGAGCTGTACAAGTAATAAGAT<br>ACATTGATGAGTTTGGACAAACCACAACTAGAATGCAGTGAAAAAAATGCTTTATTTGT<br>GAAATTTGTGATGCTATTGCTTTATTTGTAACCATTATAAGCTGCAATAAACAAGTTAG<br>GAACCCCTAGTGATTGGAGTTGGCCACTCCCTCTCTGCGCGCTCGCTCGCTCACTGAGG<br>CCGGGTCGACCAAAGGTCGCCCGACGCCCGGGCTTTGCCCGGGCGGCCTCAGTGAGTCG<br>AGCGAGCGCGCAGCTGCCTGCAGG (SEQ ID NO: 20) |
| Nucleic Acid construct containing the following elements in order of 5' to 3': hSyn promoter and ATP1A3 | AGTGCAAGTGGGTTTTTAGGACCAGGATGAGGCGGGTGGGGGTGCCTACCTGACGACC<br>GACCCCGGACCCACTGGACAAGCACCCAACCCCCATTCCCCAAATTGCGCATCCCCTAA<br>TCAGAGAGGGGGAGGGGAAACAGGATGCGGCGAGGCGCGTGCGCACTGCCAAGCTTCAG<br>CACCGCGGACAGTGCCTTCGCCCCCGCCTGGCGGCGCGCGCCCACCGCCGCCTCAGCAC<br>TGAAGGCGCGCTGACGTCACTCGCCGGTCCCCCGACAAACTCCCCTTCCCGGCCACCTT<br>GGTCGCGTCCGCGCCGCCGCCGGCCCAGCCGGACCGCACCACGCGAGGCGCGAGATAG<br>GGGGGCACGGGCGCGACCCATCTGCGCTGCCGCCGCGGCGACTCAGCGCTGCCTCAGTC<br>TGCGGTGGGCAAGCGGAGGAGTCGTGTCGTGCCTGAGAGCGCAGTCGAGAAGGTACCGA<br>GGAGATCTGCCGCCATGGGGGACAAGAAAGATGACAAGGACTCACCCAAGAAGAACAAG<br>GGCAAGGAGCGCCGGGACCTGGATGACCTCAAGAAGGAGGTGGCTATGACAGAGCCACAA<br>GATGTCAGTGGAAGAGGTCTGCCGGAAATACAACACAGACTGTGTGCAGGGTTTGACCC<br>ACAGCAAAGCCCAGGAGATCCTGGCCCGGGATGGGCCTAACGCACTCACGCCACCGCCT |

TABLE 3-continued

Nucleic Acid Constructs

```
ACCACCCCAGAGTGGGTCAAGTTTTGCCGGCAGCTCTTCGGGGGCTTCTCCATCCTGCT
GTGGATCGGGGCTATCCTCTGCTTCCTGGCCTACGGTATCCAGGCGGGCACCGAGGACG
ACCCCTCTGGTGACAACCTGTACCTGGGCATCGTGCTGGCGGCCGTGGTGATCATCACT
GGCTGCTTCTCCTACTACCAGGAGGCCAAGAGCTCCAAGATCATGGAGTCCTTCAAGAA
CATGGTGCCCCAGCAAGCCCTGGTGATCCGGGAAGGTGAGAAGATGCAGGTGAACGCTG
AGGAGGTGGTGGTCGGGGACCTGGTGGAGATCAAGGGTGGAGACCGAGTGCCAGCTGAC
CTGCGGATCATCTCAGCCCACGGCTGCAAGGTGGACAACTCCTCCCTGACTGGCGAATC
CGAGCCCCAGACTCGCTCTCCCGACTGCACGCACGACAACCCCTTGGAGACTCGGAACA
TCACCTTCTTTTCCACCAACTGTGTGGAAGGCACGGCTCGGGGCGTGGTGGTGGCCACG
GGCGACCGCACTGTCATGGGCCGTATCGCCACCCTGGCATCAGGGCTGGAGGTGGGCAA
GACGCCCATCGCCATCGAGATTGAGCACTTCATCCAGCTCATCACCGGCGTGGCTGTCT
TCCTGGGTGTCTCCTTCTTCATCCTCTCCCTCATTCTCGGATACACCTGGCTTGAGGCT
GTCATCTTCCTCATCGGCATCATCGTGGCCAATGTCCCAGAGGGTCTGCTGGCCACTGT
CACTGTGTGTCTGACGCTGACCGCCAAGCGCATGGCCCGGAAGAACTGCCTGGTGAAGA
ACCTGGAGGCTGTAGAAACCCTGGGCTCCACGTCCACCATCTGCTCAGATAAGACAGGG
ACCCTCACTCAGAACCGCATGACAGTCGCCCACATGTGGTTTGACAACCAGATCCACGA
GGCTGACACCACTGAGGACCAGTCAGGGACCTCATTTGACAAGAGTTCGCACACCTGGG
TGGCCCTGTCTCACATCGCTGGGCTCTGCAATCGCGCTGTCTTCAAGGGTGGTCAGGAC
AACATCCCTGTGCTCAAGAGGGATGTGGCTGGGGATGCGTCTGAGTCTGCCCTGCTCAA
GTGCATCGAGCTGTCCTCTGGCTCCGTGAAGCTGATGCGTGAACGCAACAAGAAAGTGG
CTGAGATTCCCTTCAATTCCACCAACAAATACCAGCTCTCCATCCATGAGACCGAGGAC
CCCAACGACAACCGATACCTGCTGGTGATGAAGGGTGCCCCCGAGCGCATCCTGGACCG
CTGCTCCACCATCCTGCTACAGGGCAAGGAGCAGCCTCTGGACGAGGAAATGAAGGAGG
CCTTCCAGAATGCCTACCTTGAGCTCGGTGGCCTGGGCGAGCGCGTGCTTGGTTTCTGC
CATTATTACCTGCCCGAGGAGCAGTTCCCCAAGGGCTTTGCCTTCGACTGTGATGACGT
GAACTTCACCACGGACAACCTCTGCTTTGTGGGCCTCATGTCCATGATCGACCCACCCC
GGGCAGCCGTCCCTGACGCGGTGGGCAAGTGTCGCAGCGCAGGCATCAAGGTCATCATG
GTCACCGGCGATCACCCCATCACGGCCAAGGCCATTGCCAAGGGTGTGGGCATCATCTC
TGAGGGCAACGAGACTGTGGAGGACATCGCCGCCCGGCTCAACATTCCCGTCAGCCAGG
TTAACCCCCGGGATGCCAAGGCCTGCGTGATCCACGGCACCGACCTCAAGGACTTCACC
TCCGAGCAAATCGACGAGATCCTGCAGAATCACACCGAGATCGTCTTCGCCCGCACATC
CCCCCAGCAGAAGCTCATCATTGTGGAGGGCTGTCAGAGACAGGGTGCAATTGTGGCTG
TGACCGGGGATGGTGTGAACGACTCCCCCGCTCTGAAGAAGGCCGACATTGGGGTGGCC
ATGGGCATCGCTGGCTCTGACGTCTCCAAGCAGGCAGCTGACATGATCCTGCTGGACGA
CAACTTTGCCTCCATCGTCACAGGGGTGGAGGAGGGCCGCCTGATCTTCGACAACCTAA
AGAAGTCCATTGCCTACACCCTGACCAGCAATATCCCGGAGATCACGCCCTTCCTGCTG
TTCATCATGGCCAACATCCCGCTGCCCCTGGGCACCATCACCATCCTCTGCATCGATCT
GGGCACTGACATGGTCCCTGCCATCTCACTGGCGTACGAGGCTGCCGAAAGCGACATCA
TGAAGAGACAGCCCAGGAACCCGCGGACGGACAAATTGGTCAATGAGAGACTCATCAGC
ATGGCCTACGGGCAGATTGGAATGATCCAGGCTCTCGGTGGCTTCTTCTCTTACTTTGT
GATCCTGGCAGAAAATGGCTTCTTGCCCGGCAACCTGGTGGGCATCCGGCTGAACTGGG
ATGACCGCACCGTCAATGACCTGGAAGACAGTTACGGGCAGCAGTGGACATACGAGCAG
AGGAAGGTGGTGGAGTTCACCTGCCACACGGCCTTCTTTGTGAGCATCGTTGTCGTCCA
GTGGGCCGATCTGATCATCTGCAAGACCCGGAGGAACTCGGTCTTCCAGCAGGGCATGA
AGAACAAGATCCTGATCTTCGGGCTGTTTGAGGAGACGGCCCTGGCTGCCTTCCTGTCC
TACTGCCCCGGCATGGACGTGGCCCTGCGCATGTACCCTCTCAAGCCCAGCTGGTGGTT
CTGTGCCTTCCCCTACAGTTTCCTCATCTTCGTCTACGACGAAATCCGCAAACTCATCC
TGCGCAGGAACCCAGGGGGTTGGGTGGAGAAGGAAA (SEQ ID NO: 21)
```

In other embodiments, the recombinant AAV vector comprises AAV1. In one embodiment, the recombinant AAV vector comprises a nucleotide sequence encoding ATP1A3, the vector comprising AAV1-pBK828-1-ATP1A3-cherry. An AAV1-pBK828-1-ATP1A3-cherry vector can comprise an ITR, a human Syn promoter, an ATP1A3 open reading frame (ORF), linkers, a Myc tag, a FLAG tag, a P2A sequence, a mCherry open reading frame, a Sv40 PolyA tail, and a flanking ITR. In some embodiments, the AAV1-pBK828-1-ATP1A3-cherry vector can comprise the following elements operably linked in order of 5' to 3': an AAV-ITR, a human Syn promoter, an ATP1A3 transgene, a linker sequence, a Myc tag, a linker sequence, a FLAG tag, a linker sequence, a mCherry tag, a Sv40 PolyA sequence, and an AAV-ITR.

In yet another embodiment, the recombinant AAV vector comprises AAV1-hSyn-mCherry-pBK292-1, which does not contain a transgene can be used as a control vector to the AAV1-pBK828-1-ATP1A3-cherry vector.

As used herein, the term "open reading frame (ORF)" refers to the parts of a reading frame that has the ability to be translated. An ORF can be a continuous chain of codons that begins with a start codon (e.g., ATG) and ends at a stop codon (e.g., TAA, TAG, TGA). A reading frame is a sequence of nucleotides that are read as codons specifying amino acids.

In some embodiments, the AAV vector is pseudotyped, which refers to the practice of creating hybrids of certain AAV strains to be able to refine the interaction with desired target cells. The hybrid AAV can be created by taking a capsid from one strain and the genome from another strain. For example, AAV2/5, a hybrid with the genome of AAV2 and the capsid of AAV5, can be used to achieve more accuracy and range in brain cells than AAV2 would be able to achieve unhybridized. Production of pseudotyped rAAV is disclosed in, for example, WO01/83692.

Other types of rAAV variants, for example rAAV with capsid mutations, are also contemplated. See, for example, Marsic et al., Molecular Therapy, 22(11): 1900-1909 (2014). It is understood that the nucleotide sequences of the genomes of various AAV serotypes are known in the art.

Examples of recombinant AAV that can be constructed to comprise the nucleic acid molecules of the disclosure are set out in International Patent Application No. PCT/US2012/047999 (WO 2013/016352) incorporated by reference herein in its entirety.

Any suitable method known in the art can be used to produce AAV vectors. In one particular method, AAV stocks can be produced by co-transfection of a rep/cap vector plasmid encoding AAV packaging functions and the vector plasmid containing the recombinant AAV genome into human cells infected with the helper adenovirus. General principles of recombinant AAV production are reviewed in, for example, Carter, 1992, Current Opinions in Biotechnology, 1533-539; and Muzyczka, (1992) *Curr. Topics in Microbial. and Immunol.,* 158:97-129). Various approaches are described in Ratschin et al., *Mol. Cell. Biol.* 4:2072 (1984); Hermonat et al., *Proc. Natl. Acad. Sci. USA,* 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. Nos. 5,173,414; 5,658,776; WO 95/13392; WO 96/17947; WO 97/09441; WO 97/08298; WO 97/21825; WO 97/06243; WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. Nos. 5,786, 211; 5,871,982; and 6,258,595. The foregoing documents are hereby incorporated by reference in their entirety herein, with particular emphasis on those sections of the documents relating to recombinant AAV production.

The recombinant viral vectors (e.g., rAAV) may be purified by methods standard in the art such as by column chromatography or cesium chloride gradients. Methods for purifying recombinant viral vectors from helper virus are known in the art.

The nucleic acid encoding ATP1A3 can be provided to the cell using any method known in the art. For example, the template can be supplied by a non-viral (e.g., plasmid) or viral vector.

The AAV rep and/or cap genes can alternatively be provided by a packaging cell that stably expresses the genes. A method of generating a packaging cell is to create a cell line that stably expresses all the necessary components for viral (e.g., AAV) particle production. For example, in one embodiment, a plasmid (or multiple plasmids) comprising a viral rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

In one embodiment, packaging cells can be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

In still further embodiments, the delivery vector is a hybrid Ad-AAV delivery vector. Briefly, the hybrid Ad-AAV vector comprises an adenovirus vector genome comprising adenovirus (i) 5' and 3' cis-elements for viral replication and encapsidation and, further, (ii) a recombinant AAV vector genome comprising the AAV 5' and 3' inverted terminal repeats (ITRs), an AAV packaging sequence, and a heterologous sequence(s) flanked by the AAV ITRs, where the recombinant AAV vector genome is flanked by the adenovirus 5' and 3' cis-elements. The adenovirus vector genome can further be deleted, as described above.

Another vector for use in the present disclosure comprises Herpes Simplex Virus (HSV). HSV can be modified for the delivery of transgenes to cells by producing a vector that exhibits only the latent function for long-term gene maintenance. HSV vectors are useful for nucleic acid delivery because they allow for a large DNA insert of up to or greater than 20 kilobases; they can be produced with extremely high titers; and they have been shown to express transgenes for a long period of time in the central nervous system as long as the lytic cycle does not occur.

Herpesvirus may also be used as a helper virus in AAV packaging methods. Hybrid herpesviruses encoding the AAV Rep protein(s) may advantageously facilitate scalable AAV vector production schemes. A hybrid herpes simplex virus type I (HSV-1) vector expressing the AAV-2 rep and cap genes has been described (Conway et al. (1999) *Gene Therapy* 6:986 and WO 00/17377.

In other embodiments of the present disclosure, the delivery vector of interest is a retrovirus. Retroviruses normally bind to a species specific cell surface receptor, e.g., CD4 (for HIV); CAT (for MLV-E; ecotropic Murine leukemic virus E); RAM1/GLVR2 (for murine leukemic virus-A; MLV-A); GLVR1 (for Gibbon Ape leukemia virus (GALV) and Feline leukemia virus B (FeLV-B)). The development of specialized cell lines (termed "packaging cells") which produce only replication-defective retroviruses has increased the utility of retroviruses for gene therapy, and defective retroviruses are characterized for use in gene transfer for gene therapy purposes. A replication-defective retrovirus can be packaged into virions which can be used to infect a target cell through the use of a helper virus by standard techniques.

Yet another suitable vector is a lentiviral vector. Lentiviruses are a subtype of retroviruses but they have the unique ability to infect non-dividing cells, and therefore can have a ride range of potential applications.

Yet another suitable vector is a poxvirus vector. These viruses contain more than 100 proteins. Extracellular forms of the virus have two membranes while intracellular particles only have an inner membrane. The outer surface of the virus is made up of lipids and proteins that surround the biconcave core. Poxviruses are very complex antigenically, inducing both specific and cross-reacting antibodies after infection. Poxvirus can infect a wide range of cells. Poxvirus gene expression is well studied due to the interest in using vaccinia virus as a vector for expression of transgenes.

In another representative embodiment, the nucleic acid sequence encoding ATP1A3 is provided by a replicating rAAV virus. In still other embodiments, an AAV provirus comprising the nucleic acid sequence encoding ATP1A3 can be stably integrated into the chromosome of the cell.

To enhance virus titers, helper virus functions (e.g., adenovirus or herpesvirus) that promote a productive AAV infection can be provided to the cell. Helper virus sequences necessary for AAV replication are known in the art. Typically, these sequences will be provided by a helper adenovirus or herpesvirus vector. Alternatively, the adenovirus or herpesvirus sequences can be provided by another non-viral or viral vector, e.g., as a non-infectious adenovirus miniplasmid that carries all of the helper genes that promote efficient AAV production.

Further, the helper virus functions may be provided by a packaging cell with the helper sequences embedded in the chromosome or maintained as a stable extrachromosomal element. Generally, the helper virus sequences cannot be packaged into AAV virions, e.g., are not flanked by TRs.

In addition to viral transfer methods, such as those illustrated above, non-viral methods can also be employed. Many non-viral methods of gene transfer rely on normal mechanisms used by mammalian cells for the uptake and intracellular transport of macromolecules. In particular embodiments, non-viral delivery systems rely on endocytic pathways for the uptake of the nucleic acid molecule by the targeted cell. Exemplary nucleic acid delivery systems of this type include liposomal derived systems, poly-lysine conjugates, and artificial viral envelopes.

In particular embodiments, plasmid vectors are used in the practice of the present disclosure. Naked plasmids can be introduced into cells by injection into the tissue. Expression can extend over many months. Cationic lipids can aid in introduction of DNA into some cells in culture. Injection of cationic lipid plasmid DNA complexes into the circulation of mice can result in expression of the DNA in organs (e.g., the lung). One advantage of plasmid DNA is that it can be introduced into non-replicating cells.

In a representative embodiment, a nucleic acid molecule (e.g., a plasmid) can be entrapped in a lipid particle bearing positive changes on its surface and, optionally, tagged with antibodies against cell surface antigens of the target tissue.

Liposomes that consist of amphiphilic cationic molecules are useful non-viral vectors for nucleic acid delivery in vitro and in vivo. The positively charged liposomes are believed to complex with negatively charged nucleic acids via electrostatic interactions to form lipid:nucleic acid complexes. The lipid:nucleic acid complexes have several advantages as gene transfer vectors. Unlike viral vectors, the lipid:nucleic acid complexes can be used to transfer expression cassettes of essentially unlimited size. Since the complexes lack proteins, they can evoke fewer immunogenic and inflammatory responses. Moreover, they cannot replicate or recombine to form an infectious agent and have low integration frequency.

Amphiphilic cationic lipid:nucleic acid complexes can be used for in vivo transfection both in animals and in humans and can be prepared to have a long shelf-life.

In addition, vectors according to the present disclosure can be used in diagnostic and screening methods, whereby a nucleic acid encoding ATP1A3 is transiently or stably expressed in a cell culture system, or alternatively, a transgenic animal model screening methods, whereby a nucleic acid of interest is transiently or stably expressed in a cell culture system, or alternatively, a transgenic animal model.

The vectors of the present invention can also be used for various non-therapeutic purposes, including but not limited to use in protocols to assess gene targeting, clearance, transcription, translation, etc., as would be apparent to one skilled in the art. The vectors can also be used for the purpose of evaluating safety (spread, toxicity, immunogenicity, etc.). Such data, for example, are considered by the United States Food and Drug Administration as part of the regulatory approval process prior to evaluation of clinical efficacy.

Gene Therapy Methods, Pharmaceutical Formulations, and Modes of Administration

Another aspect of the present disclosure provides a composition, pharmaceutical formulation comprising, consisting, or consisting essentially of vector comprising the an ATPase transgene (e.g., ATP1A3) and/or nucleic acid expression cassettes as described herein.

In some embodiments, compositions of the present disclosure comprise, consist of, or consist essentially of a recombinant viral vector (e.g., rAAV) and/or a pharmaceutically acceptable carrier and/or excipient, and, optionally, other medicinal agents, pharmaceutical agents, stabilizing agents, buffers, carriers, adjuvants, diluents, etc. For injection, the carrier will typically be a liquid. For other methods of administration, the carrier may be either solid or liquid. For inhalation administration, the carrier will be respirable, and optionally can be in solid or liquid particulate form.

By "pharmaceutically acceptable" it is meant a material that is not biologically or otherwise undesirable, i.e., the material can be administered to a subject along with the isolated nucleic acid or vector without causing any undesirable biological effects such as toxicity. Thus, such a pharmaceutical composition can be used, for example, in transfection of a cell ex vivo or in administering an isolated nucleic acid or vector directly to a subject.

The compositions may also comprise other ingredients such as diluents and adjuvants. Acceptable carriers, diluents and adjuvants are nontoxic to recipients and are preferably inert at the dosages and concentrations employed, and may include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counter ions such as sodium; and/or nonionic surfactants such as Tween, pluronics or polyethylene glycol (PEG).

The pharmaceutical carriers, diluents or excipients suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating actions of microorganisms such as bacteria and fungi. The carrier can be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating such as lecithin, by the maintenance of the required particle size in the case of a dispersion and by the use of surfactants. The prevention of the action of microorganisms can be brought about by various antibacterial and antifungal agents, for example, parabens, chlorobutanol, phenol, sorbic acid, thimerosal and the like. In many cases it will be preferable to include isotonic agents, for example, sugars or sodium chloride. Prolonged absorption of the injectable compositions can be brought about by use of agents delaying absorption, for example, aluminum monostearate and gelatin.

In some embodiments, sterile injectable solutions are prepared by incorporating the recombinant viral vector (e.g., rAAV) in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique that yield a powder of the active ingredient plus any additional desired ingredient from the previously sterile-filtered solution thereof.

For purposes of intramuscular injection, solutions in an adjuvant such as sesame or peanut oil or in aqueous propylene glycol can be employed, as well as sterile aqueous solutions. Such aqueous solutions can be buffered, if desired, and the liquid diluent first rendered isotonic with saline or glucose. Solutions of recombinant viral vector (e.g., rAAV) as a free acid (DNA contains acidic phosphate groups) or a pharmacologically acceptable salt can be prepared in water suitably mixed with a surfactant such as hydroxpropylcellulose. A dispersion of recombinant viral vector (e.g., rAAV) can also be prepared in glycerol, liquid polyethylene glycols and mixtures thereof and in oils. Under ordinary conditions of storage and use, these preparations contain a preservative to prevent the growth of microorganisms. In this connection, the sterile aqueous media employed are all readily obtainable by standard techniques well-known to those skilled in the art.

Pharmaceutical compositions can be prepared as injectable formulations or as topical formulations to be delivered to the subject by transdermal transport. Numerous formulations for both intramuscular injection and transdermal transport have been previously developed and can be used in the practice of the invention. The recombinant viral vector can be used with any pharmaceutically acceptable carrier and/or excipient for ease of administration and handling.

Titers of recombinant viral vectors (e.g., rAAV) to be administered according to the methods of the present disclosure will vary depending, for example, on the particular recombinant viral vector, the mode of administration, the treatment goal, the individual, and the cell type(s) being targeted, and may be determined by methods standard in the art.

In the case of a viral vector, virus particles can be contacted with the cells at the appropriate multiplicity of infection according to standard transduction methods appropriate for the particular target cells. Titers of virus to administer can vary, depending upon the target cell type and the particular virus vector, and can be determined by those of skill in the art. Typically, at least about $10^3$ virus particles, at least about $10^5$ particles, at least about $10^7$ particles, at least about $10^9$ particles, at least about $10^{11}$ particles, or at least about $10^{12}$ particles are administered to the cell. In exemplary embodiments, about $10^7$ to about $10^{15}$ particles, about $10^7$ to about $10^{13}$ particles, about $10^8$ to about $10^{12}$ particles, about $10^{10}$ to about $10^{15}$ particles, about $10^{11}$ to about $10^{15}$ particles, about $10^{12}$ to about $10^{14}$ particles, or about $10^{12}$ to about $10^{13}$ particles are administered Dosages may also be expressed in units of viral genomes (vg).

The cell to be administered the vectors of the disclosure can be of any type, including but not limited to neuronal cells (including cells of the peripheral and central nervous systems), retinal cells, epithelial cells (including dermal, gut, respiratory, bladder, pulmonary, peritoneal and breast tissue epithelium), muscle (including cardiac, smooth muscle, including pulmonary smooth muscle cells, skeletal muscle, and diaphragm muscle), pancreatic cells (including islet cells), kidney cells, hepatic cells (including parenchyma), cells of the intestine, fibroblasts (e.g., skin fibroblasts such as human skin fibroblasts), fibroblast-derived cells, endothelial cells, intestinal cells, germ cells, lung cells (including bronchial cells and alveolar cells), prostate cells, stem cells, progenitor cells, dendritic cells, and the like. Moreover, the cells can be from any species of origin, as indicated above Methods of transducing a target cell with a vector according to the present disclosure are contemplated by the present disclosure. The term "transduction" is used herein to refer to the administration/delivery of an ATPase transgene to a recipient cell either in vivo or in vitro, via a replication-deficient recombinant viral vector (e.g., rAAV) of the present disclosure thereby resulting in expression of an ATPase by the recipient cell. Thus, the present disclosure provides methods of administering an effective dose (or doses, administered essentially simultaneously or doses given at intervals) of a recombinant viral vector (e.g., rAAV) that encodes ATP1A3 to a subject in need thereof.

The in vivo transduction methods comprise the step of administering an effective dose, or effective multiple doses, of a nucleic acid expression cassette or composition comprising a recombinant viral vector of the present disclosure to an animal (including a human being) in need thereof. If the dose is administered prior to development of a disorder/disease, the administration is prophylactic. If the dose is administered after the development of a disorder/disease, the administration is therapeutic. In embodiments of the present disclosure, an effective dose is a dose that alleviates (eliminates or reduces) at least one symptom associated with the disorder/disease state being treated, that slows or prevents progression to a disorder/disease state, that slows or prevents progression of a disorder/disease state, that diminishes the extent of disease, that results in remission (partial or total) of disease, and/or that prolongs survival. An example of a disease contemplated for prevention or treatment with methods of the present disclosure is AHC.

Transduction with a recombinant viral vector (e.g., rAAV) may also be carried out in vitro. In one embodiment, desired target cells are removed from the subject, transduced with recombinant viral vector (e.g., rAAV) and reintroduced into the subject. Alternatively, syngeneic or xenogeneic target cells can be used where those cells will not generate an inappropriate immune response in the subject.

Suitable methods for the transduction of a recombinant viral vector (e.g., rAAV) or the reintroduction of transduced cells into a subject are known in the art. In one embodiment, cells can be transduced in vitro by combining the recombinant viral vector (e.g., rAAV) with target cells, e.g., in appropriate media, and screening for those cells harboring the DNA of interest using conventional techniques such as Southern blots and/or PCR, or by using selectable markers. A recombinant viral vector (e.g., rAAV) or transduced cells can then be formulated into pharmaceutical compositions, and the composition introduced into the subject by various techniques, such as by intramuscular, intravenous, subcutaneous and intraperitoneal injection, by injection into smooth and cardiac muscle, using e.g., a catheter, intrathecal, intracisternal, intraventricular or intraparenchymal into the brain.

Transduction of cells with recombinant viral vector (e.g., rAAV) of the present disclosure can result in the in sustained expression of ATP1A3 or another ATPase gene. The present disclosure thus provides methods of administering/delivering a recombinant viral vector (e.g., rAAV) that expresses, for example, ATP1A3 to a subject (e.g., a human patient). These methods include transducing tissues (including, but not limited to, tissues such as nervous system and muscle, organs such as brain, heart, liver, and glands such as salivary glands) with one or more recombinant viral vector (e.g., rAAV) of the present disclosure. Transduction may be carried out with gene cassettes comprising tissue specific control elements as described herein.

In some embodiments, gene editing is accomplished by transducing cells with a nuclease, such as zinc finger nuclease(s) or CRISPR/Cas9, plus normal ATPase sequences flanking a mutation in ATPase as a donor template. In such embodiments, the transduction with the nuclease cleaves the ATPase gene near a pathogenic variant/mutation followed by homology directed repair to correct the variant/mutation causing symptoms for an individual patient thereby treating and/or preventing ATPase-related diseases.

The isolated nucleic acids, vectors, and compositions of the present disclosure may further be used in various methods.

Another aspect of the present disclosure provides a method of treating or preventing an ATPase-mediated disease in a subject, the method comprising, consisting of, or consisting essentially of administering to the subject a therapeutically effective amount of the nucleic acid expression cassette, vector, composition, or pharmaceutical compositions comprising a nucleic acid encoding an ATPase (e.g., ATP1A3) as described in the present disclosure such that the ATPase-mediated disease in the subject is prevented.

As used herein, the term "subject" and "patient" are used interchangeably and refer to both human and nonhuman animals. The term "nonhuman animals" of the disclosure includes all vertebrates, e.g., mammals and non-mammals, such as nonhuman primates, sheep, dog, cat, horse, cow, chickens, amphibians, reptiles, and the like. The subject can be a human patient that is at risk for, or suffering from, an ATP1A3-mediated disease. The subject can also be a human patient that is at risk for, or suffering from, a disease caused by a mutation in the ATP1A3 gene. The human patient can be of any age (e.g., an infant, child, or adult).

As used herein, "treatment" or "treating" refers to the clinical intervention made in response to a disease, disorder or physiological condition manifested by a patient or to which a patient may be susceptible. The aim of treatment includes the alleviation or prevention of symptoms, slowing or stopping the progression or worsening of a disease, disorder, or condition and/or the remission of the disease, disorder or condition.

An "effective amount" or "therapeutically effective amount" as used herein means an amount which provides a therapeutic or prophylactic benefit. Effective amounts of the nucleic acid molecules and/or compositions and/or pharmaceutical compositions can be determined by a physician with consideration of individual differences in age, weight, and condition of the patient (subject).

An effective amount of a therapeutic agent is one that will decrease or ameliorate the symptoms normally by at least 10%, more normally by at least 20%, most normally by at least 30%, typically by at least 40%, more typically by at least 50%, most typically by at least 60%, often by at least 70%, more often by at least 80%, and most often by at least 90%, conventionally by at least 95%, more conventionally by at least 99%, and most conventionally by at least 99.9%.

The term "disease" as used herein includes, but is not limited to, any abnormal condition and/or disorder of a structure or a function that affects a part of an organism. It may be caused by an external factor, such as an infectious disease, or by internal dysfunctions, such as cancer, cancer metastasis, and the like.

The term "administration" or "administering" as it applies to a human, primate, mammal, mammalian subject, animal, veterinary subject, placebo subject, research subject, experimental subject, cell, tissue, organ, or biological fluid, refers without limitation to contact of an exogenous ligand, reagent, placebo, small molecule, pharmaceutical agent, therapeutic agent, diagnostic agent, or composition to the subject, cell, tissue, organ, or biological fluid, and the like. "Administration" can refer, e.g., to therapeutic, pharmacokinetic, diagnostic, research, placebo, and experimental methods. Treatment of a cell encompasses exposure of the cell to a reagent (e.g., a nucleic acid molecule), as well as contact of a reagent to a fluid, where the fluid is in contact with the cell. "Administering" also encompasses in vitro and ex vivo treatments, e.g., of a cell, by a reagent, diagnostic, binding composition, or by another cell.

Administration of an effective dose of the isolated nucleic acids, vectors, and compositions may be by routes standard in the art including, but not limited to, intrathecal, intracisterna magna, intracerebroventircular, intrahippocampal, intramuscular, parenteral, intravenous, oral, buccal, nasal, pulmonary, intracranial-intra-parenchymal, intraosseous, or intraocular. Intrahippocampal administration can comprise injecting the isolated nucleic acid, vector, or composition into the substance of the hippocampal brain (intra-parenchymal). Intracerebroventricular can comprise injecting the isolated nucleic acid, vector, or composition into the ventricle, which is filled with cerebrospinal fluid and is next to the hippocampus but not part of it.

Route(s) of administration and serotype(s) of viral (e.g., AAV) components of the recombinant viral vector (e.g., rAAV, and in particular, the AAV ITRs and capsid protein) of the present disclosure may be chosen and/or matched by those skilled in the art taking into account the disease state being treated and the target cells/tissue(s) that are to express the ATP1A3.

The present disclosure further provides for local administration and systemic administration of an effective dose of rAAV and compositions of the present disclosure including combination therapy as provided herein. For example, systemic administration is administration into the circulatory system so that the entire body is affected. Systemic administration includes enteral administration such as absorption through the gastrointestinal tract and parenteral administration through injection, infusion or implantation.

In particular, actual administration of a vector (e.g., rAAV) of the present disclosure can be accomplished by using any physical method that will transport the vector into the target tissue of the subject.

The virus vectors and virus capsids can be administered to tissues of the CNS (e.g., brain, eye) and may advantageously result in broader distribution of the virus vector or capsid than would be observed in the absence of the present disclosure.

Administration according to the present disclosure includes, but is not limited to, injection into the ventricles, cisterna magna, spinal theca, muscle, the bloodstream and/or directly into the brain.

In some embodiments, the nucleic acid molecules, vectors, and/or compositions of the disclosure can be administered to the CNS (e.g., to the brain or to the eye). The virus vector and/or capsid may be introduced into the spinal cord, brainstem (medulla oblongata, pons), midbrain (hypothalamus, thalamus, epithalamus, pituitary gland, substantia nigra, pineal gland), cerebellum, telencephalon (corpus striatum, cerebrum including the occipital, temporal, parietal and frontal lobes cortex, basal ganglia, hippocampus and portaamygdala), limbic system, neocortex, corpus striatum, cerebrum, and inferior colliculus. The nucleic acid molecules, vectors, and/or compositions of the disclosure can also be administered to different regions of the eye such as the retina, cornea and/or optic nerve.

The nucleic acid molecules, vectors, and/or compositions can be delivered into the cerebrospinal fluid (e.g, by lumbar puncture) for more disperse administration of the delivery vector.

The nucleic acid molecules, vectors, and/or compositions can be administered to the desired region(s) of the CNS by any route known in the art, including but not limited to, intracerebroventricular, intra-cisterna magnal, intraparenchymal, intracranial, intrathecal, intra-ocular, intracerebral, intraventricular, intravenous (e.g., in the presence of a sugar such as mannitol), intranasal, intra-aural, intra-ocular (e.g., intra-vitreous, sub-retinal, anterior chamber) and peri-ocular (e.g., sub-Tenon's region) delivery as well as intramuscular delivery with retrograde delivery to motor neurons.

In other embodiments, the nucleic acid molecules, vectors, and/or compositions can be administered in a liquid formulation by direct injection (e.g., stereotactic injection) to the desired region or compartment in the CNS. In other embodiments, the virus vector can be provided by topical application to the desired region or by intra-nasal administration of aerosol formulation. Administration to the eye, may be by topical application of liquid droplets. As a further alternative, the virus vector and/or capsid may be administered as a solid, slow-release formulation.

In other embodiments, more than one route of administration can be utilized (e.g., ICV and ICM administration).

For example, resuspending the recombinant viral vector (e.g., rAAV) in phosphate buffered saline (PBS) can be sufficient to provide a vehicle useful for muscle tissue expression, and there are no known restrictions on the carriers or other components that can be co-administered with the recombinant viral vector (e.g., rAAV, although compositions that degrade DNA should be avoided in the normal manner with rAAV). In cases where the recombinant viral vector comprises rAAV, the capsid proteins of a rAAV may be modified so that the rAAV is targeted to a particular target tissue of interest such as muscle.

Dosages will depend upon the mode of administration, the severity of the disease or condition to be treated, the individual subject's condition, the particular vector, and the gene to be delivered, and can be determined in a routine manner. In some embodiments, the isolated nucleic acid molecule or vector is administered to the subject in a therapeutically effective amount, as that term is defined above.

The dose of vector (e.g., rAAV) to be administered in methods disclosed herein will vary depending, for example, on the particular recombinant viral vector, the mode of administration, the treatment goal, the individual, and the cell type(s) being targeted, and may be determined by methods standard in the art. Titers of each recombinant viral vector (e.g., rAAV) administered may range from about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$, about $1 \times 10^{14}$, or to about $1 \times 10^{15}$ or more per ml. Dosages may also be expressed in units of viral genomes (vg) (i.e., $1 \times 10^7$ vg, $1 \times 10^8$ vg, $1 \times 10^9$ vg, $1 \times 10^{10}$ vg, $1 \times 10^{11}$ vg, $1 \times 10^{12}$ vg, $1 \times 10^{13}$ vg, $1 \times 10^{14}$ vg, $1 \times 10^{15}$ respectively). Dosages may also be expressed in units of viral genomes (vg) per kilogram (kg) of bodyweight (i.e., $1 \times 10^{10}$ vg/kg, $1 \times 10^{11}$ vg/kg, $1 \times 10^{12}$ vg/kg, $1 \times 10^{13}$ vg/kg, $1 \times 10^{14}$ vg/kg, $1 \times 10^{15}$ vg/kg respectively). Methods for titering viral vectors such as AAV are described in Clark et al., *Hum. Gene Ther.*, 10:1031-1039 (1999).

In some embodiments, more than one administration (e.g., two, three, four or more administrations) may be employed to achieve the desired level of gene expression over a period of various intervals, e.g., daily, weekly, monthly, or yearly.

Delivery to a target tissue can also be achieved by delivering a depot comprising the virus vector and/or capsid. In representative embodiments, a depot comprising the vector and/or capsid is implanted into skeletal, cardiac and/or diaphragm muscle tissue or the tissue can be contacted with a film or other matrix comprising the virus vector and/or capsid.

Combination therapies are also contemplated by the present disclosure. Combination as used herein includes both simultaneous treatment and sequential treatments. Combinations of methods of the present disclosure with standard medical treatments are specifically contemplated, as are combinations with alternative vectors mentioned above, novel vectors that are engineered and generated to enhance the effect of therapy and novel therapies.

Kits

Other aspects of the present disclosure provides a kit for the prevention and/or treatment of a cancer in subject, the kit comprising, consisting of, or consisting essentially of a composition as provided herein and instructions for use.

Yet another aspect of the present disclosure provides all that is disclosed and illustrated herein.

The following Examples are provided by way of illustration and not by way of limitation.

EXAMPLES

Example 1: Mouse Model that Reproduces the Manifestations of AHC Provides Evidence for Translation of Gene Therapy into Human Application There are currently six mouse models of ATP1A3 mutations. (Clapcote et al. (2006) *Proc Natl Acad Sci USA*, 106(33): 14085-14090; Hunanyan et al. (2015) *Epilepsia* 56(1):82-93; Hunanyan et al. (2018) *Epilepsia* 59(7): 1455-1468; Masoud et al. (2017) *Curr Treat Options Neurol.* 19(2):8; Heinzen et al. (2012) *Nat Genet.* 44(9):1030-1034; Helseth et. al. (2018) *Neurobiol Dis.* 119:100-112; Holm et al. (2016) *Biochim Biophys Acta.* 1857(11):1807-1828; Ikeda et al. (2017) *Brain Res.* 1666: 27-37). The heterozygous Mashlool and the Matoub mouse models are the only models that reproduce all the manifestations of AHC (Hunanyan et al. (2015) *Epilepsia* 56(1):82-93; Helseth et. al. (2018) *Neurobiol Dis.* 119:100-112). Each of these knock-in mice, as reported, carries one of the two most common mutations on a C57BL/6J background. Mashlool (Mashl$^{+/-}$) carries the D801N mutation, which is the most common mutation (40% of AHC patients) that causes AHC of average severity in humans. The Matoub mouse (Matb$^{+/}$) carries the E815K mutation, which is the second most common mutation (26% of AHC patients) and causes the most severe phenotype of AHC in humans. The Mashlool and the Matoub mice have spontaneous as well as stress (cold-water exposure) induced hemiplegias, dystonias and epileptic seizures. Both also, similar to human phenotype, have reduction in induced hemiplegia in response to flunarizine but no other benefits from this medication (Hunanyan et al. (2015)

*Epilepsia* 56(1):82-93; Hunanyan et al. (2018) *Epilepsia* 59(7): 1455-1468; Masoud et al. (2017) *Curr Treat Options Neurol.* 19(2):8; Mikati et al. (2000) *Pediatr Neurol.* 23(2): 134-141; Helseth et al. (2018) *Neurobiol Dis.* 119:100-112). The response to flunarizine is another unique validation of these two models that has not been demonstrated in any other model.

For the Examples described herein, the D801N (Mashl$^{+/-}$) mutant was chosen to study because it is the most common mutation in humans over the E815K (Matb$^{+/}$) mutant that has prohibitive mortality limiting the ability to maintain a thriving colony and to carry out long term experimentation. In addition to paroxysmal spells, prepubescent and adult D801N mice also manifest behavioral abnormalities that closely parallel AHC morbidity in humans. These include increased mortality as well as balance, impulsivity, memory, and gait, abnormalities. (Hunanyan et al. (2015) *Epilepsia* 56(1):82-93; Hunanyan et al. (2018) *Epilepsia* 59(7): 1455-1468). D801N mice also have predisposition to spreading depolarization, increased neuronal excitability and impaired firing of GABAergic fast spiking inhibitory interneurons. (Hunanyan et al. (2015) *Epilepsia* 56(1):82-93; Hunanyan et al. (2018) *Epilepsia* 59(7): 1455-1468). Thus, the D801N (Mashl$^{+/-}$) model can be used to help develop novel therapies that can be translated to clinical applications to treat AHC and other ATP1A3 related diseases mentioned above. In most of the experiments described herein, the P10 age group was selected to study as it corresponds to infancy in humans the age at which AHC symptoms start. The behavioral testing was performed at around P40, which corresponds to adolescence in humans, the age at which the AHC manifestations have been established for at least 10 years.

Example 2: Intracerebroventricular (ICV) Injection of AAV9 Active Vector Results in Robust Increases in ATPase Activity in Brain Regions Contiguous to the Injection Site To determine whether ICV injection of AAV9 active vector can result in increases in ouabain sensitive ATPase activity in brain regions we performed ATPase enzyme activity assays as described previously (Clapcote et al. (2006) *Proc Natl Acad Sci USA*, 106(33): 14085-14090; Ye et al. (2017) *EMBO J.*, 36(16): 2419-2434).

Figure 4:
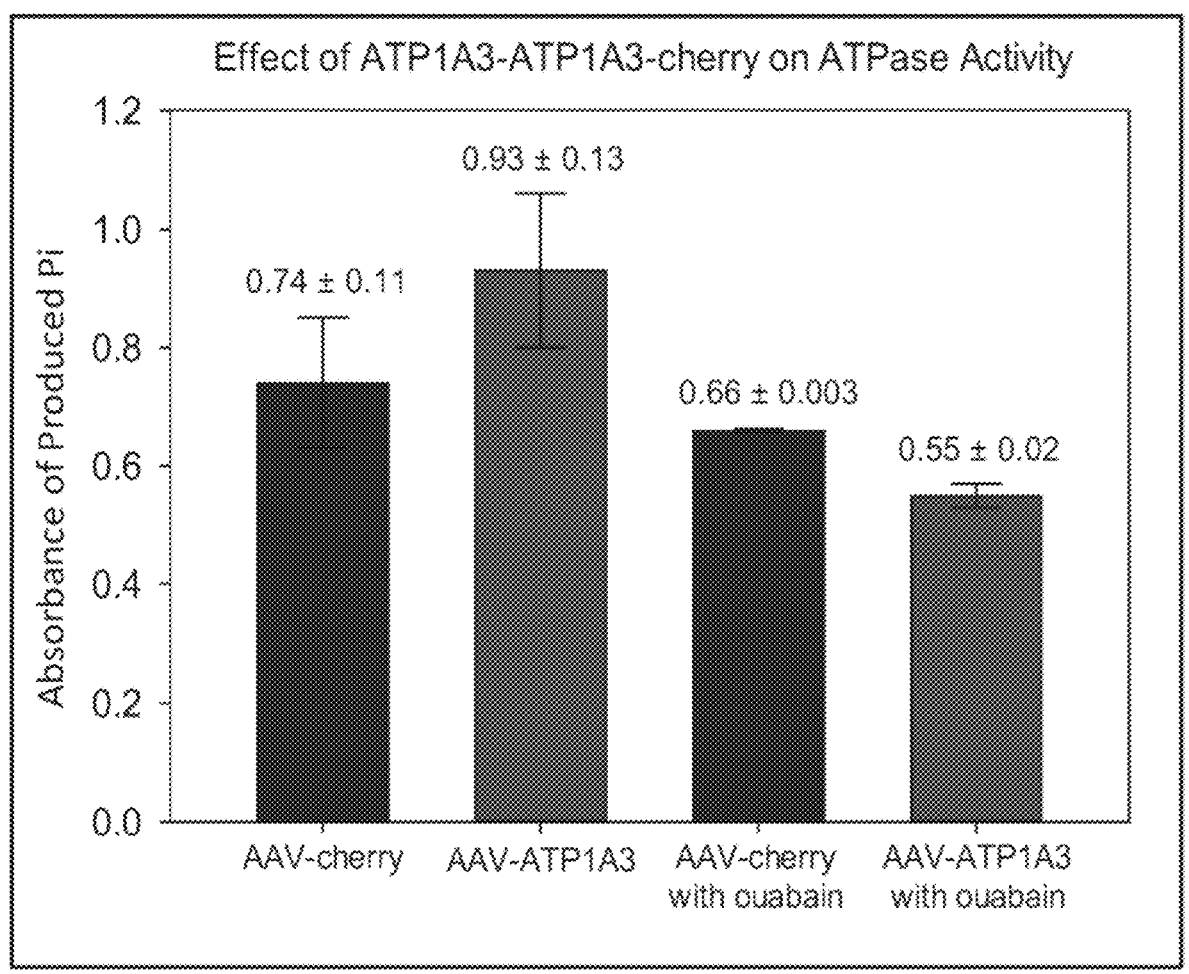
FIG. 4 is a bar graph showing the effect of AAV-ATP1A3 on ATPase activity in the hippocampus of adult wild type (WT) mice injected with AAV-ATP1A3-cherry (n=2) virus into the hippocampus as compared to those injected with AAV-cherry (n=2) in the presence and absence of 3 mM ouabain (specific inhibitor of Na/K-ATPase) in accordance with one embodiment of the present disclosure. AAV injected 1 μL/per hemisphere, intra-parenchymal, into each dorsal hippocampus ($4\times10^{13}$ vg/mL, total 2 μL per mouse).

Briefly, WT mice were injected intrahippocampally with $4\times10^{10}$ vg (1 µl in each side) of AAV9-Syn-ATP1A3-p2a-Cherry-SV40polyA (FIG. 1) or with a similar dose of control vector (vector lacking the ATP1A3 transgene). A 22% increase in total ATPase activity in hippocampus in mice injected with AAV9-Syn-ATP1A3-p2a-Cherry-SV40polyA (n=2) was observed as compared those injected with the control vector (n=2), and even higher (375%) in the ouabain sensitive fraction (FIG. 4). There was no increase in the ouabain insensitive fraction indicating that the increase in total activity was due to increases in the oubain sensitive fraction as calculated from FIG. 4 (AAV-ATP1A3-ouabain-sensitive-fraction=0.93–0.55=0.38; AAV-cherry-ouabain-sensitive-fraction=0.74–0.66=0.08; ratio=0.38/0.08=4.75 fold or 375% increase). AAV injected 1 µL/per hemisphere, intra-parenchymal, into each dorsal hippocampus ($4\times10^{13}$ vg/mL, total 2 µL per mouse).

Figure 5:
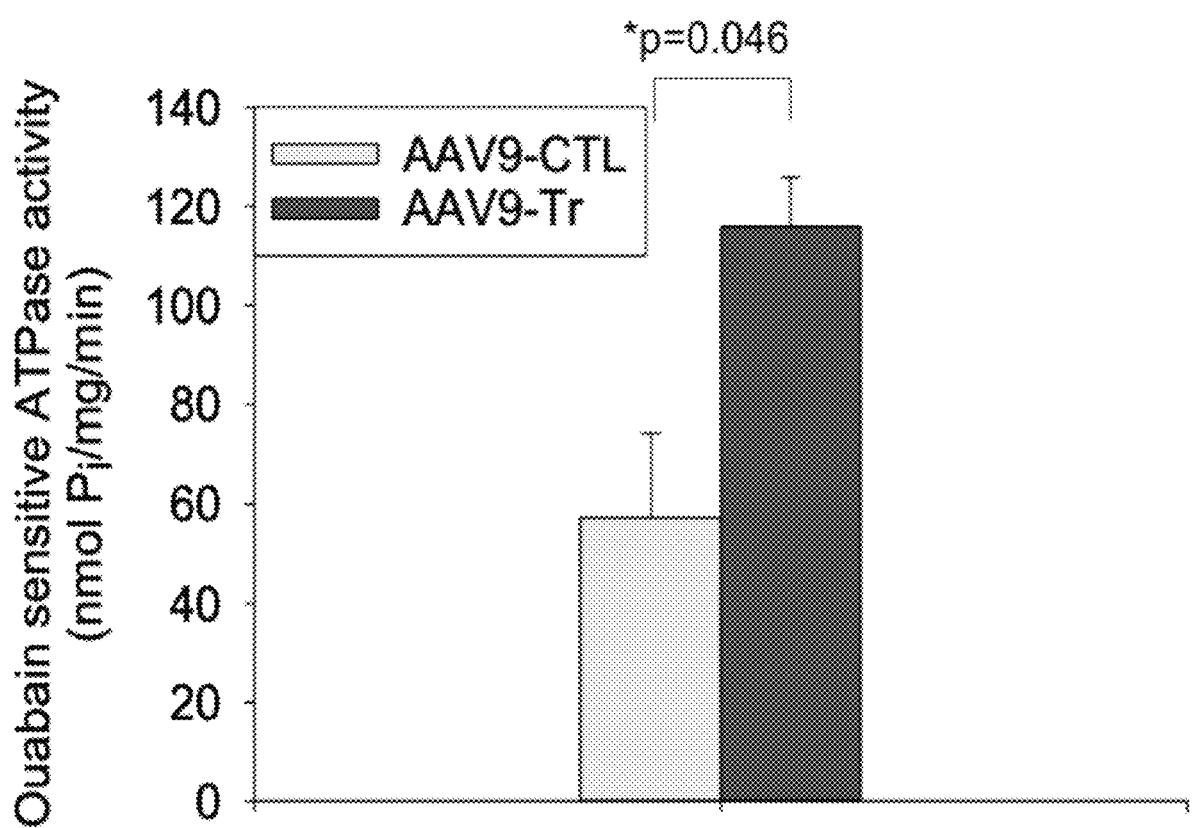
FIG. 5 is a graph showing the effect of unilateral intracerebroventricular (ICV) injection of active vector (AAV9-hSyn-ATP1A3-FLAG-p2a-Cherry-SV40polyA, referred to as AAV9-Tr, dose 5 μL of $4\times10^{13}$ vg/mL) into the lateral ventricle at P10 on ipsilateral hippocampus ouabain-sensitive ATPase activity (nmol Pi/mg protein/min) of P40 WT mice as compared to control vector lacking the transgene (AAV9-CTL, n=3 in each group).

P40 wild-type mice injected unilaterally, at P10, ICV with active vector (AAV9-hSyn-ATP1A3-FLAG-p2a-Cherry-SV40polyA, V=5 µl, $4\times10^{13}$ vg/ml, n=3/group) showed, as compared to control vector (vector lacking the ATP1A3 transgene), that ouabain-sensitive ATPase activity was 102% higher in the ipsilateral hippocampus (FIG. 5, p=0.046 one tailed Student's t-test). In other ipsilateral areas the changes did not achieve statistically significant differences (number of mice was only 3 per group) but areas closer to the hippocampus showed increased ouabain-sensitive ATPase activity as compared to control vector. These were 37% higher in the cerebral cortex, 26% higher in the basal ganglia/thalamus, 16% higher in brainstem and none in the cerebellum (all comparisons p>0.05) after the above unilateral ICV injection.

Example 3: Transduction after Unilateral Intrahippocampal and Intracerebroventricular Injections Assessed by mCherry Expression Intrahippocampal injections of $4\times10^{10}$ vg (V=5 µL of $4\times10^{13}$ vg/mL of AAV9-Syn-ATP1A3-p2a-mCherry-SV40polyA (AAV9-ATP1A3) in Mashl$^{+/-}$ and WT-littermates injected at ages P0-P10 and in adult mice were performed in 24 mice. These were sacrificed one month later.

Figure 6A:
FIGS. 6A-6B are epifluorescence images showing AAV9-hSyn-ATP1A3-FLAG-p2a-Cherry-SV40polyA transduction in adult Mashl$^{+/-}$ mice 10 days after intrahippocampal injection of $20\times10^{10}$ vg (V=5 μL of $4\times10^{13}$ vg/mL) mouse.
Figure 6B:
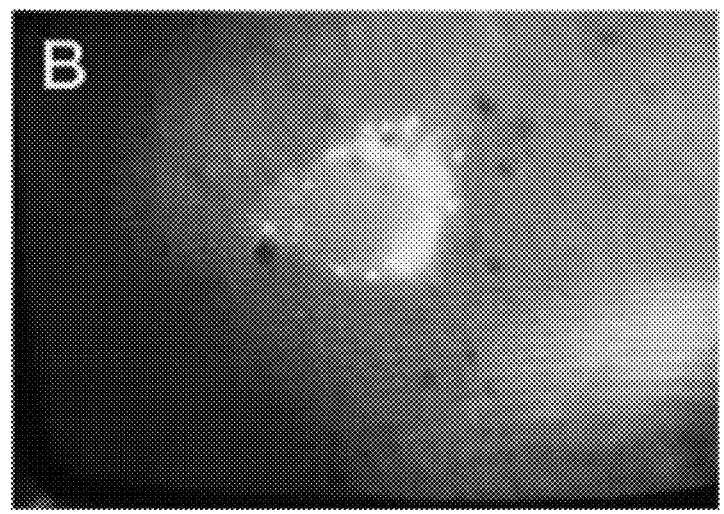

The results demonstrated excellent transduction efficacy of active viral vector in all ages as detected by the mCherry signal and as illustrated in the hippocampus of an adult WT mouse (FIGS. 6A-6B). Consistently, the percent of neurons expressing mCherry in CA1 was >90%, and in CA3 ~70%. Expression was robust in both the pyramidal cells and in interneurons.

Figure 7A:
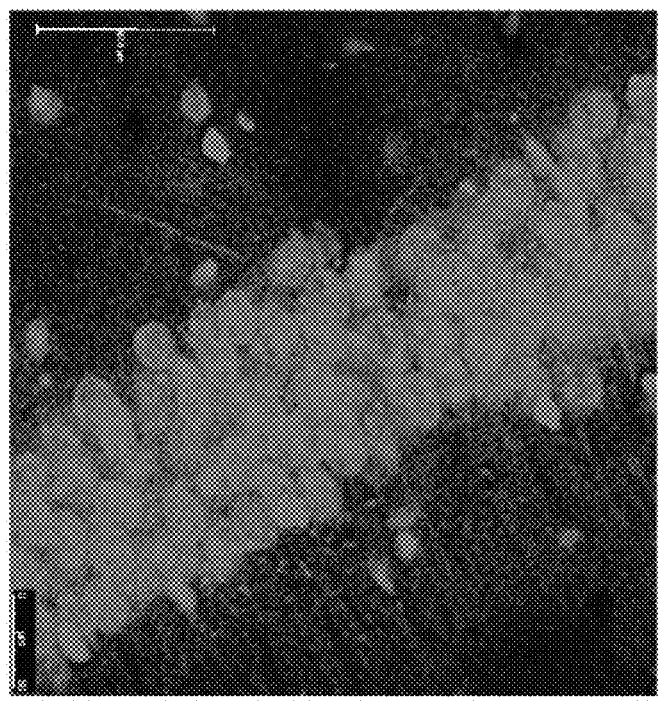
FIGS. 7A-7B are confocal images showing mCherry expression of AAV9-ATP1A3-mCherry-FLAG ($4\times10^{13}$ vg/mL; V=5 μL) after 4 weeks of ICV injection in the right lateral ventricle at P10 in accordance with one embodiment of the present disclosure.
Figure 7B:
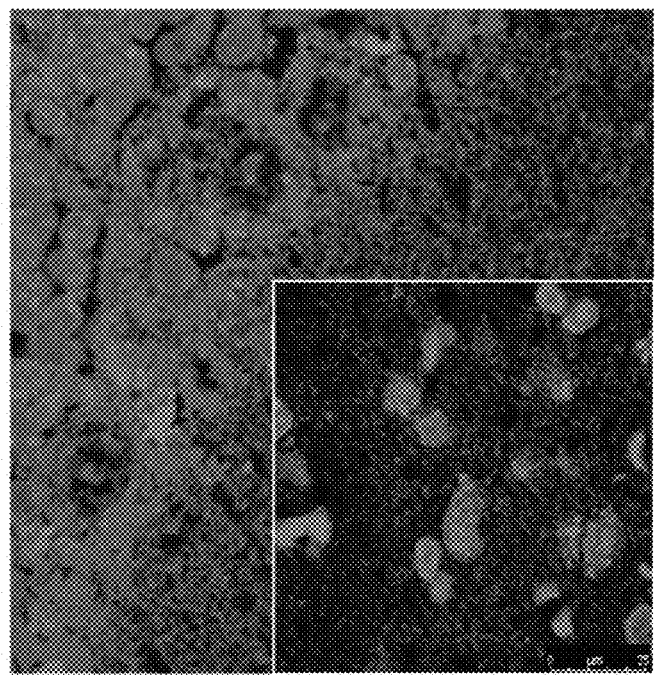

In addition, unilateral intracerebroventricular injection (ICV) of AAV9-ATP1A3 ($4\times10^{13}$ vg/mL; V=5 µl) in ~P10 mice showed at P40 excellent expression of mCherry seen in the cytoplasm in various brain regions including hippocampus, basal ganglia, thalamus, cortex and even in the, relatively distant, cerebellum (FIGS. 7A-7B).

Example 4: Restoring Motor Performance on Balance Beam Test in Mutant Mice

Figure 8:
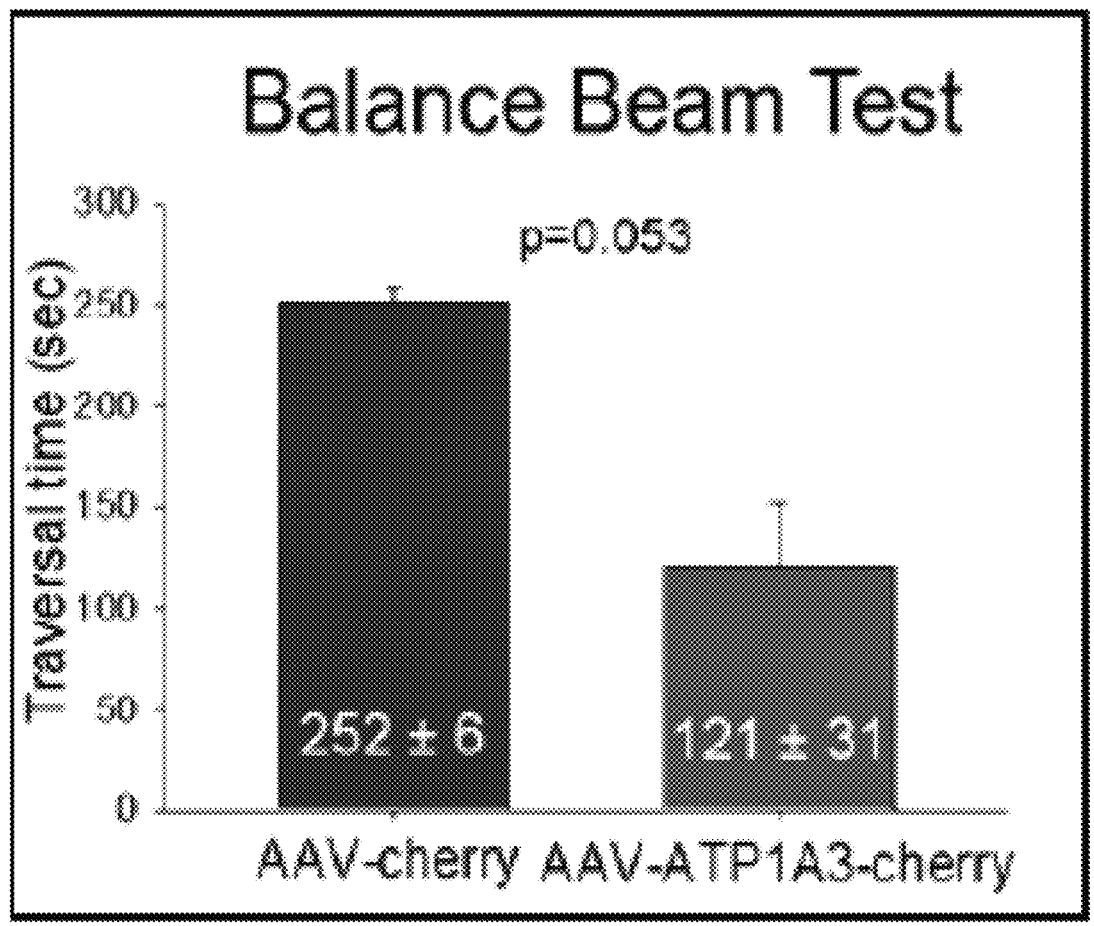
FIG. 8 is a graph showing the effect of AAV-ATP1A3-Cherry and AAV-cherry on beam test in Mashl$^{+/-}$ mice. Unilateral intrahippocampal injection of $20\times10^{10}$ vg (volume 5 μl) of active vector into the hippocampus was performed on 2-3 month old mice. Test performed 3 weeks post-injection.

To determine whether unilateral intrahippocampal AAV9-Syn-ATP1A3-p2a-Cherry-SV40polyA could restore motor performance in mutant mice, a balance beam test was performed. Adult mutants Mashl$^{+/-}$ mice (2-3 month old mice) were treated with intrahippocampal AAV9-Syn-ATP1A3-p2a-Cherry-SV40polyA (20 $10^{10}$ vg in 5 µl of $4\times10^{13}$, n=6 mice) and tested 21 days post-injection. Mashl$^{+/-}$ mice treated with AAV-Syn-ATP1A3-p2a-Cherry-SV40polyA (n=3) had better performance (i.e., they crossed the beam faster) than Mashl$^{+/-}$ mice treated with control vector AAV-cherry (n=3 per group, p=0.053, Student's t-test one tailed) (FIG. 8). Injection of AAVs was performed on 2-3 month old mice.

Figure 9A:
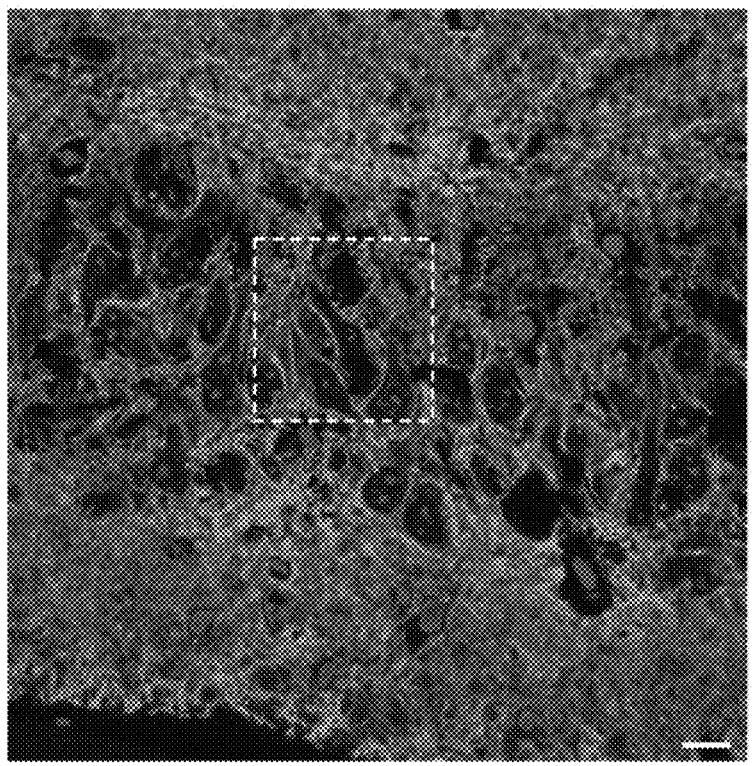
FIGS. 9A-9F are confocal images showing vector transduction as assessed by FLAG-tag green fluorescence, mCherry red fluorescence and DAPI (stains nuclei) in blue. Injections were performed at P10 with sacrifice at P40.
Figure 9B:
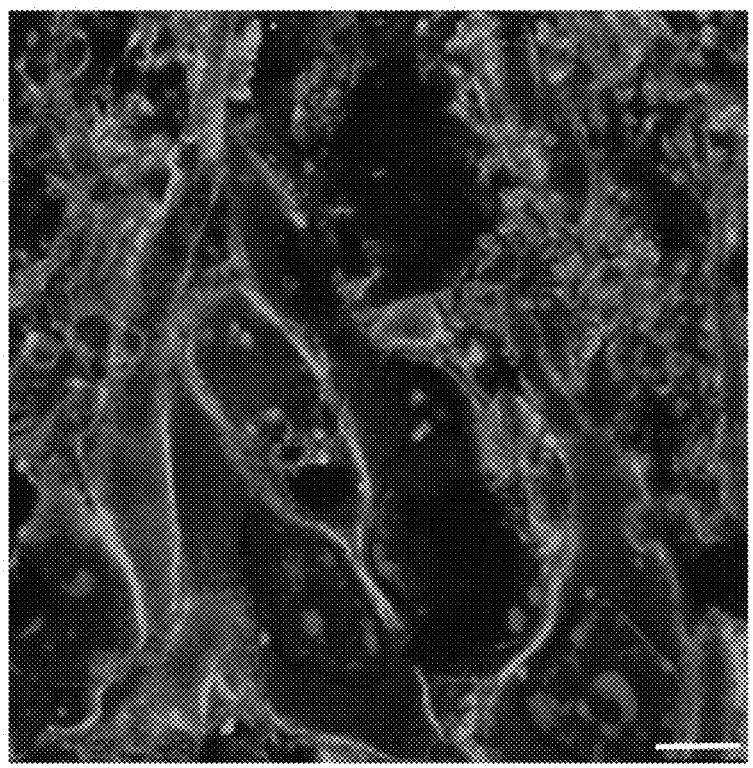
Figure 9C:
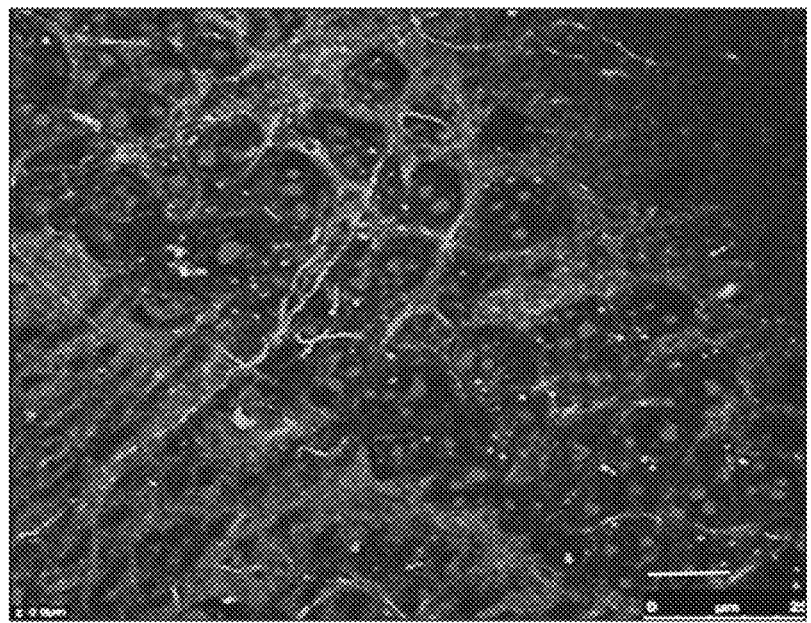
Figure 9D:
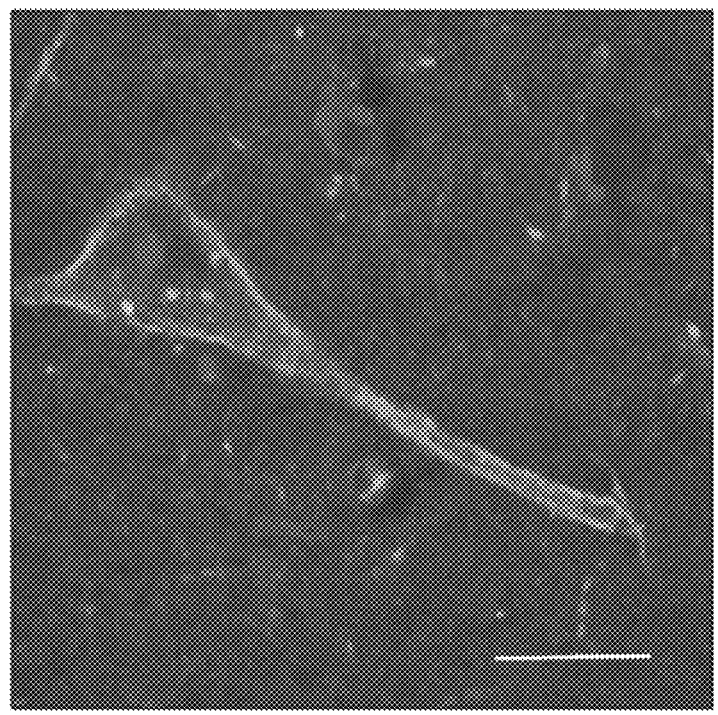
Figure 9E:
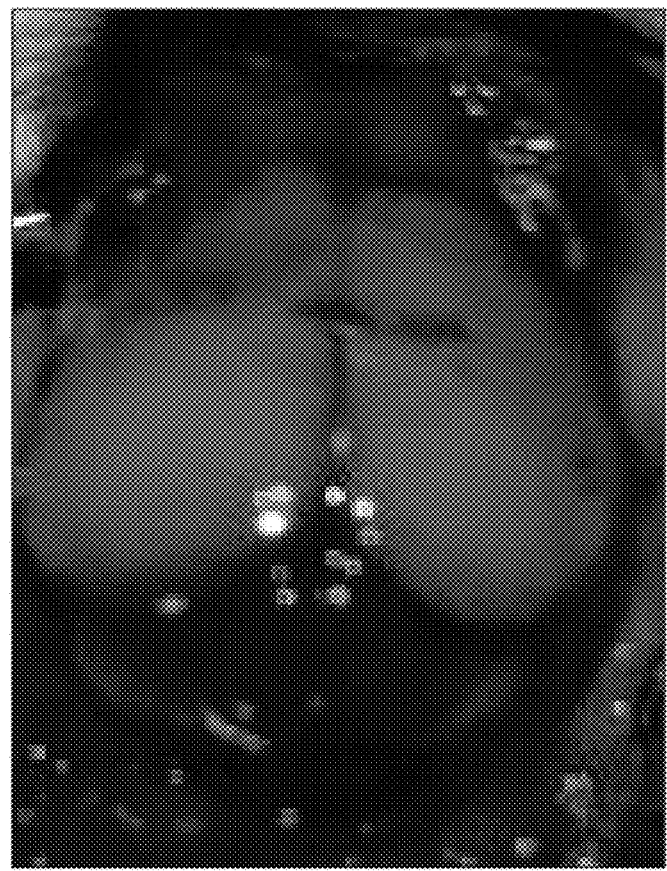
Figure 9F:
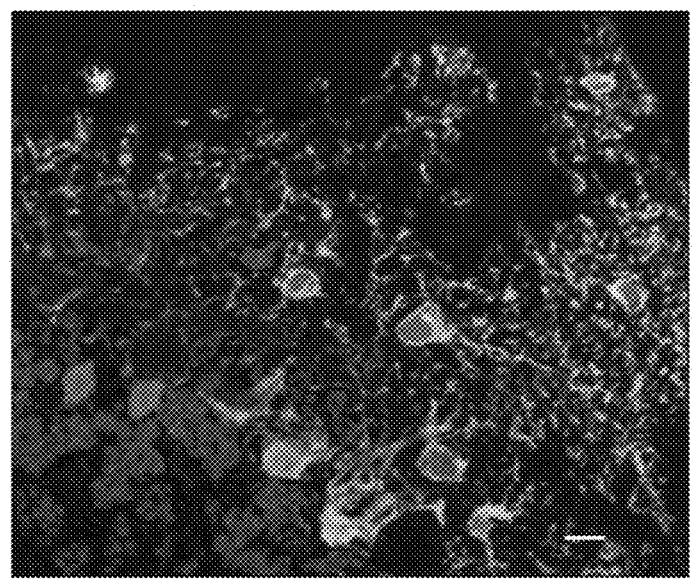

Example 5: ICV and Intra-Cisterna Magna (ICM) Injections of AAV9 Active Vector Result in Robust FLAG Reporter Gene Expression in Brain Regions Contiguous to the Injection Sites To determine the extent of reporter gene expression after ICV and ICM injections we performed the following. 1) Unilateral ICV injection of $20\times10^{10}$ vg at P10 with sacrifice of animals at P40 (FIGS. 9A-9D). 2) ICM injection of $15\times10^{10}$ vg at P10 with sacrifice at P40 (FIG. 9F). Incremental dose study of combined ICM and bilateral ICV injections using three doses of the same AAV active vector injected at P10 and sacrificed at P40 (AAV9-hSyn-ATP1A3-FLAG-p2a-Cherry-SV40polyA, 4 WT mice/dose, FIGS. 10A-10H). The three doses studied were $3\times10^{10}$ vg in each site (cisterna magna and the two lateral ventricles, total 9×10$^{10}$ vg/mouse), 6×10$^{10}$ vg in each site (total 18×10$^{10}$ vg/mouse) and 9×10$^{10}$ vg in each site (total 27×10$^{10}$ vg/mouse).

Figure 10A:
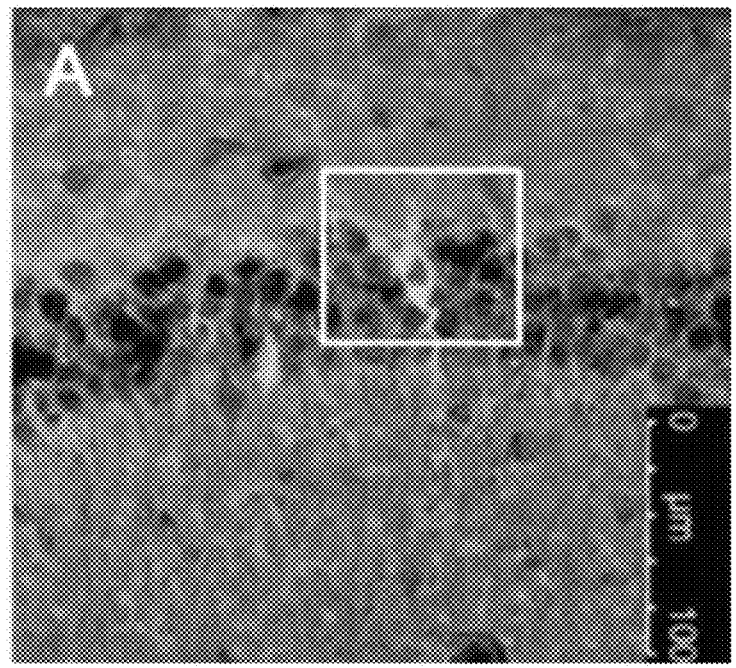
FIGS. 10A-10H show expression of reporter genes at P40 (confocal merged images in all, FLAG, green; mCherry, red; DAPI, staining nuclei as blue): high in hippocampus (A, B) and in cerebellum close to ICM injection site (E). It is lower in cortex (C, D), and very low if any in cerebellum distant from ICM injection site (F), brainstem (G) and thalamus (H) following vector injected ICM and bilateral ICV of $9\times10^{10}$ in each (total $27\times10^{10}$ vg/mouse) at P10.
Figure 10B:
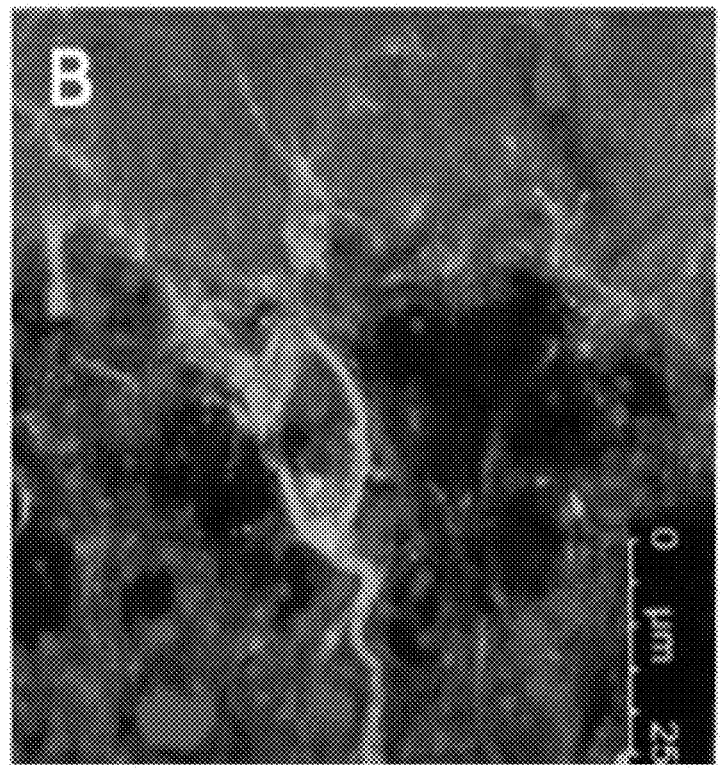
Figure 10C:
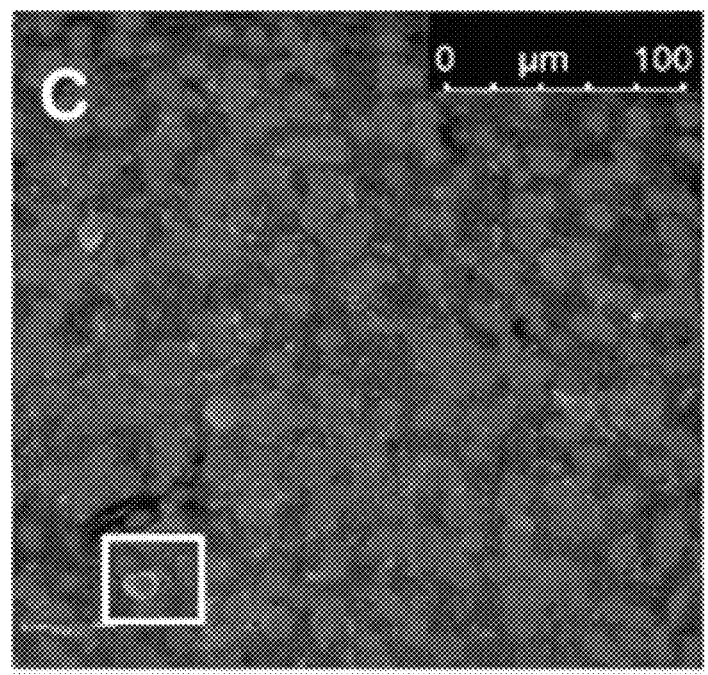
Figure 10D:
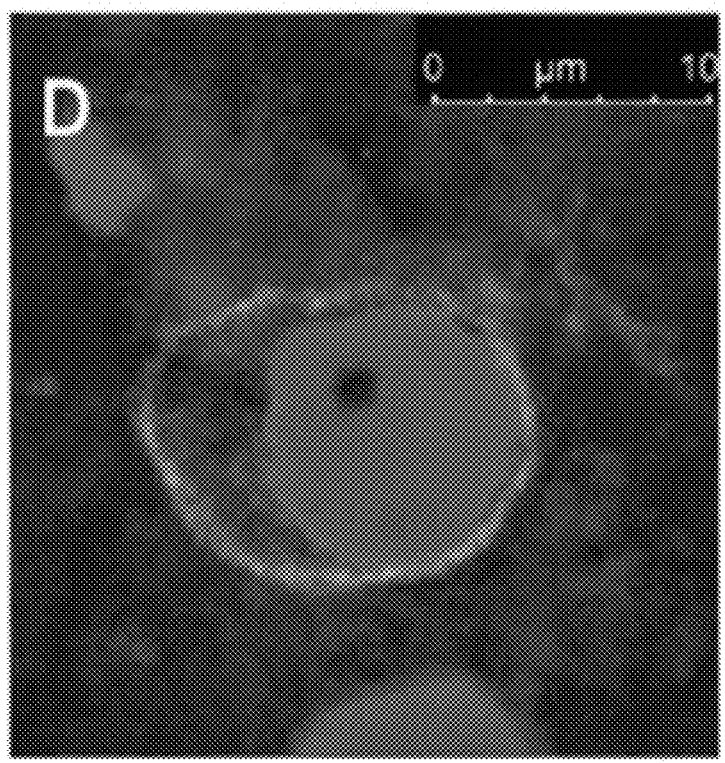
Figure 10E:
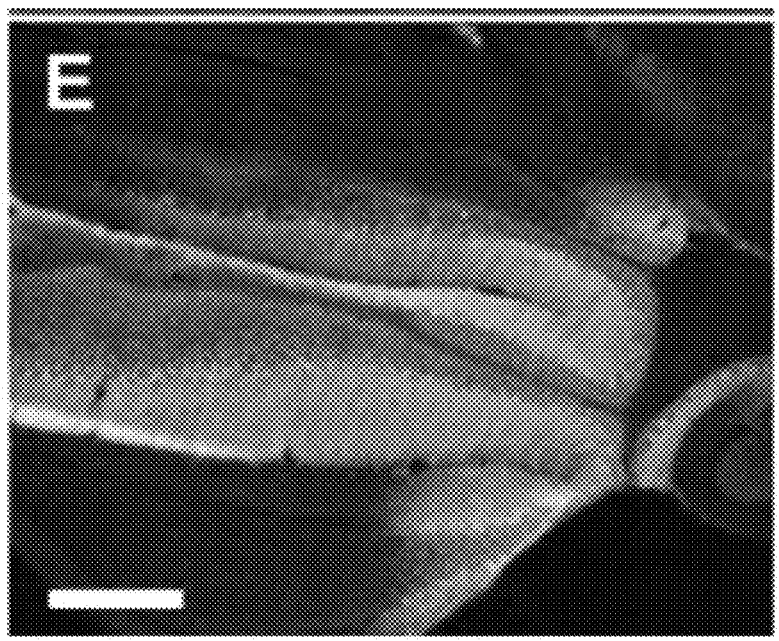
Figure 10F:
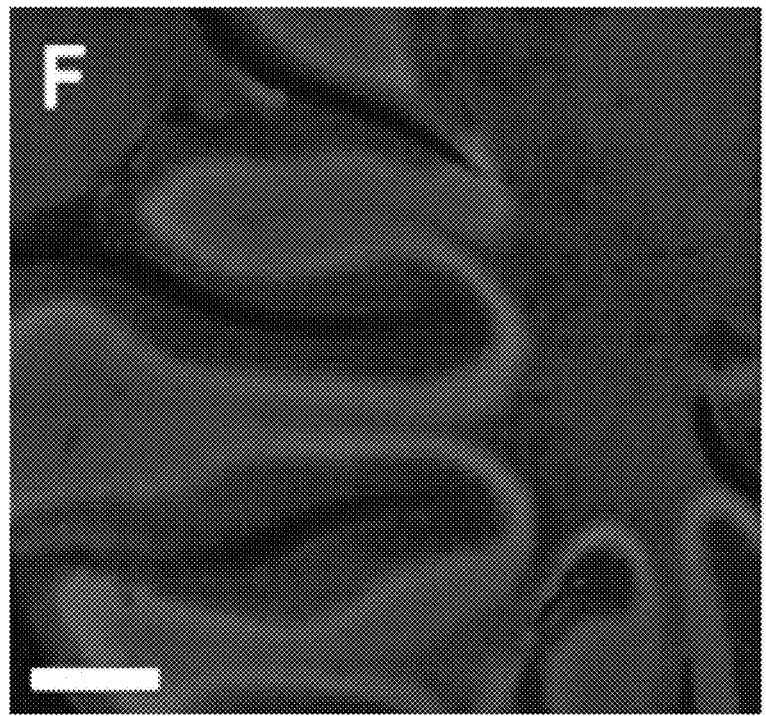
Figure 10G:
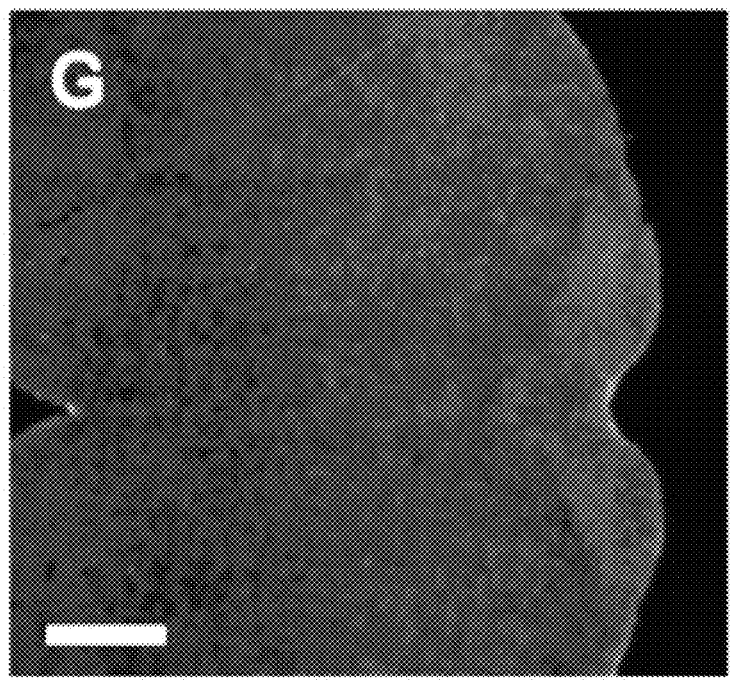
Figure 10H:
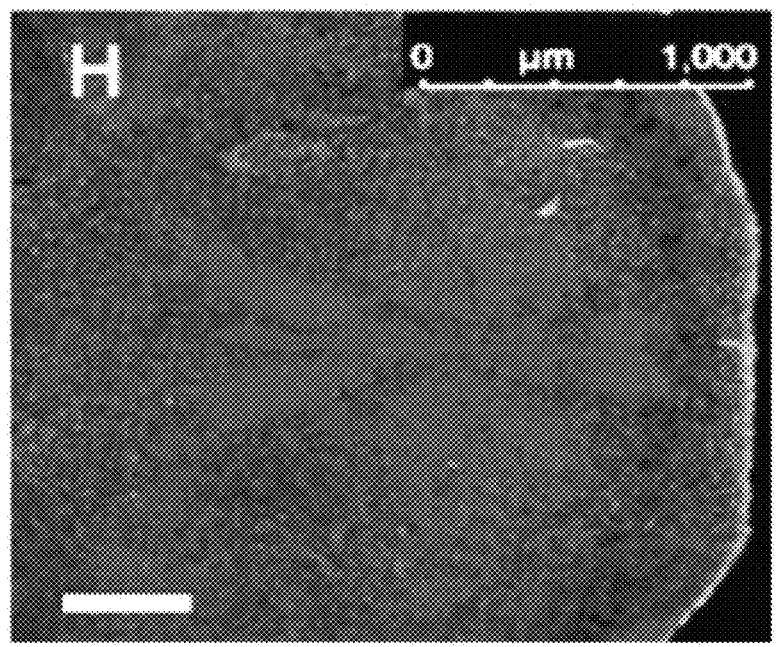

Robust transgene expression was observed with the higher doses (FIGS. 9A-9D, 9F and FIGS. 10A-10H) but not with the lower two doses of the incremental dose study. Two reporter genes, FLAG after the 3' terminal of ATP1A3 DNA followed by mCherry with a cleavage site in between them, were used to assess transgene expression. Specifically, the hippocampus showed FLAG expression nearly 100% of cells in the CA3 and CA1 hippocampal regions on the side of the ICV injections whether after a unilateral or bilateral ICV injections (FIGS. 9A-9D and FIGS. 10A-10B). After unilateral ICV injections, there was minimal expression on the contralateral side. With combined ICM and bilateral ICV injections cortex and cerebellum showed expression in about 10% of total cells with much higher percentages in areas close to the injection sites: almost all the cells in those regions showed robust expression (FIGS. 10A-10E) while more distant areas showed very low if any expression. Deep brain structures including basal ganglia, thalamus, and brainstem also showed hardly any expression (FIGS. 10F-10H).

In these experiments, mCherry was detected in the cytoplasm since it is cleaved from the ATP1A3-FLAG, whereas ATP1A3-FLAG fusion protein was detected in the cell membrane the functional locale of the pump (FIGS. 9A-9F and FIGS. 10A-10H). This indicates that the ATP1A3 transgene is not only expressed but also that the ATP1A3 protein is transported to its functional locale, the cell membrane. In the active vector, since FLAG coding DNA sequence is at the 3' end of the ATP1A3 coding sequence, it is expected to be transcribed only after ATP1A3 coding sequence is transcribed. Thus, the demonstration of a positive signal for FLAG indicates the expression and transcription of exogenous ATP1A3 through the active vector.

Whether administration of the entire high dose unilaterally ICV would increase transduction beyond the immediately contiguous areas using two doses one almost triple the other was studied. The two doses were: 7.5×10$^{10}$ vg unilaterally ICV and 20×10$^{10}$ vg unilaterally ICV. With both, nearly 100% of hippocampal neurons expressed FLAG on the side ipsilateral to the injection site with about 10% in cortex and essentially no expression in other areas. These data indicated that dosing regimen providing the highest level of transgene expression without using needlessly additional vector was about 7.5×10$^{10}$ vg per injection site and that ICM and bilateral ICV injections are needed. This justified the use of the combination ICM and bilateral ICV dose of 7.5×10$^{10}$ in each site for a total of 22.5×10$^{10}$ vg/animal in studies looking at survival and behavior.

Example 6: Combined ICV and ICM Active Vector Injections Result in Improvement in Mashl$^{+/-}$ Phenotype The effects of active vector and control vector administered via ICM and bilateral ICV (22.5×10$^{10}$ vg/animal, 7.5×10$^{10}$ in each site) injections at P10 were compared at P40. The studied groups were wild type untreated (WT Naïve, n=10), wild type control (WT-CTL, n=10), wild type treatment (WT-Tr, n=4), mutant control (Het-CTL, n=10) and mutant treatment (Het-Tr, n=9) groups.

Figure 11:
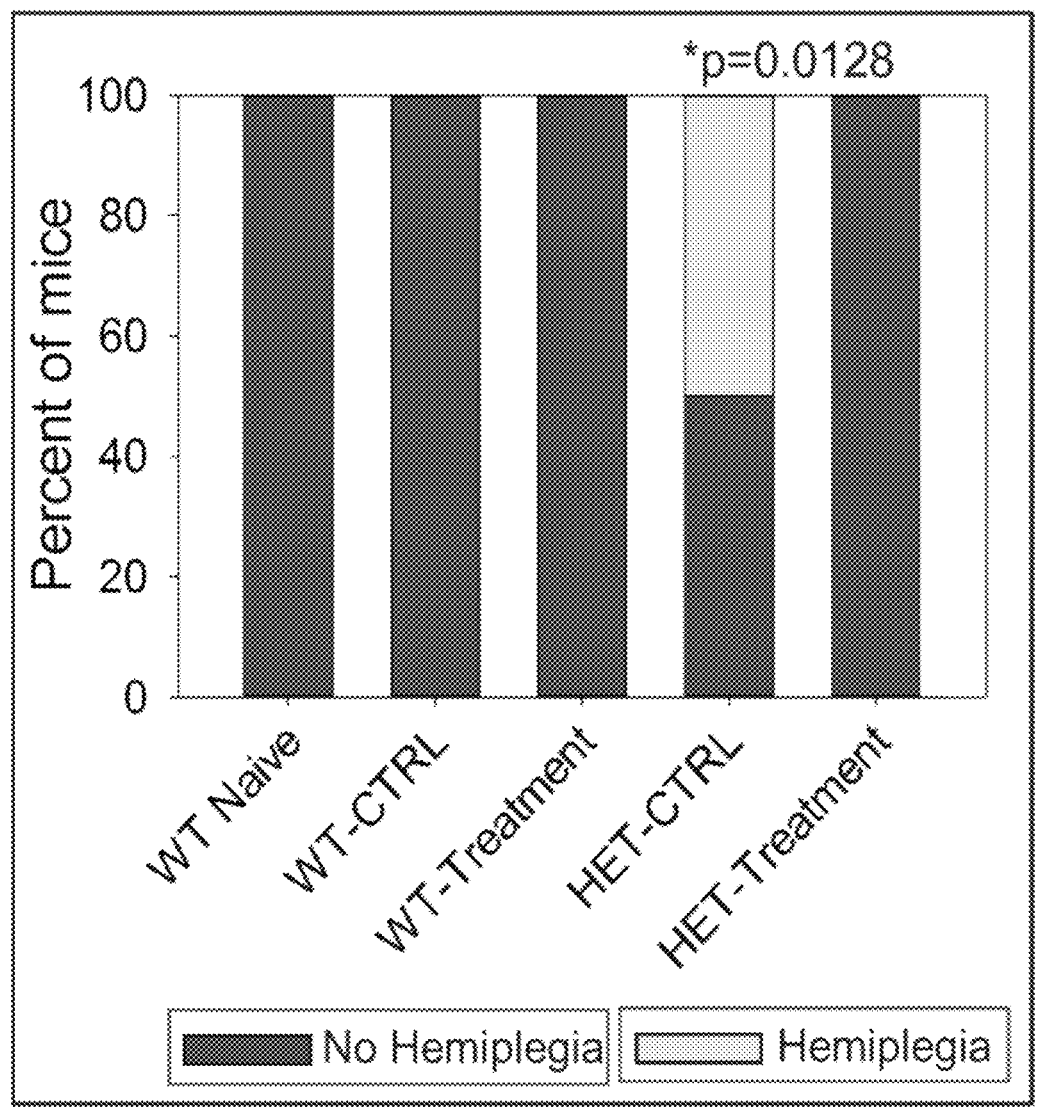
FIG. 11 is a graph showing a comparison of cold water induced hemiplegia among the following groups of mice treated via ICM and ICV injections: WT uninjected mice (naïve), WT mice treated with control vector (WT CTRL), WT treated with active vector (WT Treatment), Mashl$^{+/-}$ mice treated with control vector (Het CTRL), and Mashl$^{+/-}$ treated with active vector (Het Treatment). Mice were injected ICM and bilateral ICV in each lateral ventricle at P10 (AAV9-hSyn-ATP1A3-FLAG-p2a-Cherry-SV40polyA $22.5\times10^{10}$ vg/animal, or with control vector without ATP1A3 transgene, $7.5\times10^{10}$ vg in each site. Comparison groups were WT naïve (n=10), WT-CTRL group (n=10), WT-treatment (n=4), Het-CTRL (n=10), Het-treatment (n=9). These were compared at P40.
Figure 12:
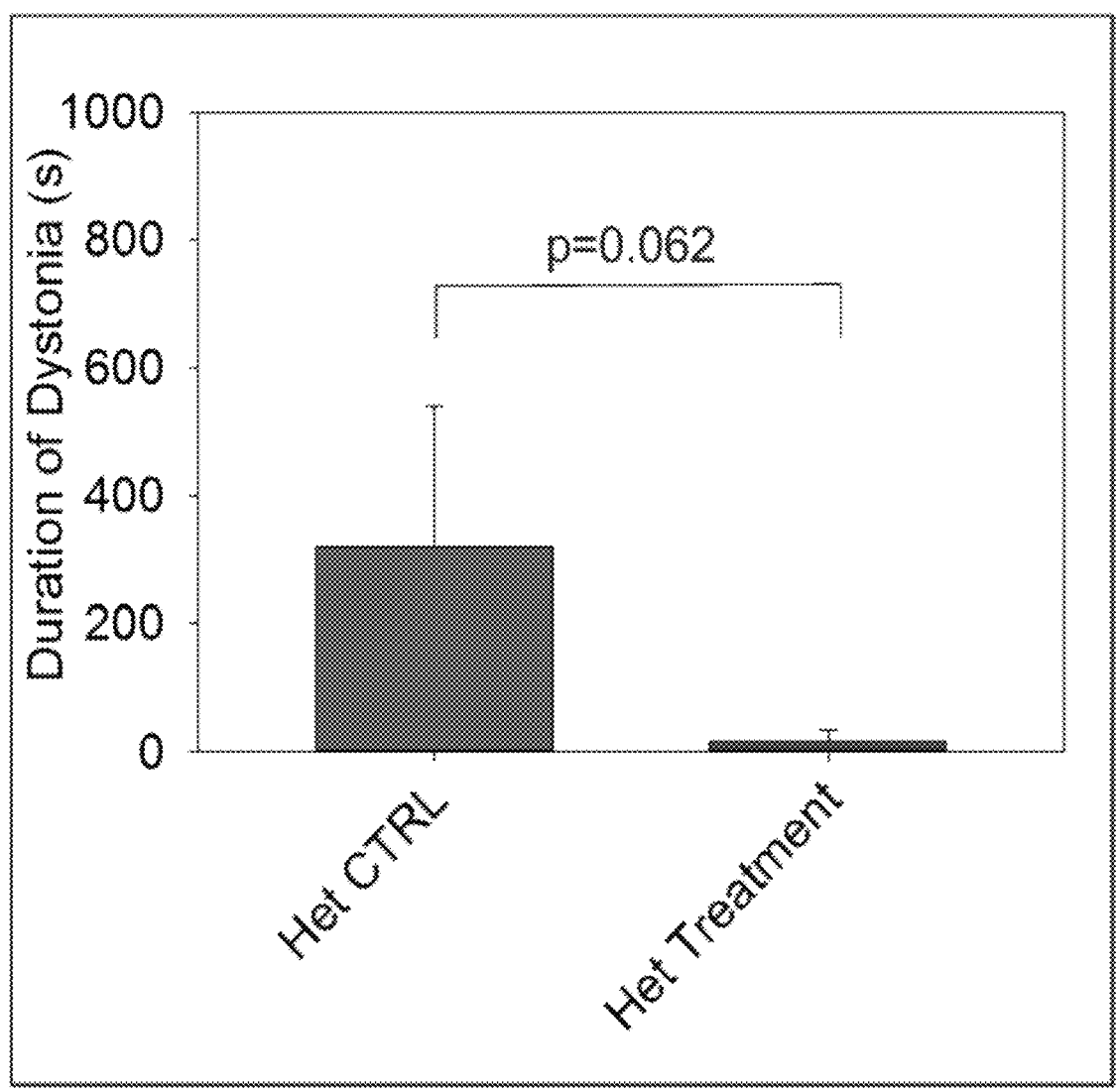
FIG. 12 is a graph showing a comparison of the duration of cold water induced dystonia between Mashl$^{+/-}$ mice treated with control vector (Het CTRL) and Mashl$^{+/-}$ treated with active vector via ICM and ICV injection (Het Treatment). Mice were injected ICM and bilateral ICV in each lateral ventricle at P10 (AAV9-hSyn-ATP1A3-FLAG-p2a-Cherry-SV40polyA $22.5\times0^{10}$ vg/animal, or with control vector without ATP1A3 transgene, $7.5\times10^{10}$ vg in each site, as per [0045]) and were compared at P40.
Figure 13:
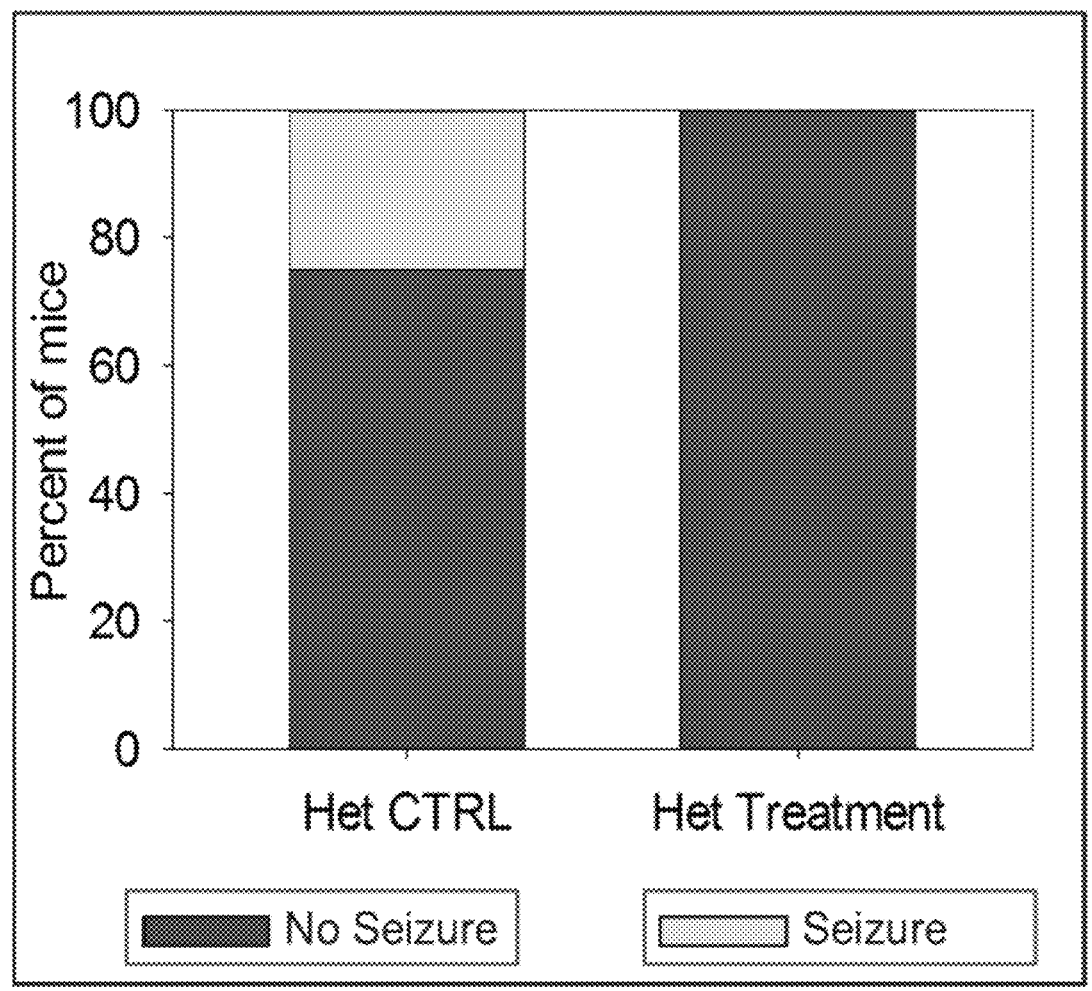
FIG. 13 is a graph showing a comparison of cold-water induced seizures between Mashl$^{+/-}$ mice treated with control vector (Het CTRL) Mashl$^{+/-}$ treated with active vector via ICM and ICV injection (Het Treatment). Mice were injected ICM and bilateral ICV in each lateral ventricle at P10 and sacrificed at P40 (AAV9-hSyn-ATP1A3-FLAG-p2a-Cherry-SV40-polyA $22.5\times0^{10}$ vg/animal, $7.5\times10^{10}$ vg in each site, as per [0045] and were compared at P40.

It was found that Mashl$^{+/-}$ mice treated with the active vector experienced significantly decreased occurrence of hemiplegia spells (FIG. 11, p=0.0128, Het control n=4, Het treatment n=6) and a trend for shorter duration of dystonia spells (FIG. 12) induced by the cold-water immersion test (p=0.00359 for comparison of all groups using one way ANOVA and 0.062 for comparison of Het-treatment and Het-control groups using one tailed Student's t-test, Het control n=4, Het treatment n=6). None of the mice of the three WT groups had dystonia so these groups are not shown in FIG. 12. Additionally, none of the mice receiving active vector had cold-water induced epileptic seizures while 25% of those receiving control vector had seizure (FIG. 13 Het control n=4, Het treatment n=6). The latter comparison did not achieve statistical significance (p>0.05), but the first two did as illustrated by the p values above.

Figure 14:
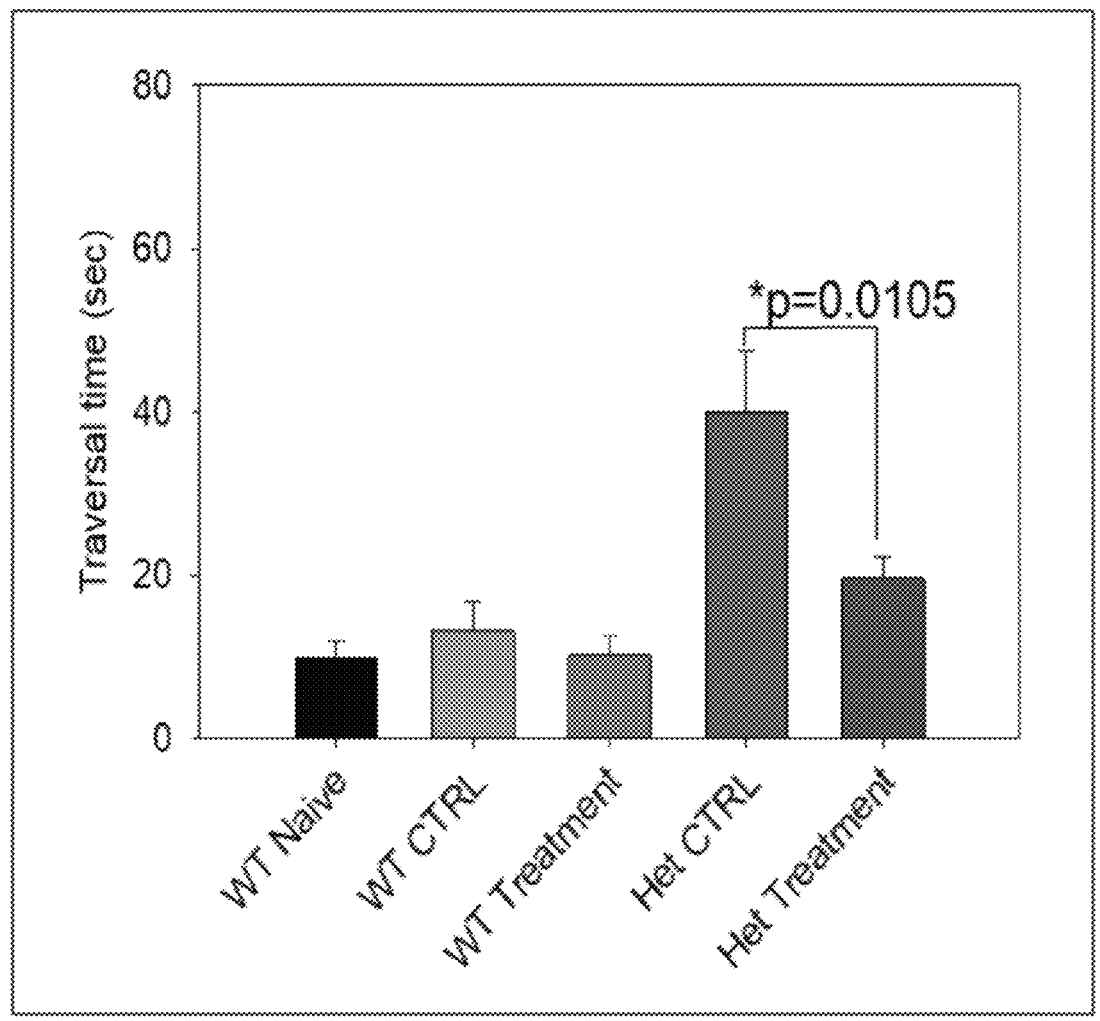
FIG. 14 is a graph showing a comparison of the time to cross a balance beam among the following groups of mice treated via ICM and ICV injections: WT uninjected mice (naïve), WT mice treated with control vector (WT CTRL), WT treated with active vector (WT Treatment), Mashl$^{+/-}$ mice treated with control vector (Het CTRL), and Mashl$^{+/-}$ treated with active vector (Het Treatment). Mice were injected ICM and bilateral ICV in each lateral ventricle at P10 (AAV9-hSyn-ATP1A3-FLAG-p2a-Cherry-SV40polyA $22.5\times0^{10}$ vg/animal, or with control vector without ATP1A3 transgene, $7.5\times10^{10}$ vg in each site, as per [0045] and were compared at P40.

Significant improvements on the 8 mm balance beam test were also observed. In particular, mutant Mashl$^{+/-}$ mice receiving active vector had significantly shorter times in crossing the beam (FIG. 14, p≤0.001 for comparisons among the groups using ANOVA, p=0.0105 two tailed Student's t-test for comparison between the Het-Tr and Het-CTRL groups, WT naïve n=6, WT-CTRL n=10, WT-Tr n=4, Het-CTRL n=6, Het-Tr n=9).

Figure 15:
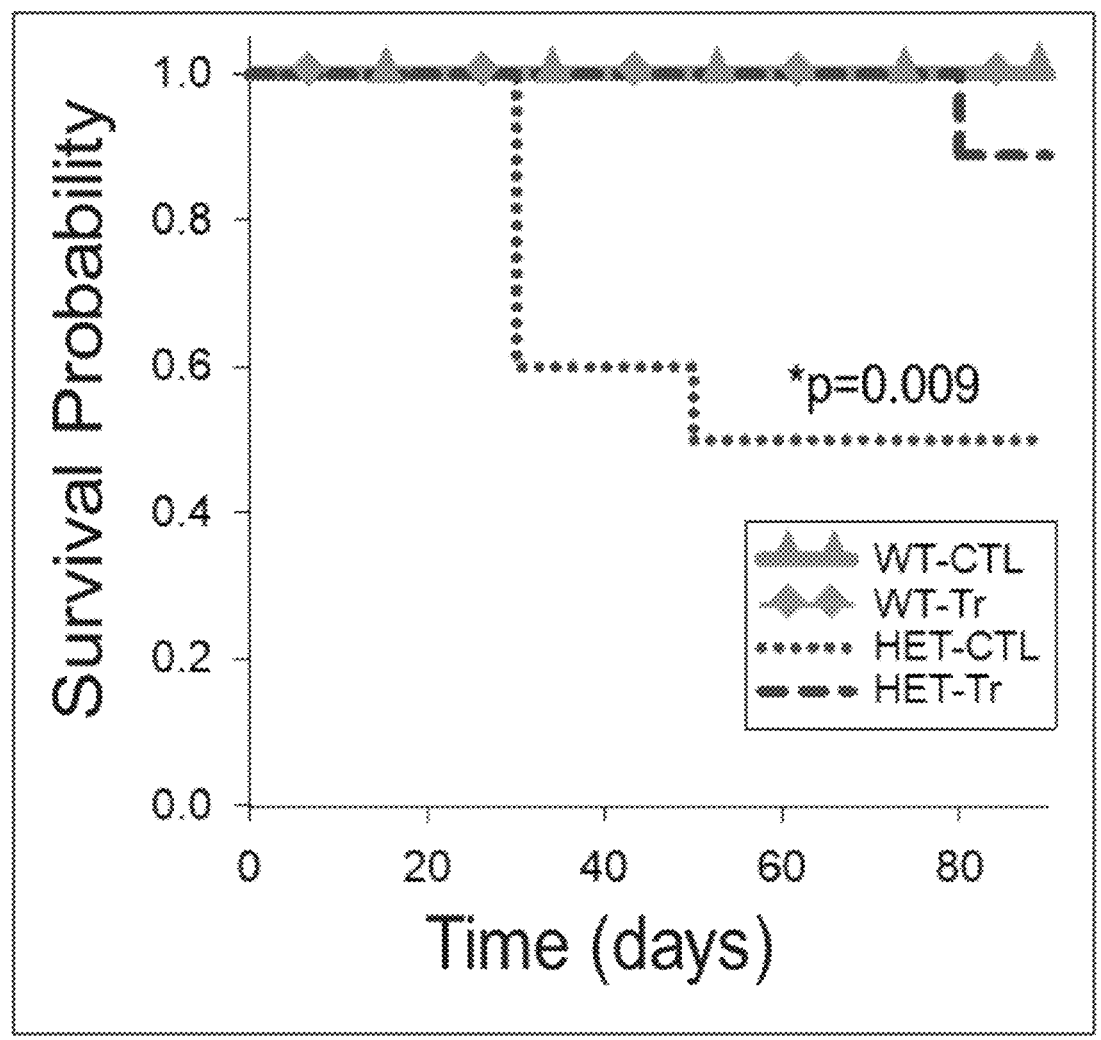
FIG. 15 is a graph showing the Kaplan-Meier survival curve comparing the treatment and control groups demonstrating a major positive effect on survival in mice injected with active vector at P10 with the above ICM and bilateral ICV active and control vector injection regimen described in [0045] above (p=0.009). The groups were WT mice treated with control vector (WT CTRL), WT treated with active vector (WT Treatment), Mashl$^{+/-}$ mice treated with control vector (Het CTRL), and Mashl$^{+/-}$ treated with active vector (Het Treatment). Mice were injected ICM and bilateral ICV in each lateral ventricle at P10 (AAV9-hSyn-ATP1A3-FLAG-p2a-Cherry-SV40polyA $22.5\times0^{10}$ vg/animal, or with control vector without ATP1A3 transgene, 7.5×10$^{10}$ vg in each site, [as per 0045]) and were followed into adulthood through P90.
Figure 16:
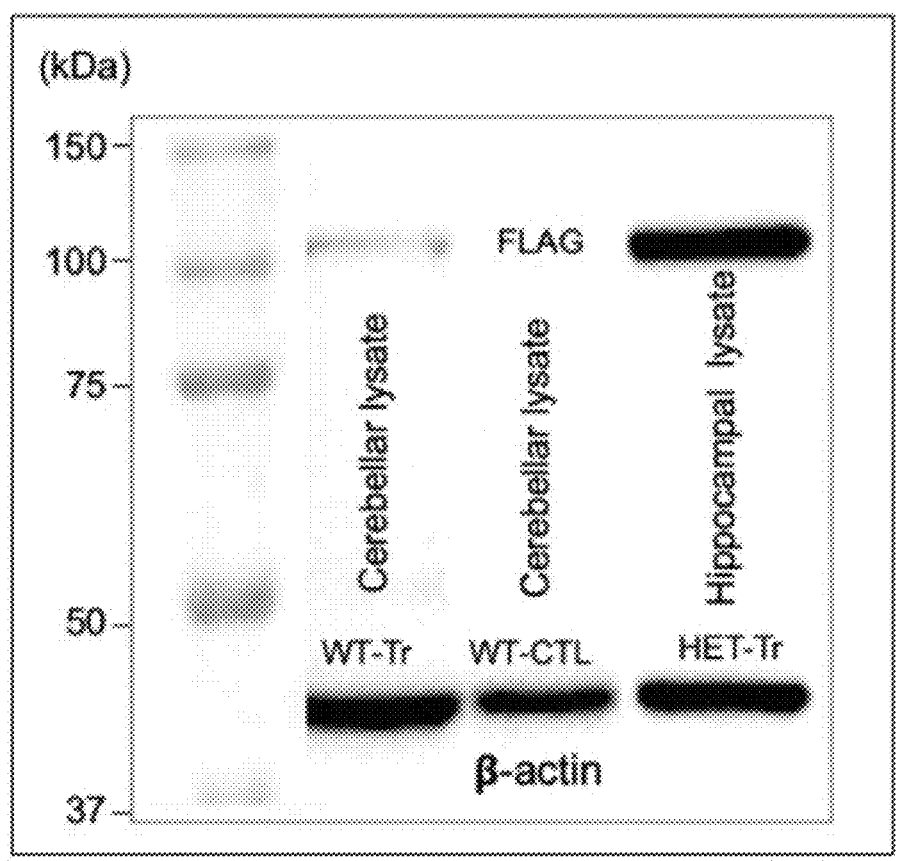
FIG. 16 is Western blot of 3 mice WT-Tr (cerebellum), WT-CTL (cerebellum) and HET-Tr (hippocampus). The FLAG band is the top band and β actin is the bottom band. Mice were injected ICM and bilateral ICV in each lateral ventricle at P10 (AAV9-hSyn-ATP1A3-FLAG-p2a-Cherry-SV40polyA 22.5×0$^{10}$ vg/animal, or with control vector without ATP1A3 transgene, 7.5×10$^{10}$ vg in each site, 9-10/group) and were sacrificed for Western blot after P90.
Figure 17:
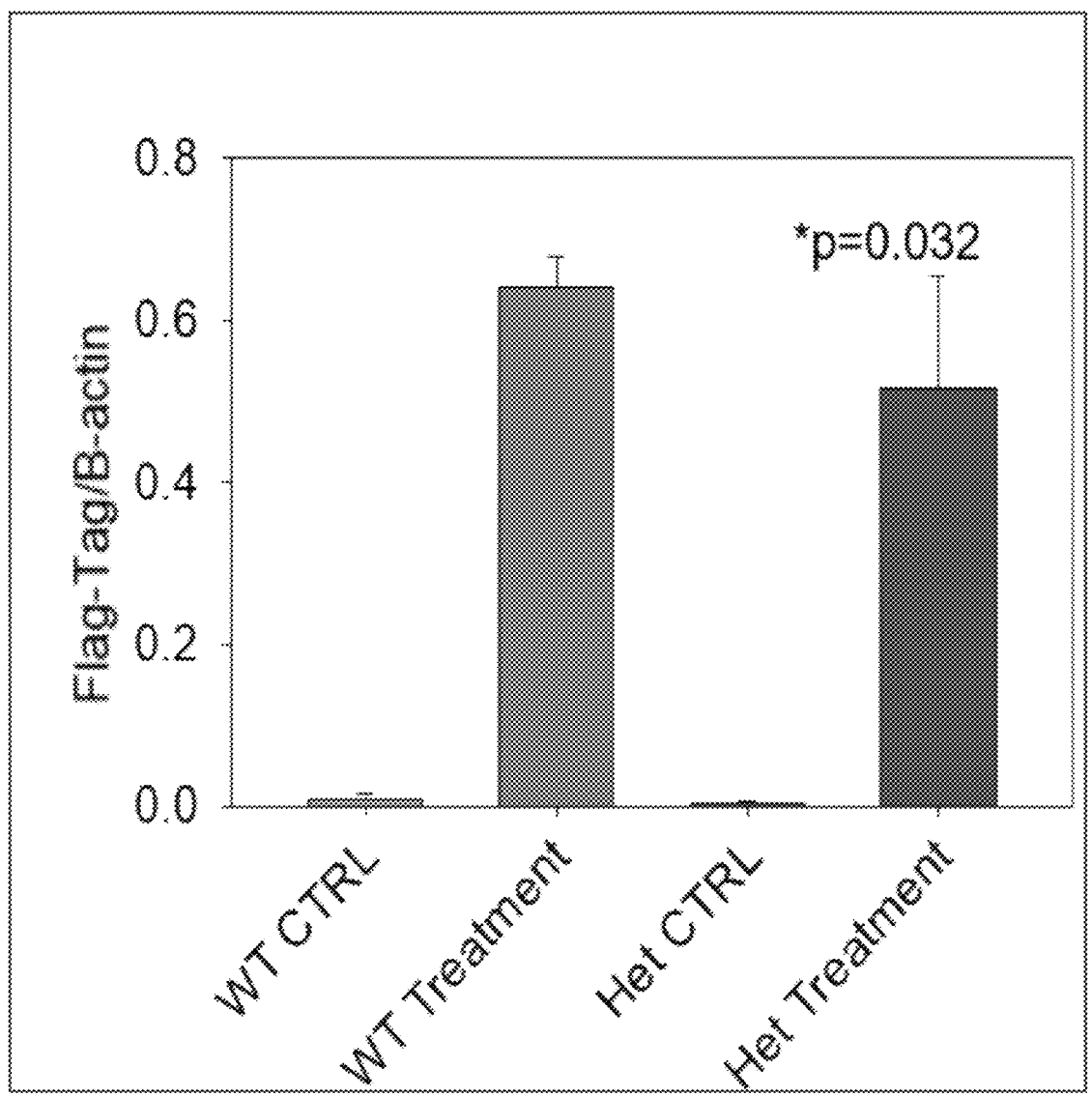
FIG. 17 is a graph showing comparison of Western blot densitometry results of the treatment and control groups in the hippocampus with combined ICM and bilateral ICV injections at P10 and sacrificed after P90 (AAV9-hSyn-ATP1A3-FLAG-p2a-Cherry-SV40polyA 22.5×0$^{10}$ vg/animal, or with control vector without ATP1A3 transgene, 7.5×10$^{10}$ vg in each site). WT CTRL, n=2 mice; WT treated with active vector (WT Treatment), n=2 mice; Mashl$^{+/-}$ CTRL (HeT CTRL), n=2 mice; Mashl$^{+/-}$ treated with active vector (Het Treatment), n=3 mice.

Example 7: Combined ICV and ICM Active Vector Injections Result in Long Term Improved Survival When the above groups of mice were followed into adulthood through P90, the group treated with the active vector showed much better and statistically significant (p=0.009) survival as compared to the mutant group injected with the control vector (HET-CTL) (FIG. 15). When animals were sacrificed after P90 Western blot showed expression of the FLAG antibody in both hippocampus and cerebellum in mice injected with active vector as illustrated by sample Western blots (FIG. 16) and by comparative densitometry (FIG. 17, p=0.032). The Western blots shown in FIG. 17 illustrates that there is continued expression of the FLAG transgene into adulthood at P90 in both cerebellum and hippocampus. The FLAG band intensity was much stronger in hippocampal lysate than in the cerebellar lysates (FIG. 16). The graph shown in FIG. 17 (WT-CTRL n=2, WT-Tr n=2, Het-CTRL n=2, Het-Tr n=3, p=0.032 for comparison of control and the treatment groups using one way ANOVA with post-hoc Student-Newman-Keuls method) illustrates the continued expression of the FLAG transgene into adulthood at P90 in the WT and Het treatment groups.

Example 8: AAV-Mediated Gene Therapy of Alternating Hemiplegia of Childhood (AHC) in Humans Examples 1-8 demonstrate efficacy of AAV-mediated gene therapy in Mashl$^{+/-}$ mice, which contains the D801N mutation, the most commonly found mutation in human AHC patients. These results indicate that AAV-mediated gene therapy with the ATP1A3 transgene is a therapeutic approach to treating humans with ATP1A3-mediated diseases, including AHC.

To demonstrate efficacy and safety of this AAV-mediated gene therapy approach in humans, the following steps will be taken.

1. Optimize the vector, dose and delivery route.
2. Further optimize dosing regimens and initiate toxicity studies.
3. Initiate human study plans. Duke is the leading center in the International AHC consortium with over 100 patients in the AHC program database.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

No admission is made that any reference, including any non-patent or patent document cited in this specification, constitutes prior art. In particular, it will be understood that, unless otherwise stated, reference to any document herein does not constitute an admission that any of these documents forms part of the common general knowledge in the art in the United States or in any other country. Any discussion of the references states what their authors assert, and the applicant reserves the right to challenge the accuracy and pertinence of any of the documents cited herein. All references cited herein are fully incorporated by reference, unless explicitly indicated otherwise.

The present disclosure shall control in the event there are any disparities between any definitions and/or description found in the cited references.

The invention claimed is:

1. An isolated nucleic acid molecule, comprising from 5' to 3':
   a first inverted terminal repeat sequence,
   a human synapsin promoter sequence operably linked to a nucleic acid sequence encoding ATP1A3, wherein the nucleic acid sequence encoding ATP1A3 has at least 90% identity to the sequence set forth in SEQ ID NO:07, and
   a second inverted terminal repeat sequence.

2. The isolated nucleic acid molecule of claim 1, wherein the ATP1A3 comprises an amino acid sequence having at least 90% identity to SEQ ID NO:06.

3. The isolated nucleic acid molecule of claim 2, wherein the ATP1A3 comprises the amino acid sequence of SEQ ID NO:06.

4. The isolated nucleic acid molecule of claim 1, wherein the nucleic acid sequence encoding the ATP1A3 comprises the sequence set forth in SEQ ID NO:07.

5. The isolated nucleic acid molecule of claim 1, wherein the nucleic acid sequence encoding the ATP1A3 is codon-optimized to reduce CpG methylation sites and for mammalian expression.

6. The isolated nucleic acid molecule of claim 1, wherein the human synapsin promoter sequence comprises the nucleic acid sequence set forth in SEQ ID NO:05.

7. The isolated nucleic acid molecule of claim 1, wherein the human synapsin promoter sequence comprises the nucleic acid sequence set forth in SEQ ID NO:09.

8. The isolated nucleic acid molecule of claim 1, further comprising a bovine growth hormone polyadenylation signal (BGHpA).

9. The isolated nucleic acid molecule of claim 1, comprising a nucleic acid sequence having at least 90% identity to the sequence set forth in SEQ ID NO:20.

10. The isolated nucleic acid molecule of claim 9, comprising the nucleic acid sequence set forth in SEQ ID NO:20.

11. An adeno-associated virus (AAV) vector comprising the isolated nucleic acid molecule of claim 1.

12. The AAV vector of claim 11, wherein the AAV vector is AAV8.

13. The AAV vector of claim 11, comprising the nucleic acid sequence set forth in SEQ ID NO:20.

14. A pharmaceutical composition comprising the AAV vector of claim 11, and a pharmaceutically acceptable carrier and/or excipient.

15. The isolated nucleic acid molecule of claim 1, further comprising one or more linker sequences.

16. The isolated nucleic acid molecule of claim 15, wherein the one or more linker sequences comprise SEQ ID NO:11, SEQ ID NO:13, or SEQ ID NO:15.

17. The isolated nucleic acid molecule of claim 1, further comprising a Simian virus 40 polyadenylation signal (SV40 pA) and/or a synthetic polyadenylation signal.

* * * * *